US012377145B2

(12) United States Patent
Farrington et al.

(10) Patent No.: US 12,377,145 B2
(45) Date of Patent: *Aug. 5, 2025

(54) HOMEOPATHIC COMPLEX

(71) Applicants: Daniel Farrington, New York, NY (US); Thomas Farrington, Rosscarbery (IE)

(72) Inventors: Daniel Farrington, New York, NY (US); Thomas Farrington, Rosscarbery (IE)

(*) Notice: Subject to any disclaimer, the term of this patent is extended or adjusted under 35 U.S.C. 154(b) by 693 days.

This patent is subject to a terminal disclaimer.

(21) Appl. No.: 17/704,302

(22) Filed: Mar. 25, 2022

(65) Prior Publication Data

US 2022/0288205 A1 Sep. 15, 2022

Related U.S. Application Data

(60) Division of application No. 16/367,465, filed on Mar. 28, 2019, now Pat. No. 11,298,421, which is a continuation of application No. 14/838,465, filed on Aug. 28, 2015, now Pat. No. 10,286,074, which is a continuation of application No. 12/757,257, filed on Apr. 9, 2010, now abandoned, which is a continuation-in-part of application No. PCT/EP2008/008602, filed on Oct. 10, 2008.

(30) Foreign Application Priority Data

Oct. 10, 2007 (IE) .................................... 2007/0737

(51) Int. Cl.
*A61K 41/00* (2020.01)
*A61K 33/00* (2006.01)
*A61K 33/04* (2006.01)
*A61K 33/06* (2006.01)
*A61K 33/28* (2006.01)
*A61K 35/02* (2015.01)
*A61K 35/58* (2015.01)
*A61K 35/583* (2015.01)
*A61K 35/646* (2015.01)
*A61K 36/185* (2006.01)
*A61K 45/06* (2006.01)

(52) U.S. Cl.
CPC .......... *A61K 41/0004* (2013.01); *A61K 33/00* (2013.01); *A61K 33/04* (2013.01); *A61K 33/06* (2013.01); *A61K 33/28* (2013.01); *A61K 35/02* (2013.01); *A61K 35/58* (2013.01); *A61K 35/583* (2013.01); *A61K 35/646* (2013.01); *A61K 36/185* (2013.01); *A61K 45/06* (2013.01)

(58) Field of Classification Search
CPC .... A61K 41/0004; A61K 33/00; A61K 33/04; A61K 33/06; A61K 33/28; A61K 35/02; A61K 35/58; A61K 35/583; A61K 35/646; A61K 36/185; A61K 45/06; A61P 31/00
See application file for complete search history.

(56) References Cited

U.S. PATENT DOCUMENTS

| 5,741,509 A | 4/1998 | Kushner |
| 2006/0165812 A1 | 7/2006 | Charron |
| 2013/0243826 A1* | 9/2013 | Martyn ................ A61K 33/30 |
| | | 424/642 |

FOREIGN PATENT DOCUMENTS

| DE | 202006010673 U1 | 9/2006 |
| RU | 2085204 C1 | 7/1997 |
| WO | 2005063195 A2 | 7/2005 |

OTHER PUBLICATIONS

Horowitz, S, Innovative Therapies in Podiatry and Physical Medicine, Apr. 2010, Alternative and Complementary Therapies, 16(2): 93-99. (Year: 2010).*
Nan's Healing Cream, National Institutes of Health, 2010, Retrieved on Oct. 2, 2024. Retrieved from: <https://dailymed.nlm.nih.gov/dailymed/fda/fdaDrugXsl.cfm> (Year: 2010).*
Ziegler, R., Neu, A., Diabetes in Childhood and Adolescence, 2018, Deutsches Ärzteblatt International, 115:146-156. (Year: 2018).*
American Kidney Fund, Kidney failure (ESRD)—Symptoms, causes andtreatment options, 2022. Retrieved on Oct. 2, 2024. Retrieved from: <https://www.kidneyfund.org/all-about-kidneys/kidney-failure-symptoms-and-causes> (Year: 2022).*
Peterfreund, R.A., Philip, J.H., Critical parameters in drug delivery by intravenous infusion, 2013, Expert Opinion on Drug Delivery, 10(8):1095-1108. (Year: 2013).*
Vinceel Mouth Spray, 2012, Pharmasave. Retrieved on Oct. 3, 2024. Retrieved online: < https://cloverdalepharmasave.com/news/vinceel-mouth-spray/>. (Year: 2012).*
Infectious Disease Associates of Tampa Bay, Skin Ulcers—Risk Factors, Blood Circulation, and Types, 2024. Retrieved on Oct. 2, 2024. Retrieved online: <https://idatb.com/skin-ulcers/>. (Year: 2024).*

(Continued)

*Primary Examiner* — Aaron J Kosar
*Assistant Examiner* — Jennifer Lynn Cain
(74) *Attorney, Agent, or Firm* — Duane Morris LLP; Thomas J. Kowalski

(57) ABSTRACT

The present invention is directed to a homeopathic complex for use in the treatment of various diseases or disorders, including use as an anti-infective agent and/or in the regeneration of diseased or damaged tissue. Ideally, the anti-infective homeopathic complex of the invention may comprise a homeopathic tincture or dilutions thereof of Hepar sulphuris calcareum or other similar profiled Calcarea or Sulphur salt or acid, Lachesis muta or other remedy with a similar profile, Mercurius Solubilis or similar mercury containing remedy and Silica or other silica containing compounds.

15 Claims, 54 Drawing Sheets

(39 of 54 Drawing Sheet(s) Filed in Color)

(56) References Cited

OTHER PUBLICATIONS

Clarke, J.H., Conium Maculatum, 2001, A Dictionary of Practical Materia Medica. Retrieved on Oct. 3, 2024. Retrieved online: <http://www.homeoint.org/clarke/c/conium.htm>. (Year: 2001).*

Mae by Damiva, calendula and hamamelis suppository, 2014, National Institutes of Health, Retrieved on Oct. 3, 2024. Retrieved online: <https://dailymed.nlm.nih.gov/dailymed/drugInfo.cfm?setid=7f4a11c3-95bf-419b-8460-ea9d946fc724>. (Year: 2014).*

Margolis, D., Malay, D.S., Hoffstad, O.J., et al. Prevalence of diabetes, diabetic foot ulcer, and lower extremity amputation among Medicare beneficiaries, 2006 to 2008, 2011, Diabetic Foot Ulcers. (Year: 2011).*

Fomias, E. Orchitis: Internal Treatment. from The Hahnemannian Monthly, vol. 42. Ed. Clarence Bartlett. Philadelphia., 1907. pp 586-587. (Year: 1907).

Warren, I. "The Household Physician". Higgens, Bradley, and Dayton: 1859. pp. 517 and 523. (Year: 1859).

Ellingwood, F. "A Systemic Treatise on Materia Medica and Therapeutics". Chicago Medical Times Publishing Co.: 1905. pp. 69, 70,476,477,666,667,677,678,705,707. (Year: 1905).

Henriette's Herbal. "Achillea" and "Phytolacca". Ellingwood 1919: the American Materia Medica. Retrieved from the internet on: Jul. 16, 2018. Retrieved from: <URL: https://www.henriettes-herb.com/eclectic/ellingwood/phytolacca.html> 9 pages. (Year: 1919).

Hamilton, E. A Guide to the Practice of Homeopathy. J. Leath Homoeopathic Bookseller: 1844. p. 287. (Year: 1844).

Herbs2000. "Bellis" and "Ledum". Internet archive date: Jan. 10, 2004. Retrieved from the Internet on: 2018-07016. Retrieved from: <URL: https://web.archive.org/web/20040901000000*/https://www.herbs2000.com/homeopathy/bellis.htm>. 8 pages.

Morgan, L. Homeopathic Medicine and First-Aid and Emergency care, pp. 51-54 (Year: 1989).

Hartmann, F, ed. "Dr. Caspari's Homoeopathic Domestic Physician". p. 241. (Year: 1852).

McCabe. V. "Practical Homeopathy: A Comprehensive Guide to Homeopathic Remedies and their Acute uses" p. 152. (Year: 2000).

Leavitt et al. "The Science and Art of Obstetrics", p. 606. (Year: 1883).

Barrett, S. Homeopathy: The Ultimate Fake. Retrieved from the Internet: <URL: http://alopsis.gr/afieroma/af-homeopathy-the-ultimate-fake-stephen-barrett-m-d/>, (Year: 2007).

Merck et al. Berl Munch Tierarztl Wochenschr. 102(8):266-72. (Year: 1989).

Jayasuriya, A. Clinical Homoeopathy. p. 586. (Year: 2005).

ABC homeopathy: Hepar Sulphuris Calcareum, Internet Archive Date: Aug. 29, 2003 [Retrieved from the Internet on: Aug. 11, 2014]. Retrieved from: <URL: https://web.archive.org/web/20030829044449/http:/www.abchomeopathy.com/r.php/HEP>.

ABC homeopathy: Lachesis, Internet Archive Date: Sep. 3, 2003 [Retrieved from the Internet on: Aug. 11, 2014]. Retrieved from: <URL: https://web.archive.org/web/20030903151347 http://www.abchomeopathy.com/r.php/Lach>.

Homeopathy, Apr. 26, 2003 (Apr. 26, 2003), Retrieved from the Internet: URL:http://web.archive.org/web/20030426182659/http://www.vaccinetruth.org/homeopathy.html>.

What is the Difference between Classical and Complex Homeopathy, Feb. 26, 2007 (Feb. 26, 2007), Retrieved from the Internet: URL:http://web.archive.org/web/20070226215356/http://www.ritecare.com/homeopathic/guide_general.asp.

Home Remedy Central: Lachesis Mutus/Lachesis/Lach, Retrieved from the Internet on: Aug. 11, 2014. Retrieved from: <URL: http://www.homeremedycentral.com/en/homeopathic-remedies/homeopathy/lachesis.html>.

Herbs2000: St. John's Wort, Internet Archive Date: Dec. 4, 2003 [Retrieved from the internet on: Aug. 11, 2014]. Retrieved from: <URL: https://web.archive.org/web/20031204095827/http://www.herbs2000.com/herbs/herbs_st_johns_wort.htm>.

Lippe, C. 33. Skin: wounds. From: Repertory to the more characteristic symptoms of the Materia medica. Copyright 1879. p. 128.

ABC Homeopathy: Arsenicum iodatum. Internet Archive Date: Aug. 28, 2003 [Retrieved from the Internet on; Aug. 11, 2014]. Retrieved from: <URL: https://web.archive.org/webL20030828234519/http://www.abchomeopathy.com/r.php/Ars-i>.

Herbs2000: Bellis. Internet Archive Date: Feb. 1, 2004 [Retrieved from the internet on: Aug. 11, 2014]. Retrieved from: <URL: https://web.archive.org/web/2004011_0133347/http://www.herbs2000.com/homeopathy/bellis.htm>.

ABC Homeopathy: Led um Palustre. Internet Archive Date: Sep. 4, 2003 [Retrieved from the Internet on: Aug. 11, 2014]. Retrieved from: <URL:https://web.archive.org/web/20030904195418/http://www.abchomeopathy.com/r.php/Led>.

Herbs2000: Witch Hazel, Internet Archive Date: Dec. 4, 2003 [Retrieved from the internet on: Aug. 11, 2014]. Retrieved from: <URL: https://web.archive.org/web/20031204000820/http://www.herbs2000.com/herbs/herbs_witch_hazel.htm>.

ABC Homeopathy: Phytolacca decandra, Internet Archive Date: Sep. 5, 2003 [Retrieved from the Internet on: Aug. 11, 2014]. Retrieved from: <URL: https://web.arehive.org/web/20030905224726/http://www.abchomeopathy.com/r.php/Phyt>.

Barrett, Stephen. Homeopathy: The Ultimate Fake, Internet Archive Date: Feb. 22, 1999 [Retrieved from the Internet on: Dec. 30, 2011] Retrieved from the Internet: <URL: http://web.archive.org/web/19990222093657/http://www.guackwatch.com/01QuackeryRelatedTopics/homeo.html>.

Dana Ullman: Infectious Disease: Effective Alternatives to Antibiotics (1991) Retrieved from the Internet: URL:http://healthy.netiscr/Article.asp?Id=885xcntr=6.

Duval Jean: Treating Mastitis Without Antibiotics (1996) Retrieved from the Internet: URL:http://eap.mcgill.calpublications/EAP69.html.

Abstract Only: Oberbaum et al. Harefuah. (Aug. 1992) 123(3-4):79-82, 156.

Pawaskar et al., National Journal of Homoeopathy Sep./Oct. 2002 vol. 4 No. 5. [Retrieved from the Internet on: Aug. 11, 2014]. Retrieved from: <URL: http://www.nihonline.com/2002/sep_oct_no5/cases/injury_cases_quantified3.shtml>.

Rostek H et al., Prerequisites and circumstances for the realization of clinical trials with homeopathic combination drugs. Part 2, Pharmazeutische Industrie, Aulendorf. DE, vol. 61, No. 11 (Jan. 1, 1999) pp. 980-983.

Rostek H et al., Prerequisites and circumstances to carry out clinical trials with homeopathic combination drugs. Part 1, Pharmazeutische Industrie, Aulendorf, DE, vol. 61, No. 10 (Jan. 1, 1999) pp. 875-877.

Tschech B., Who Heals is Right! A Discussion of Complex Homeopathic Remedies, (Aug. 19, 2007) Retrieved from the Internet: URL: http://web.archive.org/web/2007081902244/http://www.hpathy.com/papersnew/tschec_h-complexhomeopathy.asp.

American Academy of Dermatology Association, How To Care for Your Skin During and After Radiation Therapy. Retrieved from the Internet on: Feb. 26, 2021. <URL: https://web.archive.org/web/20210115201439/https://www.aad.org/public/diseases/skin-cancer/types/common/melanoma/radiation-care> 4 pages (2021).

* cited by examiner

The effect of homeopathic treatment on $IgG_1$ concentrations in milk from Holstein cows.

The effect of homeopathic treatment on $IgG_2$ concentrations in milk from Holstein cows.

FIG. 13a (Day 1)

FIG. 13b (Day 11)

FIG. 13d (X-ray on Day 1 of injury)

FIG. 13e (X-ray Day 1 of injury)

FIG. 13f (X-ray on Day 1 of injury)

HOMEOPATHIC COMPLEX

INCORPORATION BY REFERENCE

This application is a Division of U.S. application Ser. No. 16/367,465 filed Mar. 28, 2019, issued as U.S. Pat. No. 11,298,421, which is a Continuation of U.S. application Ser. No. 14/838,465 filed Aug. 28, 2015, issued as U.S. Pat. No. 10,286,074, which is a Continuation of U.S. application Ser. No. 12/757,257 filed Apr. 9, 2010, abandoned, which is a continuation-in-part application of International Patent Application Number PCT/EP2008/008602 filed 10 Oct. 2008, which published as PCT Publication Number WO 2009/047005 on 16 Apr. 2009, which claims benefit of Irish patent application Serial Number 2007/0737 filed 10 Oct. 2007.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention is directed to a homeopathic complex for use in the treatment of various diseases or disorders, particularly for use as an anti-infective agent and/or in the regeneration of diseased or damaged tissue.

BACKGROUND OF THE INVENTION

Homeopathy is a form of alternative medicine and traditional homeopathy has been practiced for nearly two hundred years all over the world. Homeopathic medicine has its underpinnings in what is referred to as the Law of Similars or the similia principle. The fundamental principle of homeopathy states that substances may be used to treat disorders whose manifestations are similar to those which they themselves produce in a healthy subject (Churchill Livingstone's International Dictionary of Homeopathy Edited by Jeremy Swayne (2000) page 193, 1st Edition).

Homeopathic tinctures differ to herbal tinctures in their method of production, base ingredients used and their dilution.

Homeopathic tinctures are derived from many materials, whereas herbal tinctures are derived from plant materials only. Homeopathic mother tinctures are made following monographs laid down in the HAB (GHP-German Homeopathic Pharmacopeia), EP European Pharmacopeia, French Homeopathic Pharmacopeia, BHP-British Homeopathic Pharmacopeia, and HPUS-Homeopathic Pharmacopeia of the United States. While plants are the base ingredients for approximately 65% of homeopathic tinctures, the remainder are made from many mineral, animal or imponderable substances. Thus, the production of a homeopathic tincture involves the use of base ingredients from x-ray to diamond to *Pulsatilla* (the Wind flower).

A homeopathic mother tincture, comprising base ingredients such as for example fresh plants, is generally prepared by extracting the ingredients in a suitable solvent, followed by the steps of comminution, maceration and squeezing according to accepted homeopathic Pharmacopoeia. Suitable solvents include alcohol, water, water-alcohol mixtures, glycerine or isotonic sodium chloride solutions. Other techniques include tituration (grinding) with lactose to form a powdered dilution. On the contrary herbal tinctures are prepared in a different manner generally involving the use of a solvent to extract the base ingredient without the maceration or grinding steps.

In homeopathy, a base preparation or mother tincture of a homeopathic remedy is made by liquid extraction (via maceration) of a herbal, mineral, animal or imponderable substance by dissolving the herbal, mineral, animal or imponderable in a solvent. In use, the mother tincture or 1× potency ($1 \times 10^{-1}$ dilution) may be used as is, for example in diseases where the patient can benefit from the active principles within the tincture. This assumes that the base tincture is not of a toxic nature. Optionally, the mother tincture may be further diluted. Essentially, a series of dilutions are prepared from the base preparation or mother tincture. This step is called potentization and involves a series of dilutions. Between each series the diluted substance is succussed (shaken in a vigorous manner). The process of dilution and succussion leads to a gradual loss of chemical toxicity while gradually increasing the homeopathic potency. The more dilute remedies being of greater potency.

Thus, homeopathic tinctures require a further dilution step in the production of the mother homeopathic tincture. This means that a homeopathic mother tincture is a 1× or 1 in 10 dilution of the base ingredient. Additionally, it is important to note that it is not possible to reconstitute a herbal mother tincture from a homeopathic mother tincture. Thus, what makes a tincture truly homeopathic is the additional dilution process to where the final mother tincture represents a dilution of 1:10 of the base ingredient.

Thus, homeopathic tinctures differ to herbal remedies in that a further dilution is required in the production of homeopathic tinctures so that the base material is 10% of the final mother tincture. As expanded on above a homeopathic mother tincture from fresh plants is prepared by extracting the ingredients in a suitable solvent, such as a alcohol, water-alcohol mixtures, water, glycerine or isotonic sodium chloride solution are used as a vehicle (solvent) followed by the steps of comminution, maceration and squeezing. Other techniques include tituration (grinding) with lactose to form a powdered dilution. On the other hand, herbal remedies are less dilute than homeopathic remedies and are prepared in a different manner merely involving the use of a solvent to extract the ingredient.

Homeopathic preparations as defined above must follow the monograph as laid down in the various homeopathic pharmacopoeias, for example the German Homeopathic Pharmacopeia (G.H.P. or H.A.B.), European Pharmacopeia (E.P.), French Homeopathic Pharmacopeia, British Homeopathic Pharmacopeia (B.H.P.) or the Homeopathic Pharmacopeia of the United States (H.P.U.S.).

The dilution and sucussion level of homeopathic drugs are denoted as "x", "X" or "d" for the decimal scale or centesimal "c", "C" scale or LM (Q) as 1:50,000 dilutions. This is expanded in the table below.

For example, for a "3×" preparation, the mother tincture is diluted with nine parts of the

| Decimal | | | Centesimal | | |
| --- | --- | --- | --- | --- | --- |
| POTENCY | DILUTION | CONCENTRATION | POTENCY | DILUTION | CONCENTRATION |
| 1x or D1 | 1:10 | $10^{-1}$ | 6c | $1:10^{12}$ | $1 \times 10^{-12}$ |
| 2x or D2 | 1:100 | $10^{-2}$ | 7c | $1:10^{14}$ | $1 \times 10^{-14}$ |
| 3x or D3 | 1:1000 | $10^{-3}$ | 11c | $1:10^{23}$ | $1 \times 10^{-23}$ |
| 4x or D4 | 1:10000 | $10^{-4}$ | 12c | $1:10^{24}$ | $1 \times 10^{-24}$ |
| 5x or D5 | 1:100000 | $10^{-5}$ | 30c | $1:10^{60}$ | |
| 6x or D6 | 1:1000000 | $10^{-6}$ | 200c | $1:10^{400}$ | |
| 30x or D30 | $1:10^{30}$ | $10^{-30}$ | 1M | $1:10^{2000}$ | |
| | | | 10M | $1:10^{20000}$ | |
| | | | LM1 (Q) | 3c diluted | 1:50,000 | desired diluent, in either liquid or powder form. The resultant mixture is then diluted a second time, in a ratio of one part mixture to ten parts solvent and the resulting mixture is diluted a third time in a ratio of one to ten. Therefore, the 3× or D3 potency is actually at $1 \times 10^{-3}$ (¹⁄₁₀₀₀) of the mother tincture. Similarly, a 6× potency dilution would be at $1 \times 10^{-6}$ of the original solution. In the "C scale" each dilution is done with ninety-nine parts diluent to the original mixture. Therefore, a 3C potency dilution is at $1 \times 10^{-6}$ potency of the original mixture. Ideally, x potency dilution is usually carried out with approximately 10 to 20 succussions, while C potency dilutions are carried out with anywhere from 10 to 100 succussions and in some cases 1000 sucussions between dilutions. The more stages of dilution and succussion a homeopathic solution has undergone, the higher the potency of that remedy.

These x and C scales are recognized by the main Homeopathic Pharmacopoeia such as the German Homeopathic Pharmacopoeia (G.H.P.), French Homeopathic Pharmacopoeia, British Homeopathic Pharmacopoeia, the Homeopathic Pharmacopeia of the United States (H.P.U.S.) and the European Homeopathic Pharmacopeia.

When choosing the homeopathic remedy to administer, it is important to note that the homeopathic approach to treatment hypothesizes that the closer the matching of symptoms of the individual to be cured to those of the medicine being used, the greater the curing effect of the homeopathic treatment. This process is facilitated by these symptoms being catalogued in the homeopathic Materia *Medica* and various Homeopathic Repertories. The selection of the remedy is of prime importance in a successful homeopathic treatment. Of secondary importance, is the selection of the correct therapeutic potency. The potency of the medicine must be matched to the state of the patient and the state of the disease process. Thus, in a young healthy individual with an acute disease process a high potency medicine would generally be appropriate, whereas in an elderly patient with a chronic disease a low potency or even a diluted LM potency may be more appropriate.

To demonstrate the effectiveness of a homeopathic drug, the drug is tested by a "proving" in order to see how the drug will affect an otherwise healthy person. Hundreds of compounds have been tested in this manner and these are catalogued in the various Homeopathic Repertories and Materia *Medica*. Homeopathic repertories generally provide listings of the human anatomy (or in some clinical repertories clinical conditions are listed) and list associated symptoms and treatments for these symptoms. Materia *Medicae* list homeopathic drugs and identify the maladies and symptoms each drug treats. The material in the Materia *Medicae* is derived from all the information about the homeopathic drug and includes data from homeopathic provings, toxicity, and clinical use. More over, where a repertory lists a symptom, it classifies possible treating compounds as either first, second or third degree and in some cases fourth degree remedies for that symptom. Typically, a homeopathic practitioner will prescribe homeopathic medicine that has the best overall recorded similarity to the overall disease picture in the patient. This also involves taking into account how important each symptom is in that picture especially the strange rare and peculiar symptom(s), mental, emotional, aetiological, general symptoms, local symptoms and modalities. A homeopathic medicine with first degree indications for a particular symptom picture is more likely to be used than a remedy with a similar second degree picture unless the second degree picture has a greater similarity to the overall patient picture. A homeopathic medicine with a third degree indication would be less likely to be used unless there was a greater similarity and particularly if there was a strange rare and peculiar symptom present. Homeopathic tinctures and their derivative potencies or dilutions can be used in the treatment of a wide variety of diseases, conditions and or symptoms.

Classical homeopathy involves the administration of a homeopathic medicine based on a single ingredient. The use of a homeopathic complex comprising multiple different ingredients is contrary to conventional classical homeopathy teachings and in some pharmacopoeia this is not recommended ("Hahnemann Revisited-A Textbook of Classical Homeopathy For the Professional" Luc DeSchepper, First Edition 2001, "Achieving and Maintaining the Similimum Strategic Case Management for Successful Homeopathic Prescribing" LucDeSchepper, First Edition 2004, "The Organon of the Medical Art" by Samuel Hahnemann edited by Wenda Brewster O'Reilly First Edition, 1996.)

The treatment of most conditions in humans or animals using conventional methodologies involves the administration of conventional drug treatments. Such conventional treatments can have major side-effects to the detriment of many internal organs. These side-effects, ranging from mild to severe, can prevent their application to many patients. For example, statins which are used in the treatment of high cholesterol have many side effects ranging from mild to severe. These include gastrointestinal symptoms. Statins can also have severe side effect on the liver and kidney. Rhabdomyolysis (the pathological breakdown of skeletal muscle) may lead to acute renal failure when muscle breakdown products damage the kidney. Thus, with a condition like high cholesterol when it is being treated by statins, the patient must be continually monitored to assess whether unrelated systems are being adversely affected.

Many other therapies for a wide range of conditions also result in side effects ranging from mild to potentially lethal side effects. These side effects and other detrimental effects can also reduce patient compliance to the drug therapy. For example, many anti-arthritics and anti-inflammatories have side effects at the circulatory hepatic or nephrological level. Anti-anxiety drugs (anxiolytics) can have either a sedative side effect or other often more hidden behavioural effects can occur, such as dissociation or there may be a long term inability to cope without the drugs. It has been recorded that drugs used for the purposes of sedation have in some cases resulted in the aggravation of symptoms such as aggression following their use. For example, acepromazine/acetylpromazine (ACP) is used as a sedative/tranquilizer by veterinarians. ACP is frequently used in combination with other sedatives and anaesthetics to provide smoother sedation ACP can cause side effects, such as effects on blood pressure. In some cases the lower blood pressure remains long after the drug has been taken. Due to these side-effects, it may not be possible to administer ACP to some animals. Anti-pruritic drugs, which reduce pruritus, or itching, can have side effects such as drowsiness and lowering blood pressure.

Therefore, it is desirable to provide a treatment which addresses these issues and can mitigate at least some of the significant side-effects and problems associated with conventional therapies.

Furthermore, another problem with current conventional methodologies is that no therapy is 100% effective across a population no matter what condition is targeted. Any therapy which can improve effectiveness across a wider range of subjects would be desirable.

There is a need for less expensive, safer and more user friendly therapeutic agents for use in the treatment of a wide variety of conditions. Hence, the present invention is directed to specific homeopathic complexes which can treat a wide number of disorders without the negative side effect and costs issues usually associated with conventional pharmaceuticals.

Citation or identification of any document in this application is not an admission that such document is available as prior art to the present invention.

SUMMARY OF THE INVENTION

According to a general aspect of the present invention, there is provided a homeopathic complex comprising a homeopathic tincture or dilutions thereof of a silica containing remedy, a mercury containing remedy, a snake or spider remedy, and a *Calcarea* or Sulphur salt or acid.

According to this general aspect of the invention, the homeopathic complex comprises a homeopathic tincture or dilutions thereof of Hepar sulphuris calcareum [Hep] or other similar profiled *Calcarea* or Sulphur salt or acids, Lachesis muta [Lach] or other remedy with a similar profile, Mercurius Solubilis [Merc] or Similar Mercury based remedy; and Silica [Sil] or other silica containing compounds.

According to a further general aspect of the present invention, there is provided a homeopathic complex as defined herein for use as an anti-infective agent and/or in the regeneration of disease or damaged tissue.

According to a further general aspect of the present invention, there is provided a method for the treatment or prophylaxis of infection and/or regeneration of disease or damaged tissue comprising administering to a subject in need thereof an effective amount of the homeopathic complex as defined herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

FIG. 6B shows the change at day 12. FIG. 6C shows the change within 30 days and FIG. 6D shows that within a year the scar was virtually completely gone and almost the entire area had normal hair re-growth;

FIGS. 13A to 13F show the cat of Example 20.

DETAILED DESCRIPTION

Figure 1A:
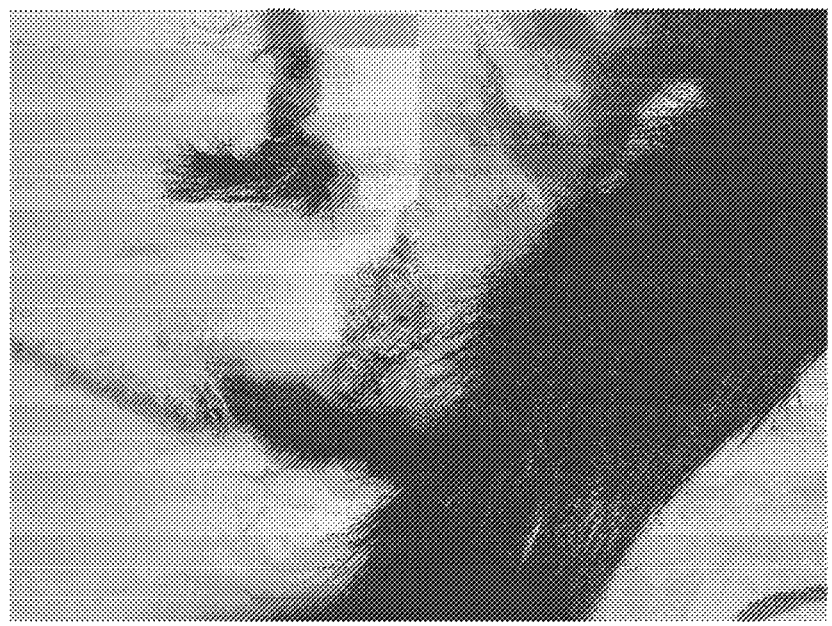
FIGS. 1A & 1B show the Feline of Example 2 pre-treatment and 24 hours later.

In the specification the term "by weight" refers to the weight of the final composition and "by volume" refers to the volume of the final composition.

In this specification the term "homeopathic tincture and dilutions thereof" includes a homeopathic mother tincture and/or its various dilutions or potencies derived from the homeopathic mother tincture. It will also be understood that the homeopathic tincture comprises one or more extracts derived from plant, mineral, animal and/or imponderable substances.

In the specification, it will be understood that the term "anti-infective" agent covers both "antimicrobial" or "anti-bacterial" effects and covers biocidal or biostatic activity against various types of organisms including, but not limited to, bacteria, fungi, viruses, yeasts and/or moulds.

Finally, in the specification, it will be understood that the homeopathic ingredients are referred to using different nomenclature or synonyms. For example, Hepar sulphuris calcareum can also be referred to as [Hep] or Hepar sulphuris, they all refer to the same homeopathic ingredient. Furthermore, for some ingredients, specific species names are given in places and family names are given in other places. For example, Echinacea is generally referred to in the description whereas in the examples the preferred Echinacea plants are mentioned, such as Echinacea angustifolia [Echi] and Echinacea purpurea [Echi-p]. These comments are applicable to most ingredients used in the homeopathic complexes of the invention. The different nomenclature and family/species for each ingredient is well known in the art and can be found in the homoeopathic literature. The following table highlights the different names, long names and short names given to the same homeopathic ingredient.

| Name Of Remedy | Abbreviation | Alternative Nomeclature/Synonyms |
|---|---|---|
| Hepar sulphur | hep. | Hepar sulphuris calcareum; (Hep-s); The Calcarea sulphurata Hahnemanni. Also impure Sulphide of Calcium |
| Lachesis mutus | Lach. | Lachesis Muta; Bushmaster snake Lach. Lachesis muta. Bushmaster. Surukuku. Trigonocephalous lachesis |
| Merc Sol | Merc. | Mercurius Solubilus; Mercurius Soublis Hahnemanni; Mercurius Merc-s., Merc., also Metallic Mercury Quicksilver, Argentum vivum |
| Silica terra | Sil. | Silica terra Silicea Terra Silicea Flint. Silex. Silicic anhydride. Silicon dioxide, Silicia |
| Aconitum napellus | Acon. | Aconite., Monkshood. Wolfsbane. Common Aconite. N. O. Ranunculacee. |
| Adrenalinum | Adren. | Adrenalinum. Extract of adrenal glands. Sarcode |
| Aesculus hippocastanum | Aesc. | Aesculus Horse Chestnut. Aesculus hippocastanum. Hippocastanum vulgaris. N. O. Sapindaceae |
| Alfalfa | Alf | Medicago sativa. California Clover. Lucerne |
| Antimonium tartaricum | Ant-t | Tartrate of Antimony and Potash. Tartar Emetic. Antimonium tartaricum |

-continued

| Name Of Remedy | Abbreviation | Alternative Nomeclature/Synonyms |
|---|---|---|
| *Apis mellifica.* | *Apis.* | Apis-mel., Honey-Bee. N. O. Insecta. |
| *Arnica montana* | *Arn.* | *Arnica.*, Leopard's Bane. Brusiewort. Fall Herb. N. O. Composite. |
| Arsenicum album | Ars. | Ars Alb., Arsen Alb., Arsencium Alb., Arsenic Trioxide. The white oxide of metallic Arsenic (Arsenicums) |
| Arsenicum iodatum | Ars-i. | Ars Iod., Arsenicum Iod., Iodide of Arsenic (Arsenicums and Iodatums) |
| *Astragalus membranaceus* | *Astra-m* | *Astragalus membranaceus* Astra-m. *Astragalus menziesii*. N. O. Leguminose some confusion exists as to whether these are fully the same from herb to homeopathy |
| Aurum metallicum | Aur | Aur. Aurum metallicum. Metallic Gold. |
| *Baptisia tinctoria* | *Bapt* | *Baptisia*. Wild Indigo N. O. Leguminosae |
| Baryta carbonica | Bar-c. | Baryta carb., Carbonate of Barium. Bar-c. with which are included symptoms of Baryta acetica. |
| *Belladonna* | *Bell.* | *Atropa belladonna*. Deadly Nightshade. N. O. Solanaceae. |
| *Bellis perennis* | Bell-p. | Daisy. N. O. Composite |
| *Berberis Vulgaris* | *Berb* | Barberry. N. O. Berberidacae. |
| *Bryonia alba* | *Bry.* | *Bryonia. Bryonia dioica*. Wild Hops. White Bryony. N. O. Cucurbitaceae |
| *Bufo rana* | *Bufo* | *Bufo., Bufo Satytiensis*. N. O. Bufonide, Batrachide. Toad Poison. Including the common variety, *Bufo rana* and the Brazilian toad, *Bufo Satytiensis* |
| *Cactus grandiflorus* | cact | *Cact. Cactus grandiflorus. Cactus Selenicereus*. Night-blooming *Cereus. Cereus grandiflorus*. N. O. Cactaceae |
| *Caladium seguinum* | *Calad.* | *Calad. Caladium.,* American *Arum. Arum seguinum*. Dumb Cane. N. O. Araceae |
| Calcarea carbonica | Calc | Calc Carb., Calcarea carbonica. Calcarea ostrearum. Conchae Praeparatae. Impure Calcium Carbonate. |
| Calcarea fluorica | Calc-f | Calc Fluor., Calcarea fluorica. Calcium Fluoride. Fluorspar. |
| Calcarea phosphorica | Calc-p | Calc Phos., Calcium phosphate. Calcarea phos. Phosphate of Lime. Tricalcic Phosphate |
| *Calendula officinalis* | *Calen.* | *Calendula*, Pot Marigold. N. O. Composite. |
| *Cantharis vesicatoria* | *Canth.* | *Cantharis.*, Spanish Fly. *Lytta vesicator*. N. O. Insecta, Coleoptera |
| Carbo vegetabilis | Carb-v | Carbo vegetabilis. Vegetable Charcoal. Impure carbon |
| *Carduus marianus* | Card-m. | *Carduus* mar. St. Mary's Thistle. *Silybum*. N. O. Composite |
| *Chamomilla* | *Cham.* | *Chamomilla Matricaria* German Chamomile N. O. Composite. |
| *Chelidonium majus.* | *Chel.* | *Chelidonium.*, Greater Celandine. N. O. Papaveracae. |
| *China officinalis* | *Chin.* | *China.*, China Regia. Kina-Kina. Peruvian Bark. *Cinchona calisaya* aut *cinchona succirubra*. N. O. Rubiacae |
| *Chionanthus virginica* | *Chion.* | Fringe-tree bark. *Chionanthus americana*. N. O. Oleacee. |
| *Cocculus indicus.* | *Cocc.* | *Cocculus.*, Indian Cockle. N. O. Menispermacae. |
| *Conium maculatum* | *Con.* | *Conium mac.*, Poison Hemlock. N. O. Umbelliferae. |
| *Crotalus horridus* | Crot-h. | *Crotalus-h., Crotalus horridus.* The Rattlesnake (venom) Crotalidae |
| *Drosera rotundifolia* | *Dros.* | *Drosera.* Round-leaved Sundew. N. O. Droseraceae. |
| *Echinacea angustifolia* | *Echi.* | Purple Cone-flower. *Echinacea angustifolia. Echinacea rudbeckia*. N. O. Composite |
| *Echinacea purpurea* | Echi-p. | Black Sampson. N. O. Composite. |
| *Equisetum hyemale* | *Equis.* | *Equisetum.*, Scouring-rush. Horse-tail herb. N. O. Equisetaceae |
| *Euphrasia officinalis* | *Euphr.* | *Euphrasia*. Eyebright. N. O. Scrofulariaceae |
| Ferrum phosphoricum | Ferr-p. | Ferric Phosphate. Ferrum phosphoricum. Ferroso-ferric phosphate. White Phosphate of Iron, (Schusslers's). |
| *Galium aparine* | *Gali.* | *Galium* ap. Goose grass. Cleavers. N. O. Galiacae, |
| *Gelsemium sempervirens* | *Gels.* | *Gelsemium.*, Yellow Jasmine. *Gelsemium sempervirens. Gelsemium lucidum*. Yellow Jessamine. *G. Nitidum. Bignonia sempervirens*. N. O. Loganiacee. |

-continued

| Name Of Remedy | Abbreviation | Alternative Nomeclature/Synonyms |
|---|---|---|
| Graphites | Graph. | Graphites naturalis. Black Lead. Plumbago. |
| *Grindelia robusta.* | *Grin.* | *Grindelia squarrosa.* Rosin-wood. N. O. Composite |
| Gunpowder | Gunp. | Carbon-Sulphur-Kali-Nitricum. Black Gunpowder |
| *Hamamelis virginiana* | *Ham.* | *Hamamelis.*, Witch-hazel. *Hamamelis macrophylla. Hamamelis dioica.* N. O. Hamamelidacee. |
| Histaminium muriatricum | Hist. | Imidazolethylamine. Histamine hydrochloricum |
| *Hydrastis canadensis* | *Hydr.* | *Hydrastis.*, Golden Seal. The Orange-root. Yellow Puccoon. N. O. Ranunculacee. |
| *Hypericum perforatum* | *Hyper.* | *Hypericum.*, St. John's-wort. *Hypericum perforatum.* N. O. Hypericacee |
| Iodium | Iod | Iodium purum. Iodine. An element. |
| *Ipecacuanha* | *Ip* | *Ipecac.*, Ipec root. *Cephaelis ipecacuanha.* N. O. Rubiaceae |
| Kalium carbonicum | Kali-c | Kali Carb., Kali carbonicum. Carbonate of potassium. Potassium Carbonate |
| Kalium Iodatum | Kali-i | Kali Iod., Potassium iodide. Kali hydroiodicum. Solution. |
| Lac caninum | Lac-c | Lac can., Dog's milk. |
| Lac vaccinum defloratum | Lac-d. | Cow Skimmed Milk. |
| Lac Vaccinum | Lac-v | Lac Bovinum., Cows Milk |
| *Lappa arctium* | *Lappa.* | *Arctium lappa.* Burdock. *Lappa* Major. *Lappa officinalis.* Arcion, (Greek). Gobo. Great Clote Burre. N. O. Composite. |
| *Laurocerasus* | *Laur.* | Cherry laurel. *Cerasus Laurocerasus.* Common Laurel. *Prunus Laurocerasus.* N. O. Rosacea. |
| *Lavendula vera* | Lav-v | Lavender |
| *Ledum palustre* | Led. | *Ledum.*, Marsh tea. Wild Rosemary. Marsh Cistus. Labrador Tea. N. O. Ericaceae |
| *Lobelia inflata* | *Lob.* | Indian tobacco, Puke weed. N. O. Lobeliacee. |
| *Lycopodium clavatum* | *Lyc* | *Lycopodium.*, Club moss. *Muscus terrestris repens. Pes ursinus.* Wolfs-claw. N. O. Lycopodiacee |
| *Mezereum* | *Mez..* | *Daphne mezereum.* Spurge olive. *Chameleons germanica.* Mezereon. N. O. Thymelaceae |
| *Millefolium* | *Mill.* | *Millefolium Achillea.* Yarrow. *Achillea millefolium.* N. O. Composite |
| Natrium muriaticum | Nat-m. | Nat mur., Salt, Sodium chloride. Common Rock Salt |
| Nitricum acidum | Nit-ac. | Nitric acid. Aqua Fortis. Solution. |
| *Nux vomica* | Nux-v. | *Nux.*, Poison nut. *Strychnos Nux vomica.* N. O. Loganiacae. |
| *Paeonia officinalis* | *Paeon.* | Peony. N. O. Ranunculaceae. |
| *Phytolacca decandra* | *Phyt.* | *Phytolacca.*, *Phytolacca decandra.* Poke root. Poke weed. Virginian Poke. Pole-root. Red Ink Plant. Garget Weed,. N. O. Phytolaccaceae |
| Phosphorus | Phos. | The Element Phosphorus - red amorphous Phosphorus |
| Prednisolone | Predn | Prednisolone a synthetic corticosteroid |
| *Pulsatilla pratensis* | *Puls.* | *Pulsatilla.*, *Pulsatilla nigricans. Pulsatilla pratensis. Anemone pratensis.* Pasque-flower. Wind flower. N. O. Ranunculaceae |
| Pyrogenium | Pyrog. | Pyrogen., Pyrogenium. Rotten meat pus., Pyrexin. Sepsin. |
| *Ranunculus bulbosus* | Ran-b. | *Ranunculus.* Buttercup. Bulbous Crowfoot. N. O. Ranunculacee |
| *Rhus toxicodendron* | Rhus-t. | *Rhus Tox.*, Poison oak. *Rhus radicans.* |
| *Rhus venenata* | Rhus-v. | *Rhus ven.*, Poison elder. Poison Sumac. Swamp Sumac. N. O. Anacardiacae |
| *Rumex crispus* | *Rumx.* | *Rumex.* Yellow dock. The Curled Dock. N. O. Polygonaceae |
| *Ruta Graveolans* | *Ruta.* | *Ruta graveolens.* Garden Rue. Bitterwort. N. O. Rutaceae |
| *Sabal serrulata* | *Sabal* | Saw palmetto. *Serenoa serrulata.* N. O. Palmaceae |
| *Sepia officinalis* | *Sep* | *Sepia.*, *Sepia succus.* Cuttlefish Ink. *Sepia officinalis.* N. O. Cephalopoda. |
| Sol | Sol. | Sol. Sunlight. Milk sugar is exposed to concentrated sun's rays and stirred with a glass rod until saturated. |
| *Solidago virgaurea.* | *Solid.* | *Solidago.*, Goldenrod. N. O. Compositae. |
| Stannum metallicum. | Stann. | Stannum Tin. Trituration of the pure metal |
| *Staphisagria* | *Staph.* | Staphysagria. *Delphinium staphysagria.* Stavesacre. N. O. Ranunculaceae |
| *Stellaria media* | *Stel.* | Chickweed. N. O. Caryophyllaceae |
| *Strophantus hispidus* | Strop-h. | *Strophantus.* Kombe seed. Onaye. Onage. Poison of Pahonias. N. O. Apocynaceae |

| Name Of Remedy | Abbreviation | Alternative Nomeclature/Synonyms |
| --- | --- | --- |
| Sulphur | Sulph. | Sulphur Sublimatum. Brimstone. Sublimed Sulphur |
| Symphytum officinale | Symph. | Comfrey. Knitbone. Symphytum officinale. Healing Herb. N. O. Boraginaceae. |
| Taraxacum officinale | Tarax | Taraxacum. Dandelion. Leontodum taraxacum. N. O. Compositae |
| Tarentula Cubensis | Tarent-c. | Tarentula Cub., The Cuban tarentula. Tarentula cubensis. Mygale Cubensis. Aranea peluda. N. O. Araneideae |
| Tarentula Hispanica | Tarent. | Spanish tarentula. Lycosa tarentula. N. O. Araneideae. |
| Thiosinaminum. | Thiosin. | Rhodallinum. Mustard seed oil. Allyl sulphocarbamide. Derived from Oil of Mustard-seed. Rhodallin |
| Thuja occidentalis | Thuj. | Thuja., Arbor vitae. N. O. Coniferae |
| Triticum repens | Tritic. | Triticum. Couch grass. Agropyrum Repens. Cutch-grass. Quitch grass. N. O. Gramineae |
| Urtica urens | Urt-u. | Stinging nettle. Urtica dioica. The Common Nettle, has similar if not identical properties. N. O. Urticaceae. |
| Uva ursi | Uva. | Bearberry. Arctostaphylos. N. O. Ericaceae. |
| Zincum metallicum | Zinc | Zincum Met. . Zinc. An Element. Zn. |
| NOSODES | | |
| Bacillinum | Bac. | A Tuberculosis Nosode. Bacillinum. A maceration made from a tubercular sputum. |
| Corynebacterium | Coryne | A Corynebacterium Nosode |
| Tuberculinum Aviairae | Tub-a. | Avian tuberculosis - Chicken tuberculosis Tuberculinum Avis Nosodes |
| Tuberculinum Bovinum | Tub Bov | Bovine Tuberculosis - Tuberculinum Bovinum of Kent sometimes same as below |
| Tuberculinum Koch | Tub. | Tuberculosis Nosode. The Tuberculinum Bovinum of Kent. Tuberculinum of Koch. Liquid potencies. Nosode is prepared either from tubercular abscess or from a glycerine extract of pure cultivation of human tubercular bacillus. |
| Staph Aureus Nosode | Staphycoc | Staphylococcus bacteria. Staphylococcinum. |
| Streptococcus Nosode | Streptoc. | Streptococcinum. Streptococcinum bacteria. |
| Medorrhinum | Med. | Gonorrhea nosode.. Glinicum. Potencies of the Virus. |
| Colibacillinum 1 | Coli | Coliform Nosode |
| Colibacillinum 2 | E. Coli | Escherichia coli |

According to a first aspect of the invention, there is provided a homeopathic complex comprising a homeopathic tincture or dilutions thereof of Hepar sulphuris calcareum [Hep] or other similar profiled *Calcarea* or Sulphur salt or acid;

Lachesis muta [Lach] or other remedy with a similar profile; Mercurius Solubilis [Merc] or similar mercurius based remedy; and Silica [Sil] or other silica containing compounds.

It will be understood that Hepar sulphuris calcareum [Hep], Lachesis muta [Lach], Mercurius Solubilis [Merc]; and Silica [Sil] may be replaced or supplemented with the additional remdies as outlined below. The main characteristic of the additional remedies is that they have similar profiles to the remedy they replace or supplement.

Furthermore, it will also be understood that these remedies may be replaced or supplemented with chemical equivalents or bioequivalents of the homeopathic remedies which essentially mimic the active moiety within the homeopathic remedy and ideally results in an agent with a similar profile to the homeopathic remedy. For example, venoms such as snake or spider remedies may be replaced by ammonium carbonate. Additionally and by way of non-limiting examples, the active agent within the Solanacea family (e.g. *Belladonna, Strammonium, Hyoscyamus*) are the alkaloids, particularly the tropane alkaloids, and the active agent within the Loganiaceae family (e.g. Iganthia, *Gelsemium*, Nux Vomica) is strychnine (Strychnos). Other chemical equivalents or bioequivalents of homeopathic ingredients are well known in the field.

According to a specific embodiment, Calc Sulph, Calc Sil or similar profiled *Calcarea* or Sulphur or salts or acids thereof may be present in addition to or instead of Hepar Sulph.

It will be understood that other similar snake or spider remedies with a similar septic shock profile to Lachesis muta can be used. Such remedies include but are not limited to Crotalidae (*crotalus* Horridalus), Tarentula *Cubensis* and/or Pyrogen.

Mercurius Solublis can also be known as Hydrargyrum, Mercurius vivus, Argentum vivum, Mercurius Solublis Hahnemanni, Metallic Mercury or Quicksilver. It will also be understood that Mercurius Solubilis may be replaced or complimented with many other mercury containing compounds. For example, *Phytolacca* decandra, also known as Vegetable Mercury, may be used. *Phytolacca* decandra has a high Mercury content and similar inimicable relationship to Mercury as discussed below.

Silica [Sil] can be known under any of its synonyms, such as Silica terra, Silicea terra, Flint, Silex, Silica anhydride, Quartz or Silicon dioxide or may be replaced or complimented with many other silica containing compounds such as Silica Marina Sea Sand.

This homeopathic complex comprising a homeopathic tincture or dilutions thereof of Hepar sulphuris calcareum or other similar profiled *Calcarea* or Sulphur salt or acid;

Lachesis muta or other remedy with a similar profile, such as a spider or snake remedy, Mercurius Solubilis or other mercurius containing remedy with a similar profile (such as *Phytolacca* (vegetable mercury)) and Silica or other silica containing compounds with a similar profile other will be referred to as "Core A" within the specification and examples.

Essentially, Core A provides a general anti-infective homeopathic composition for use in the treatment of general infections and/or sepsis. Core A is essential to all the homeopathic complexes of the present invention. Essentially, Core A functions to allow the abortion, resorption, discharge or absorption of pus formation which develops in association with an infection and/or sepsis/septic infection.

Core A also provides for the re-growth and repair of damaged tissues.

This specific combination of the four homeopathic ingredients in Core A provides general anti-infective activity and is a combination which would not be recommended in most conventional homeopathic literature due to incompatibility of two of the ingredients. However, contrary to conventional teachings, Applicants have found this specific combination is well tolerated and provides good general anti-infective activity.

Specifically, according to general homeopathic teachings Mercurius Solubilis and Silica are incompatible (Remedy Relationships by Thomas Blasig & Peter Vint 1st Ed 2001 Published Hahnemann Institut) Silica Terra (Sil) and Mercurius Solubilis (Merc and Sil) should never be given immediately before or after each other. They are in Homeopathic terms, "inimical" or incompatible (Nature's Materia *Medica*, January 2007 (3rd Edition) (Lotus Materia *Medica* (1st & $2^{rd}$ Edition) Robin Murphy) and Concordant Materia *Medica* (First edition1994) Frans Vermeulen)). Based on classical homeopathic teachings, these ingredients interfere with the action of the other. However, Applicants have surprisingly found that the homeopathic of the present invention uses both these homeopathic ingredients together without any detrimental effect.

Thus, unexpectedly and contrary to conventional homeopathic teachings, Core A advantageously provides for the dual functionality in terms anti-infective activity and re-growth and repair of damaged tissues of the homeopathic complex of the present invention. Thus, using this knowledge it was possible to combine mercury and silica in a way that was beneficial to the patient in need thereof. This has been used to advantage in a broad way in Core A.

Preferably, the homeopathic complex is provided in a potency range from mother tincture to approximately 100M (MM), preferably from mother tincture to 50M (CM) and including LM potencies.

Generally, a "low potency" according to the invention is in the "X" range and is ideally used for topical administration and the treatment of chronic conditions. It may also be used internally to treat the same infection state.

For such topical use "X" or decimal potencies are most appropriate due to their suitability for repeated use on a local area over a period of time, without inducing a homeopathic aggravation. When this homeopathic complex is made in such low potencies up to 18x/9c, preferably from mother tincture to approximately 9c, more preferably from mother tincture to approximately 18x (18x and 9c are roughly equivalent in terms of dilution) it is ideal for topical use, for example as a topical anti-infective cream, gel or liquid healing composition. This comment is applicable to all cores (i.e. Core A and the following Cores) and all combinations of cores. There are some exceptions to this rule for example.

It will be understood that some homeopathic ingredients may be administered as a mother tincture, however, due to Regulatory constraints in some countries, some homeopathic ingredients may not be administered as a mother tincture and must be diluted to 2x, preferably 6x or 8x or higher for administration. A few non-limiting examples include *Aesculus hippocastanum*, Arsenicum Album, Cantharis, *Gelsemium*, Mezereum, Nux Vomica, Phosphorus Staphysagria, Nosodes from the additional Cores C to D would not generally be recommended for used a Mother Tincture because of Regulatory constraints in terms of safety below certain potencies. This is explained in more detail in the various pharmacopeia, for example, the German or American Homeopathic Pharmacopeia.

When this formulation is made in "high potencies" according to the invention, in the C potency range, preferably 30c plus, more preferably 200c plus, it is ideal for internal use, for example as a liquid for oral or internal administration. Thus, at these potencies, the homeopathic complex works as an internal anti-infective healing composition. Again, this comment is applicable to all cores (i.e. Core A and the following Cores) and all combinations of cores. In some situations, there are exceptions to this rule for example, Arsenicum Iod, Hydrastis, Laurocreasus and Gun Powder (which may be used in addition to Core A) can also be used in the low potency range even when formulated for internal administration, as they and other homeopathic ingredients demonstrate significant effects in low potency.

Preferably, "high potency" according to the invention is from about 30c to about 1M.

"Very high potency" according to the invention is generally from about 1M to 10M, and includes LM potencies.

In the "high" to "very high potency" (C or M potency dilution), the Homeopathic works as an acute anti-infective healing composition in situations needed a fast-acting response, for example an anti-infective healing first aid remedy. Thus, when used internally, it will be understood that a high potency in the C range to 1M is generally used for the treatment of acute conditions. The high to very high potencies work best in acute conditions particularly as a complex for first aid treatment from such minor injuries as cuts and grazes to such major events as strokes or traumatic injuries. However, it will also be understood that the general anti-infective composition or mastitis treatment composition of the invention can also be used in high potencies for the internal treatment of infections and/or mastitis.

When the homeopathic composition of the invention is given internally at low potencies, generally speaking Core A causes an abscess to rupture and at high potencies, generally speaking Core A causes an abscess to be absorbed. Applicants have also found that at potencies from approximately 9c to around 30c, so called "medium" potencies (between the low and high potencies), that the homeopathic complex can cause both promote or prevent absorption of the abscess or promote or prevent rupturing.

Thus, the potency of the homeopathic ingredients will generally determine whether it can be applied topically or internally to achieve the best results. This unexpected "biphasic" effect of the composition at different potencies, was observed by the inventors in animals, particularly canines, when the homeopathic composition was administered. At different potencies the homeopathic ingredients work in different ways and should be administered in different ways.

The homeopathic complex according to the present invention can be used as an anti-infective agent in the prophylaxis or treatment of microbial infections.

When used as an anti-infective agent, the homeopathic complex can treat most general microbial infections or sepsis. Advantageously, it has been found that the homeopathic complex according to the present invention can be used in the treatment of Methicillin-resistant *Staphylococcus aureus* (MRSA) or other associated conditions, including other antibiotic resistant bacteria or pathogens. In this manner, the homeopathic complex of the invention can provide the effect of a conventional antibiotic without the many side effects associated with such conventional treatments.

Some non-limiting examples of microbial infections include external microbial infections of the skin, eyes (including conjunctivitis), nails, hoof, ears (including otitis) Some non-limiting examples of microbial infections include internal microbial infections such as mastitis, pneumonia, metritis, joint infections; abscesses acute, chronic, resorptive stage; infected, inflamed or swollen glands.

Additionally, it has been found that the homeopathic complex according to the invention also promotes the regeneration of diseased and/or damaged tissue which includes the re-growth and repair of damaged tissues and/or cells. When used to promote the regeneration of diseased and/or damaged tissue the homeopathic complex can treat multiple conditions. Firstly, the homeopathic complex can treat a multitude of skin conditions including but not limited to general infection, inflammation, pyrexia, wound healing, skin restoration and repair. It can also treat a very wide range of skin disorders such as eczema, purities, sun damage, wrinkles, cracked skin, warts, burns such as sun, heat radiation and chemical burns, piles in humans. Thus, the homeopathic complex can speed the repair/healing of diseased, damaged, wound or incised tissue deriving from wounds, cuts, cracks, grazes, bites, ulcers. Such damaged tissue may be septic, indolent (non-healing), decubitus (bedsores and pressure damaged skin), recurrent or reopening. Furthermore, the homeopathic complex may be used in the treatment of burns including heat, radiation including sun, x-ray treatment and prevention, chemical and/or friction/work blisters. Additionally, the homeopathic complex may be used in tissue regeneration in, for example, grafting such as skin grafting or fracture repair.

The homeopathic complex according to the present invention has many advantageous properties including safety, speed of action, ease of use and efficacy. These advantages are outlined in the Example section below.

The homeopathic complex lacks toxicity and associated side effects. It is well tolerated and is compatible with many conventional pharmaceuticals. It provides for a rapid response time and is highly effective. It can be delivered in multiple formats from topical to oral to parenteral and there are minimal treatment requirements which increase patient compliance and enhancing successful outcomes. Furthermore, it provides for a consistent response and action across all species and across a wide range of conditions or even types of the same condition It will be understood that Core A provides the general anti-infective and/or repair/re-growth activity. However, Core A may be supplemented by the addition of further homeopathic complexes. There are three other general core groups of homeopathic complexes which may be added to Core A to provide for additionally functionality and to improve efficacy. These are homeopathic complexes which will be known as Core B, Core C and Core D throughout the specification and examples. The addition of Cores B to D can increase efficacy and be used to tailor the homeopathic complex to the specific application needed.

Core B ingredients are involved in the promotion of tissue healing.

Ideally Core B comprises a homeopathic tincture or dilutions thereof derived from the following ingredients:
the Ranunculacea family, preferably the Aconite Family or Aconitine, more preferably Aconite napellus [Acon];
the Compositae family, preferably *Arnica montana* [Arn]; *Bellis perennis* [Bell-p];
Calendula Offcinalis [Calen]; *Chamomilla Matricaria* [Cham]; *Millefolium achillea* [Mill];
*Carduus* Marianus; and/or *Echinacea*, preferably *Echinacea angustifolia* [Echi]; *Echinacea purpurea* [Echi-p];
the Solanacea family, preferably *Belladonna* [Bell];
Arsenicum, preferably Arsenicum iodatum [Ars-i] and/or Arsenicum Album;
Bryonia alba [Bry];
*Hamamelis virginiana* [Ham];
*Hypericum* Perforatum [Hyper];
Ledum *palustre* [Led];
*Phytolacca* decandra [Phyt];
The Anacardiacae family preferably *Rhus Toxicodendron* [*Rhus*-T.];
The Rutaceae family preferably *Ruta* Graveolans [*Ruta*];
*Stellaria media* [Stel]; and/or
Symphytum *officinale* [Symph].

According to a preferred embodiment, Core B comprises a homeopathic tincture or dilutions thereof of the following:
Aconite napellus;
*Arnica montana;*
Arsenicum iodatum;
*Belladonna;*
*Bellis perennis;*
Bryonia alba;
*Calendula Officinalis;*
*Echinacea angustifolia;*
Echinacea purpurea;
Hamamelis virginiana;
Hypericum Perforatum;
Ledum *palustre;*
Millefolium achillea;
Phytolacca decandra;
*Rhus Toxicodendron;*
*Ruta* Graveolans; and/or
Symphytum *officinale.*

The combination of the ingredients in Core A and Core B provides a general anti-infective homeopathic composition for use in the treatment of general infections/sepsis.

Optional ingredients which may be included in Core B are *Thuja Occidentalis* [Thuj], *Chamomilla Matricaria* [Cham], *Stellaria media* [Stel] and/or the Sulphurs, preferably Sulphur [Sulph]. A further optional ingredient for Core B is Graphites naturalis [Graph].

Additional ingredients which may be added to Core B are *Urtica urens* [Urt-u] (equivalent to *Urtica dioica*), Apis mellifica [Apis], Umbelliferae preferably *Conium maculatum* [Con] and/or Gunpowder [Gunp].

Core C ingredients function as constitutional modifiers and work for certain types of individuals boosting their response to treatment. For example, Calc Carb boosts the health of large boned heavy often flabby individuals while Phosphorus helps lean thin high energy outgoing individuals. This is particularly important when tailoring the treatment to the treatment of groups e.g. mastitis in a dairy herd will tend toward the lean side while a beef herd would tend toward the heavy side. The skilled homeopathic practitioner would be able to determine the appropriate remedies to administer from the following groups.

Core C comprises constitutional modifiers preferably selected from the following homeopathic tincture or dilutions thereof of:
- The Arsenicums, preferably Arsenicum album [Ars];
- The Barytas and Cabonicums, preferably Baryta carbonica [Bar-c] and/or *Kali* Carbonicum;
- Carbo vegetabilis [Carb-v];
- The Calcareas, preferably *Calcarea* carbonica [Calc]; *Calcarea* fluorica [Calc-f] and/or *Calcarea* phosphorica [Calc-p];
- *Gelsemium sempervirens* [Gels];
- Iodium purum [Iod];
- The Kalis, preferably *Kali* iodatum [*Kali-i*] and/or *Kali* Carbonicum
- Lacs, preferably Lac *caninum* [Lac-c]; Lac vaccinum defloratum (skimmed) and/or Lac Vaccinum (cow);
- Lycopodium *clavatum* [Lyc];
- The Natrums and Muriatricums, preferably Natrum Mur
- Nux vomica [Nux-v];
- Phosphorus, preferably Phosphorus [Phos] and/or Ferrum Phos;
- the Ranunculacea family, preferably *Pulsatilla nigricans* [Puls] and/or
- Staphysagria [Staph];
- *Sabal serrulata* [*Sabal*];
- Sepia succus [September]; and/or
- Zincums preferably Zincum metallicum [Zinc].

Core C may also comprise remedies for severe septic infection selected from a homeopathic tincture or dilutions thereof of Baptisia *tinctoria* [Bapt] and/or Pyrogen [Pyrog].

Core C may also comprise remedies for blood in milk selected from a homeopathic tincture or dilutions thereof of *Bufo* rana [*Bufo*] and/or Ipecacuanha [p].

Core C may also comprise a homeopathic tincture or dilutions thereof of *Astragalus membranaceus* [Astra-mem].

Core D functions as anti-puritic/anti-inflammatory ingredients. When used in combination with any of the other Cores, this care provides additional anti-puritic/anti-inflammatory functionality of the homeopathic core. Core D comprises a homeopathic tincture or dilutions thereof of the following ingredients:
- Adrenalin [Adren];
- *Aesculus hippocastanum* [Aesc];
- Alfalfa;
- Aurums;
- The Antimoniums, preferably Antimonium Tart
- *Berberis Vulgaris;*
- Cactus *Grandiflora;*
- *Caladium* seguinum [Calad];
- Cantharis vesicatoria [Canth];
- *Carduus* Marianus;
- Cocculus *indicus* [Cocc];
- *Chelidonium;*
- China *officinalis;*
- *Chionanthus virginica;*
- Drosera *rotundifolia;*
- Equisetum hyemale;
- Euphrasia:
- Galium Aprine;
- Grindelia (the Compositae family);
- Histaminium (Histamine) [Hist];
- Hydrastis *canadensis* [Hydr];
- *Lappa* Articum (the Compositae family);
- Lavender [Lav-v.];
- *Lobelia inflata;*
- Mezereum [Mez];
- Nitric acid [Nit-ac];
- *Paeonia Officinalis* [Paeon];
- Prednisolone [Predni.];
- *Ranunculus bulbosus* [Ran-b];
- *Rumex crispus* [Rumx];
- Solidago virgaurea;
- Strophantus *hispidus* (the Compositae family);
- *Taraxacum officinale* (the Compositae family);
- *Triticum Repens;*
- The Stannums preferably Stannum Met;
- Thiosinaminum [Thiosin];
- Uva *Ursi;*
- Veratrum Album;
- Cuprum Met; and/or
- Sol [Sol].

Advantageously, Cores D when administered with any or all of Cores A to C can be used as an anti-itch treatment, pile treatment, stroke treatment, wart treatment, scar treatment, anti-wrinkle treatment. Core D may act as an anti-pyretic, anti-inflammatory and/or analgesic. For example, Thiosinaminum [Thiosin] is used to treat scarring (similar to silica and graphites) and Sol [Sol] is used to treat sunburn. Many forms of application may be contemplated. In addition, as with other embodiments of the invention, the potency can be altered depending on the end use.

Furthermore, the homeopathic complex of the present invention, as defined in cores A to D above, may also comprise nosodes. Nosodes are homeopathic remedies that are made from the specific products of a particular disease. This can be tissue containing the actual disease agents or tissue affected by those agents. Sometimes nosodes are made from vaccines containing the organisms. The nosodes are prepared in a diluted and potentized form just like all other homeopathic medicine. There is no potential for an animal to become infected with a given disease agent from a nosode because of the pharmaceutical process that occurs which dilutes and inactivates any viable organisms, particularly when manufactured using the Hahnemannian method and they are used at 30c and above. Nosodes are ideally selected from Tuberculinum bovinum, Tuberculinium aviaire, *Staphylococcus aureus*, Strepococcus, *Corynebacterium, E. Coli*, Colibacillinum, Bacillinum and/or Medorrhinum.

As expanded on above in relation to Core A, an important aspect of the present invention is the potency of the homeopathic complex. Specifically, the homeopathic complex may be provided at different potency levels in order to work in different areas and on different conditions. Thus, changing the potency, by dilution and succession, will give a homeopathic complex with a different mode of action. Thus, a significant advantage of the present invention is that both the homeopathic ingredients of Cores A to D can be combined in different ways and the potency can be altered. Different combinations of Cores and different potencies will result in a homeopathic complex used for different conditions.

The invention will now be described in relation to specific embodiments of the invention and their end uses.

According to a one specific embodiment of the invention, there is provided a general anti-infective homeopathic composition comprising a homeopathic tincture or dilutions thereof of: Hepar Sulph, Lachesis, Merc, Sil; and
Aconite napellus; *Arnica montana*; Arsenicum iodatum; *Belladonna; Bellis perennis*; Bryonia alba; Calenula Offcinalis; *Chamomilla Matricaria; Echinacea angustifolia;*

*Echinacea purpurea*; Graphites naturalis; *Hamamelis virginiana*; *Hypericum* Perforatum; Ledum *palustre*; *Millefolium achillea*; *Phytolacca* decandra; *Rhus Toxicodendron*; *Ruta* Graveolans; *Stellaria media*; Sulphur; Symphytum *officinale*; and *Thuja Occidentalis*.

Thus, the general anti-infective healing composition comprises a homeopathic tincture or dilutions thereof of Core A, Core B, Graphites, Sulphur, *Thuja, Chamomilla* and *Stellaria*.

The following table outlines suitable potency ranges for each of the ingredients when used in a topical general anti-infective healing formulation.

It will also be understood that some homeopathic ingredients may be administered as a mother tincture, however, as explained before, for Regulatory reasons in some countries some homeopathic ingredients may not be administered as a mother tincture and must be diluted to 2×, preferably 6× or 8× or higher for administration. These are indicated on the table below.

| Remedy | [Short form] | Preferred Range for Topical Use | Example Potency | Effective Final dilution in Cream |
|---|---|---|---|---|
| Hepar Sulphuris | [Hep-s] | Range 2x-12x/6c | 3x* | 4x |
| Lachesis | [Lach] | Range 8x-12x/6c | 8x | 9x |
| Mercurius Solubilis | [Merc-s] | Range 6x-12x/6c | 6x | 7x |
| Silica | [Sil] | Range 2x-12x/6c | 3x* | 4x |
| Aconitum Napellus | [Acon] | Range 2x-12x/6c | 3x* | 4x |
| Arnica Montana | [Arn] | Range MT-12x/6c | 3x* | 4x |
| Arsenicum Iod | [Ars-i] | Range 6x-12x/6c | 6x | 7x |
| Belladonna | [Bell] | Range 2x-12x/6c | 3x* | 4x |
| Bellis Perenis | [Bell-p] | Range MT-12x/6c | 3x* | 4x |
| Bryonia Alba | [Bry], | Range MT-12x/6c | 3x* | 4x |
| Calenula Offcinalis | [Calen] | Range MT-12x/6c | 3x* | 4x |
| Chamomilla Matricaria | [Cham] | Range MT-12x/6c | 3x* | 4x |
| Echinacia augustifolia | [Echi-a] | Range MT-12x/6c | 3x* | 4x |
| Echinacia Purpurea | [Echi-p] | Range MT-12x/6c | 3x* | 4x |
| Graphites naturalis | [Graph] | Range 8x-12x/6c | 8x | 9x |
| Hamamellis Virginiana | [Ham] | Range MT-12x/6c | 3x* | 4x |
| Hypericum Perforatum | [Hyper] | Range MT-12x/6c | 3x* | 4x |
| Ledum | [Led] | Range MT-12x/6c | 3x* | 4x |
| Millefolium | [Mill] | Range MT-12x/6c | 3x* | 4x |
| Phytolacca | [Phyt] | Range 6x-12x/6c | 6x | 7x |
| Rhus Toxicodendron | [Rhus-t] | Range MT-12x/6c | 3x* | 4x |
| Ruta Graveolans | [Ruta] | Range MT-12x/6c | 3x* | 4x |
| Stellaria Media | [Stel] | Range MT-12x/6c | 3x* | 4x |
| Sulphur** | [Sulph] | Range MT-12x/6c | 4x | 4x |
| Symphytum | [Symph] | Range MT-12x/6c | 3x* | 4x |
| Thuja Occidentalis | [Thuja] | Range MT-12x/6c | 3x* | 4x |

*these potencies are ideal for use in the USA. Some minor adjustments to the potencies may be needed for Europe where for Regulatory reasons 3x potencies require additional tests and must be 4x or higher for simplified registrations. Again, this will largely be determined in the country of interest based on Regulatory constraints.

**As stated above, Sulphur for example is not soluble below 4x but can be mixed into a cream as sulphur powder that has been titurated with lactose to form a titurate. Arsenicum Iod, Sulphur, Silica, Graphite and Hepar Sulp are also insoluble and form titurates not tinctures. *Lachesis* is best prepared initially in glycerine (to preserve the protein activity of the venom) as it can be denatured by both alcohol and lactose.

Optional ingredients which may be included are *Conium maculatum* and/or Gunpowder (depending on Regulatory constraints).

Each ingredient is ideally present from 0.1 to 20% v/v based on the volume of the total composition. Ideally, each ingredient is present in equal ratios/proportions.

Ideally, the potency of each ingredient is in the low potency range from mother tincture to approximately 18×/9c, preferably 12×/6c. This potency is ideal for topical administration, in the form of for example, a topical cream, gel or liquid. Optionally, this homeopathic composition may be given in a high potency and used internally as a general anti-infective healing composition. Applicants have found the best effects are when the composition is adminstered in low potency for administration.

According to a preferred embodiment, this homeopathic composition is formulated as a topical cream. A non-active base is ideally used, comprising lanolin, petroleum and mineral oil. Such as base could comprise, for example, approximately 15 to 35%, preferably 25% lanolin, approximately 40 to 60%, preferably 50% petroleum with 15 to 25%, preferably 25% mineral oil and would be ideal for use in cold climates. It will be appreciated that any other non-active bases known may be used.

According to this embodiment of the invention, to make an anti-infective cream, each ingredient is made according to the potency range above and this is done by different methods depending on whether it is a tincture or titurate. A titurate refers to the insoluble homeopathic ingredients, such as Arsenicum Iod, Sulphur, Silica, Graphite, Hepar Sulp, Lachesis etc, which are diluted and potentised by grinding with lactose. A tincture is as defined previously and is diluted and potentised in the usual manner by sucussion in an alcohol and water premix. The tincture and titurates are then combined with each other and the base cream. These comments about tincture and titurates are relevant to all embodiments/compositions of the invention.

Each ingredient is ideally combined in equal proportions in a non-active cream base. Ideally, the combined ingredients are combined with the cream from approximately 1 to 10% w/v based on the total weight of the final homeopathic composition. Preferably, the combined ingredients are combined with a cream at from 3 to 6% w/v based on the total weight of the final homeopathic composition.

According to a more specific embodiment of the invention, there is provided a general anti-infective homeopathic composition which can be used in the treatment of mastitis.

Mastitis is initially caused by microbial infection through damaged skin. In particular, mastitis has a tremendous economic importance for the dairy industry as the present antibiotic therapies reduce usable milk yield. Thus, alternative therapies to conventional antibiotic therapies are under evaluation. Common causal microorganisms found in mastitis include:

Staphylococcus aureus;
Staphylococcus albus;
Streptococcus species e.g. agalactia, uberis, dysgalactia;
Escherichia coli;
Salmonella species;
Mycobacterium tuberculosis; and/or
Fungal mastitis e.g. Candida albicans and Cryptococcus neoformans.

Such a mastitis treatment ideally comprises a homeopathic tincture or dilutions thereof of: Hepar Sulphuris Calcareum, Lachesis, Merc Sol, Silicea; and Aconitum Napellus, Arnica Montana, Arsenicum Iod, Belladonna, Bellis Perenis, Bryonia Alb, Calenula Offcinalis, Chamomilla Matricaria, Conium maculatum, Echinacia augustifolia, Echinacia Purpurea, Graphites, Hamamellis Virginia, Hypericum Perforatum, Ledum, Millefolium, Phytolacca decandra, Ruta Graveolans, Rhus Toxicodendron, Stellaria Media, Sulphur, Symphytum, Urtica Urens and Thuja Occidentalis.

Essentially, this mastitis treatment comprises Core A and Core B plus Chamomilla Matricaria, Stellaria Media, Graphites, Sulphur and Thuja, Conium and Urtica.

Gunpowder is an optional homeopathic ingredient for this homeopathic composition and its use depends on Regulatory constraints in the applicable country.

The homeopathic complex of the present invention may be use to treat elevated Somatic Cell Counts, to prevent Mastitis and in the treatment of mammary hypertrophy and other hypertrophic conditions.

Again, each ingredient is ideally present from 0.1 to 20% v/v based on the volume of the total composition. Ideally, each ingredient is present in equal ratios/proportions.

Ideally, the potency of each ingredient is in the low potency range from mother tincture to approximately 18x/9c, preferably 12x/6c. This potency is ideal for topical administration, in the form of for example, a topical cream, gel or liquid. Optionally, this homeopathic composition may be given in a high potency and used internally as a mastitis treatment composition. Applicants have found the best effects are when the composition is administered in low potency for administration.

According to a preferred embodiment, this homeopathic composition is formulated as a topical cream. A non-active base is ideally used, comprising lanolin, petroleum and mineral oil. Such as base could comprise, for example, approximately 15 to 35%, preferably 25% lanolin, approximately 40 to 60%, preferably 50% petroleum with 15 to 25%, preferably 25% mineral oil and would be ideal for use in cold climates. It will be appreciated that any other non-active bases known may be used.

The following table outlines suitable potency ranges for each of the ingredients when used in a topical formulation for mastitis treatment.

| Remedy | Preferred Potency Range for Topical Use | Preferred Potency | Effective Final dilution in Cream |
|---|---|---|---|
| Hepar Sulphuris | 2x-12x/6c | 3x* | 4x |
| Lachesis | 8x-12x/6c | 8x | 9x |
| Mercurius Solubilis | 6x-1x/6c | 6x | 7x |
| Silica[Sil] | 2x-1x/6c | 3x* | 4x |
| Aconitum Napellus | 2x-12x/6c | 3x* | 4x |
| Arnica Montana | MT-12x/6c | 3x* | 4x |
| Arsenicum Iod | 6x-12x/6c | 6x | 7x |
| Belladonna | 2x-12x/6c | 3x* | 4x |
| Bellis Perenis | MT-12x/6c | 3x* | 4x |
| Bryonia Alb | MT-12x/6c | 3x* | 4x |
| Calenula Offcinalis | MT-12x/6c | 3x* | 4x |
| Chamomilla Matricaria | MT-12x/6c | 3x* | 4x |
| Conium maculatum | MT-12x/6c | 8x | 9x |
| Echinacia augstofolia | MT-12x/6c | 3x* | 4x |
| Echinacia Purpurea | 8x-12x/6c | 3x* | 4x |
| Graphites | MT-12x/6c | 8x | 9x |
| Gunpowder | MT-12x/6c | 3x* | 4x |
| Hamamellis Virginia | MT-12x/6c | 3x* | 4x |
| Hypericum Perforatum | MT-12x/6c | 3x* | 4x |
| Ledum | 6x-12x/6c | 3x* | 4x |
| Millefolium | MT-12x/6c | 3x* | 4x |
| Phytolacca decandra | 6x-12x/6c | 6x* | 7x |
| Ruta Graveolans | MT-12x/6c | 3x* | 4x |
| Rhus Toxicodendron | MT-12x/6c | 3x* | 4x |
| Stellaria Media | MT-12x/6c | 3x* | 4x |
| Sulphur** | MT-12x/6c | 3x* | 4x |
| Symphytum | MT-12x/6c | 3x* | 4x |
| Thuja Occidentalis | MT-12x/6c | 3x* | 4x |
| Urtica Urens | MT-200c | 30c | 30c |

*these potencies are ideal for use in the USA. Some minor adjustments to the potencies may be needed for Europe where for Regulatory reasons 3x potencies require additional tests and must be 4x or higher for simplified registrations. Again, this will largely be determined in the country of interest based on Regulatory constraints.
**As stated above, Sulphur for example is not soluble below 4x but can be mixed into a cream as sulphur powder that has been titurated with lactose to form a titurate. Arsenicum Iod, Sulphur, Silica, Graphite and Hepar Sulp are also insoluble and form titurates not tinctures. Lachesis is best prepared initially in glycerine (to preserve the protein activity of the venom) as it can be denatured by both alcohol and lactose.

Optionally, nosodes from Tuberculinum bovinum, Tuberculinium aviaire, Staphylococcus aureus, Strepococcus, Streptococcus uberis Corynebacterium, E. Coli, Colibacillinum, Bacillinum and/or Medorrhinum may be used. Ideally, such nosodes are present in a potency range from 6x to 1M, preferably from approximately 6x-12x/6c. It will be understood that any nosode of any pathogen or pathological material including those involved in the condition to be treated may be used.

A further anti-infective mastitis treatment comprising Core A; Core B plus Stellaria media, Chamomilla matriaca, Sulphur and conium; and Core C without Arsenicum album, Gelsemium, Lac vaccinum and Staphlysagria. Ferrum Phos, Natrum Mur, Kali Carbonicum. This mastitic treatment was used in Example 10

| REMEDY | PREFERRD POTENCY RANGE | PREFERRED POTENCY | PREFERRED CONCENTRATION RANGE | CONCENTRATION Vol/Vol % |
|---|---|---|---|---|
| Aconitum napellus | 4x TO12C | 6C | .1 to 20% | 1.15% |
| Aconitum napellus | 12c TO 197c | 30C | .1 to 20% | 1.15% |
| Aconitum napellus | 198c TO 10M | 200C | .1 to 20% | 1.15% |
| Apis Mel 6c | 6C TO 1M | 6C | .1 to 20% | 0.69% |

-continued

| REMEDY | PREFERRD POTENCY RANGE | PREFERRED POTENCY | PREFERRED CONCENTRATION RANGE | CONCENTRATION Vol/Vol % |
|---|---|---|---|---|
| *Arnica Montana* | 6x TO 27C | 6C | .1 to 20% | 0.69% |
| *Arnica Montana* | 27c TO 1M | 30C | .1 to 20% | 0.69% |
| *Astragalus* | 6x TO 27C | 6C | .1 to 20% | 0.69% |
| *Astragalus* | 27c TO 1M | 30C | .1 to 20% | 0.69% |
| Arsencium Iod | 6x to 24x/12c | 8x | .1 to 20% | 0.69% |
| *Baptista* | 27c TO 1M | 30C | .1 to 20% | 1.15% |
| *Belladonna* | 6c TO 100c | 30c | .1 to 20% | 2.29% |
| *Belladonna* | 101c TO 997C | 200c | .1 to 20% | 2.29% |
| *Belladonna* | 998C to 9997C | 1M | .1 to 20% | 2.29% |
| *Bellis Perenis* | 6x TO 27C | 6C | .1 to 20% | 1.15% |
| *Bellis Perenis* | 27c TO 1M | 30C | .1 to 20% | 1.15% |
| *Bryonia* | 4x TO 12C | 6C | .1 to 20% | 2.29% |
| *Bryonia* | 12c TO 197c | 30C | .1 to 20% | 2.29% |
| *Bryonia* | 198c TO 10M | 200C | .1 to 20% | 2.29% |
| *Bufo* | 6x TO 27C | 6C | .1 to 20% | 0.69% |
| *Bufo* | 27c TO 1M | 30C | .1 to 20% | 0.69% |
| Calc Carb | 6x TO 27C | 6C | .1 to 20% | 1.15% |
| Calc Carb | 27c TO 1M | 30C | .1 to 20% | 1.15% |
| Calc Phos | 6x TO 27C | 6C | .1 to 20% | 1.15% |
| Calc Phos | 27c TO 1M | 30C | .1 to 20% | 1.15% |
| Calc Fluor | 6x TO 27C | 6C | .1 to 20% | 0.69% |
| Calc Fluor | 27c TO 1M | 30C | .1 to 20% | 0.69% |
| *Calendula* 6c | 6x TO 1M | 6C | .1 to 20% | 0.69% |
| Carbo Veg | 6x TO 27C | 6C | .1 to 20% | 2.29% |
| Carbo Veg | 27c TO 1M | 30C | .1 to 20% | 2.29% |
| *Chamomilla* | 6x TO 27C | 6C | .1 to 20% | 0.69% |
| *Chamomilla* | 27c TO 1M | 30C | .1 to 20% | 0.69% |
| *Conium* | 6x TO 27C | 6C | .1 to 20% | 0.69% |
| *Conium* | 27c TO 1M | 30C | .1 to 20% | 0.69% |
| *Echinacea Angustifolia* | 6C TO 1M | 6C | .1 to 20% | 0.69% |
| *Echinacea purpurea* | 6C TO 1M | 6C | .1 to 20% | 0.69% |
| *Hammamelis* | 6x TO 1M | 30c | .1 to 20% | 0.69% |
| Hepar Sulph | 30C TO 200C | 200c | .1 to 20% | 2.29% |
| Hepar Sulph | 201C to 9997C | 1M | .1 to 20% | 2.29% |
| Hepar Sulph | 9999C TO 50M | 10M | .1 to 20% | 2.29% |
| *Hypericum* | 6x TO 27C | 6C | .1 to 20% | 0.69% |
| *Hypericum* | 27c TO 1M | 30C | .1 to 20% | 0.69% |
| Iodium | 6x TO 27C | 6C | .1 to 20% | 0.69% |
| Iodium | 27c TO 1M | 30C | .1 to 20% | 0.69% |
| Ipecac | 6x TO 27C | 6C | .1 to 20% | 0.69% |
| Ipecac | 27c TO 1M | 30C | .1 to 20% | 0.69% |
| Kali Iod | 6x TO 1M | 6C | .1 to 20% | 0.69% |
| Lac Caninum | 6x TO 1M | 30c | .1 to 20% | 2.29% |
| Lac Bovinum | 6x TO 1M | 30c | .1 to 20% | 2.29% |
| *Lachesis* | 6x to 12c/24x | 6c | .1 to 20% | 1.15% |
| *Lachesis* | 12c TO 197c | 30c | .1 to 20% | 1.15% |
| *Lachesis* | 198c TO 10M | 200c | .1 to 20% | 1.15% |
| *Ledum* | 6x TO 27C | 6C | .1 to 20% | 0.69% |
| *Ledum* | 27c TO 1M | 30C | .1 to 20% | 0.69% |
| *Lycopodium* | 6x TO 27C | 6C | .1 to 20% | 0.69% |
| *Lycopodium* | 27c TO 1M | 30C | .1 to 20% | 0.69% |
| Merc Sol | 30C TO 200C | 200c | .1 to 20% | 1.15% |
| Merc Sol | 201C to 9997C | 1M | .1 to 20% | 1.15% |
| Merc Sol | 9999C TO 50M | 10M | .1 to 20% | 1.15% |
| *Nux Vomica* | 6x TO 27C | 6C | .1 to 20% | 0.69% |
| *Nux Vomica* | 27c TO 1M | 30C | .1 to 20% | 0.69% |
| Phosphorus | 6x TO 1M | 30c | .1 to 20% | 1.15% |
| *Phytolacca decandra* | 6x to 12c/24x | 6c | .1 to 20% | 2.29% |
| *Phytolacca decandra* | 12c TO 197c | 30c | .1 to 20% | 2.29% |
| *Phytolacca decandra* | 198c TO 10M | 200c | .1 to 20% | 2.29% |
| *Pulsatilla* | 6x TO 1M | 30c | .1 to 20% | 1.15% |
| Pyrogen | 30C TO 10M | 1M | .1 to 20% | 1.15% |
| *Rhus toxicodendron* | 6x to 12c/24x | 6c | .1 to 20% | 0.69% |
| *Rhus toxicodendron* | 12c TO 197c | 30c | .1 to 20% | 0.69% |
| *Rhus toxicodendron* | 198c TO 996c | 200c | .1 to 20% | 0.69% |
| *Rhus toxicodendron* | 997C TO 9997C | 1M | .1 to 20% | 0.69% |
| *Ruta Grav* | 6x to 12c/24x | 6c | .1 to 20% | 0.69% |
| *Ruta Grav* | 12c TO 197c | 30c | .1 to 20% | 0.69% |
| *Ruta Grav* | 198c TO 10M | 200c | .1 to 20% | 0.69% |
| *Sabal* | 6x TO 27C | 6C | .1 to 20% | 0.69% |
| *Sabal* | 27c TO 1M | 30C | .1 to 20% | 0.69% |
| *Sepia* | 6x TO 27C | 6C | .1 to 20% | 0.69% |
| *Sepia* | 27c TO 1M | 30C | .1 to 20% | 0.69% |
| Silica | 6c TO 100c | 30c | .1 to 20% | 2.29% |
| Silica | 101c TO 997C | 200c | .1 to 20% | 2.29% |

| REMEDY | PREFERRD POTENCY RANGE | PREFERRED POTENCY | PREFERRED CONCENTRATION RANGE | CONCENTRATION Vol/Vol % |
|---|---|---|---|---|
| Silica | 998C TO 9997C | 1M | .1 to 20% | 2.29% |
| *Stellaria Media* | 6x TO 1M | 30c | .1 to 20% | 0.69% |
| Suphur | 6x TO 1M | 30c | .1 to 20% | 2.29% |
| *Symphytum* | 6x TO 1M | 30c | .1 to 20% | 0.69% |
| *Urtica* | 6x TO 1M | 30c | .1 to 20% | 0.69% |
| Zincum Met | 4x TO 12C | 4c | .1 to 20% | 0.69% |
| Zincum Met | 6x TO 1M | 30c | .1 to 20% | 0.69% |
| | | | | 100.00% |

The composition as defined above is ideal for internal use and is in the C potency range. Ideally, this homeopathic composition is in a form suitable for internal use, for example a liquid with excipients being alcohol and water.

Optionally, nosodes are combined with this homeopathic mastitis treatment composition.

Suitable nosodes are outlined in the following table.

| NAME OF REMEDY | PREFERRED POTENCY RANGE | EXAMPLE POTENCY | CONCENTRATION Vol/Vol % RANGE |
|---|---|---|---|
| *Tuberculinum Bovinum* | 30C TO 1M | 30c | .1% TO 20% |
| *Tuberculinium Aviaire* | 30C TO 1M | 30c | .1% TO 20% |
| *Staphylococcus Aureus* | 30C TO 1M | 30c | .1% TO 20% |
| *Strepococcus* | 30C TO 1M | 30c | .1% TO 20% |
| *Strepococcus* Mix | 30C TO 1M | 30c | .1% TO 20% |
| *Corynebacterium* | 30C TO 1M | 30c | .1% TO 20% |
| *E. Coli* (ColibacillinuM) | 30C TO 1M | 30c | .1% TO 20% |
| *E. Coli* | 30C TO 1M | 200c | .1% TO 20% |
| *Bacillinum* | 30C TO 1M | 30c | .1% TO 20% |
| *Medorrhinum* | 30C TO 1M | 30c | .1% TO 20% |

Ideally, the nosodes are added in equal proportions/ratios.

According to another embodiment of this aspect of the invention, an effective mastitis treatment comprises the use of the homeopathic composition defined above for internal use administered concurrently with the previously defined topical mastitis treatment.

According to a more specific embodiment of the invention, there is provided a general anti-infective homeopathic composition used in the treatment of trauma or shock comprising a homeopathic tincture or dilutions thereof of the following ingredients:

Hepar Sulphuris Calcareum, Lachesis, Merc Sol, Silicea; and
Aconite;
Arsencium Iod;
*Arnica Montana;*
Apis;
*Belladonna;*
Bellis Perennis;
Bryonia;
Calendula;
Cantharis;
Carbo Veg;
Crategus;
*Echinacea Augustifolia;*
Echinacea Purpura;
Ferrum Phos;
*Gelsemium;*
Hammamellis;
*Hypericum;*
Laurocerasus;
Ledum;
*Millefolium;*
Nux Vomica;
*Phytolacca;*
*Rhus* Tox;
*Ruta* Grav;
Symphytum; and
Staphysagria.

Essentially, this homeopathic composition comprises Core A; Core B with *Chamomilla matricaria* and *Stellaria media*, Sulphur, Apis and *Urtica*; Core C ingredients Carbo veg, *Gelsemium*, Nux Vomica and Phos; and Cantharis, *Laurocerasus*, Crategus and Ferrum phos. The following table outlines suitable potency ranges for each of the ingredients.

| REMEDY | Preferred Range | Preferred Potency |
|---|---|---|
| Aconite | 30C-10M | 1M |
| Apis | 30C-10M | 1M |
| Arnica Montana | 30C-10M | 1M |
| Arsencium Iod | 6x to 24x/12c | 8x |
| *Belladonna* | 30C-10M | 1M |
| *Bellis Perennis* | 30C-10M | 1M |
| *Bryonia* | 30C-10M | 1M |
| Calendula | 30C-10M | 1M |
| Cantharis | 30C-10M | 1M |
| Carbo Veg | 30C-10M | 1M |
| Causticum | 28C TO 10M | 30c |
| *Conium* | 28C TO 10M | 30c |
| Crategus | MT-24x/12c | 4x |
| *Echinacea Anugustifolia* | 30C-10M | 1M |
| *Echinacea Purpura* | 30C-10M | 1M |
| Ferrum Phos | 6x to 24x/12c | 12x |
| Gelsemium | 30C-10M | 1M |
| *Hammamellis* | 30C-10M | 1M |
| Hepar Sulph | 30C-10M | 1M |
| *Hypericum* | 30C-10M | 1M |
| Lachesis | 30C-10M | 1M |
| Laurocerasus | MT-24x/12c | 4x |
| Ledum | 30C-10M | 1M |
| Merc Sol | 30C-10M | 1M |
| *Millefolium* | 30C-10M | 1M |
| *Nux Vomica* | 30C-10M | 1M |
| Phosphorus | 30C-10M | 200c |
| *Phytolacca* | 30C-10M | 1M |
| *Rhus Tox* | 30C-10M | 1M |
| *Ruta Grav* | 30C-10M | 1M |
| Silica | 30C-10M | 1M |
| Sulphur | 6x-10m | 30c |
| *Staphysagria* | 30C-10M | 1M |
| *Symphytum* | 30C-10M | 1M |
| *Urtica* | 28C TO 10M | 30c |
| *chamomilla matrica* | 30-10m | 1m |
| *stellaria* | 28c-10m | 30c |

Ideally, this homeopathic composition is in a form suitable for internal use, for example a liquid with excipients being alcohol and water.

The homeopathic ingredients are combined from approximately 0.1 to 20% v/v based on the total volume of the final homeopathic composition. Each ingredient is ideally combined in approximate equal proportions (1:1 ratio) in the liquid excipient.

It will be understood that the homeopathic complexes of the present invention may be used in the both human medical and veterinary applications and are trans-species in action. Indeed, as shown in the Examples, the homeopathic complexes work in a wide variety of species, from companion animal (e.g. canines, felines to exotic parrot etc) to farm animals (e.g. equines and bovines etc) and to humans to name a few.

It will be understood that the general mode of action common to all the homeopathic complexes of the present invention, is the treatment of microbial infections and/or the repair and re-growth of damaged cells or tissue.

Specific applications of the homeopathic composition according to the invention, include but are not limited to treatment of the following conditions:
Wound treatment;
Fracture treatment;
Dermatitis, including photo-dermatitis;
Sun burn;
MRSA Infection;
Mastitis;
Stroke;
Pneumonia;
Hepatitis;
Nephritis; and/or
Detoxification.

Some specific non-limiting uses of the homeopathic complex are outlined as follows. The homeopathic complex may be used in the treatment of various skin conditions including eczema and the like. Advantageously, Applicants have found that scars are either prevented or minimized. Thus, the homeopathic complex may be used as a scar treatment.

The homeopathic complex may also be used in the treatment of mastitis, both acute and chronic. Mastitis is a widespread condition in many animals, in particular cattle. Conventional treatments for mastitis involve the use of antibiotics which is not desirable for commercial milk production. Any treatment which results in the reduction of the use of antibiotics would be advantageous for commercial milk production in cows. Thus, the generation of a new therapy for the treatment of mastitis which does not involve antibiotics is desirable.

The homeopathic complex may also be used for detoxification and such a composition would generally comprise Core A and some of Cores B, C and D.

According to another aspect of the present invention, the homeopathic complex can be used as a cosmetic skin preparation. For example it may be used as an anti-wrinkle cream in the repair and or regeneration of skin cells.

Ideally, the homeopathic complex is manufactured according to a competent homeopathic pharmacopeia such as the German, US, UK, EU and/or French Homeopathic Pharmacopeias. Preferably, the homeopathic complexes are provided in a potency range from 1× to 12×, more preferably from 3× to 12× for the purposes of analytical traceability (Churchill Livingstone's International Dictionary of Homeopathy Edited by Jeremy Swayne (2000) page 193, 1st Edition). Although, it will be understood that any potency from homeopathic tincture upwards can be used provided that the dangers of toxicity with very low potencies or tinctures are managed and all Official Regulatory conditions are met.

Homeopathic complexes are generally prepared in liquid carrier solutions (as a tincture) but may also be extracted in, for example, lactose by trituration and may thereafter be prepared in various delivery forms. For example, the extracted material of the homeopathic ingredient may be extracted in liquid form, using an alcohol and water solvent. This is then followed by comminution, percolation, maceration and squeezing techniques. When extracted in liquid form the resulting solution can contain anywhere from one part drug to three parts mother tincture although this strength can vary from 10 to 50% depending on the monograph used. What makes a tincture truly homeopathic is the additional dilution process to where the final tincture represents a dilution of 1:10 of the drug in effect a 1× dilution. Titurates of insoluble homeopathic ingredients may also be made. Extraction of the homeopathic ingredient by tituration may take place using lactose to result in a solid or powder extract done up to 3c or third centesimal dilution. The homeopathic tincture or titurate may then be combined with a base for use as a topical preparation or be used directly as a liquid oral preparation. Alternatively, it may be sprayed or impregnated onto various solid mediums, such as a tablet.

All the complexes according to the present invention may be used for topical including eye drops, oral, transdermal, implanted, suppository, or parenteral administration in a wide variety of forms such as gels, spray, liquids, powders, tablets, pillules, lotions, liniments, ointments to give just some examples. It will be understood that the homeopathic complex is made in the usually homeopathic manner according to homeopathic guidelines. It may then be administered as it is, or as a homeopathic dilution thereof. It may be administered in different ways by combining the complex with a delivery means, such as a cream or spray for topical use or a tablet for oral administration etc.

According to one specific embodiment of this aspect of the invention the homeopathic complex is in the form of an oral preparation, such as a dry dose form including a powder or tablet. Preferably, the homeopathic complex is provided in the form of a dosage unit form selected from a group consisting of tablets, capsules, pellets, gel caps, pills, pillules, globules, granules, crystals and suppositories. For example, tablets comprising lactose and sucrose may be used.

Alternatively, the homeopathic complex according to this aspect of the invention may be in the form of a liquid preparation, such as a syrup or paste, spray or drops. Delivery of the liquid preparations may be in the form of injections, eyedrops, eardrops, nasal sprays, inhalers or diffusers.

According to another embodiment of this aspect of the invention the homeopathic complex may be in the form of a topical preparation such as an ointment, cream, lotion, oil, liniment, liquid and gel, such as a hydrophilic ointment.

Daily to twice or thrice administration of the homeopathic complex for a period of days is contemplated. It may be applied topically as needed, orally for daily dosage in unit dosage form or in liquid drops.

Conventional pharmaceutical excipients or cosmetic excipients suitable for the deliver system used can have the homeopathic complex incorporated into them or the homeopathic complex can be applied to the end product or packaged with the end product.

Pharmaceutical excipients are substances other than the pharmacologically active drug or prodrug which are included in the manufacturing process or are contained in a finished pharmaceutical product dosage form. They are classified by the functions they perform in a pharmaceutical dosage form. Principal excipient classifications or functions include, but are not limited to the following:

Binders;
Disintegrants;
Fillers (diluents);
Lubricants;
Glidants (flow enhancers);
Compression aids;
Colors;
Sweeteners;
Preservatives;
Suspending/dispersing agents;
Film formers/coatings; and/or
Flavors.

Some, for example, comprise the product's delivery system. These transport the active drug to the site in the body where the drug is intended to exert its action. Others will keep the drug from being released too early in the assimilation process in places where it could damage tender tissue and create gastric irritation or stomach upset. Others help the drug to disintegrate into particles small enough to reach the blood stream more quickly and still others protect the product's stability so it will be at maximum effectiveness at time of use. In addition, some excipients are used to aid the identification of a drug product. Last, but not least, some excipients are used simply to make the product taste and look better. This improves patient compliance, especially in children. Although technically "inactive" from a therapeutic sense, pharmaceutical excipients are critical and essential components of a modern drug product. In many products, excipients make up the bulk of the total dosage form.

Ideally this formulation is provided in a form suitable for topical administration. As such, it may be delivered as a topical cream, lotion, gel, ointment, liniment, eyedrops, spray, skin patch/dressing or combined with a conventional topical medication or skin treatment. For topical administration, the homeopathic formulation can be combined into any commercially available base. For examples, the base may comprise approximately Lanolin from approximately 15 to 35%, preferably 25%

Mineral oil from approximately 15 to 35%, preferably 25%

Petroleum from approximately 40 to 60%, preferably 50% at 2 oz/lb.

Alternatively the base may be a silcox base or a non-lanolin non-mineral oil aqueous cream.

In addition, the homeopathic complex may be administered as a combination therapy, for example, at the same time as a conventional pharmaceutical, e.g. antibiotic, nutritional supplement or food.

In this specification the term "pharmaceutical" or "pharmaceutical composition" covers any chemical or biological substance, synthetic or non-synthetic which when taken by a subject will alter the function of that subject. Such substances ideally are intended for use in the treatment or prevention of disease in man or other animals. As such this term encompass more that conventional drugs or medicines and can also cover food, medicines, vitamins and minerals in general. Furthermore, the term "pharmaceutical" also the substance however it is made and, as such, encompasses biopharmaceuticals, biotechnology-derived treatments (including gene therapy) and phytotherapies.

In this specification the term "combination therapy" is used broadly to cover the simultaneous administration of the homeopathic complex and the pharmaceutical composition. As such, the homeopathic tincture may be packaged separately to the pharmaceutical composition which is provided with a set of instructions for co-administration. The term "combination therapy" also covers the combination of the homeopathic complex with the pharmaceutical composition as a single entity. In this way, the homeopathic complex may be combined or integrated with the pharmaceutical composition during or after manufacture. For example, the homeopathic complex when in liquid form may be sprayed onto the pharmaceutical composition. Alternatively, the homeopathic complex may be provided in liquid or powder form and may simply be combined or mixed with the pharmaceutical composition during manufacture. In this manner, the pharmaceutical composition acts as a delivery system for the homeopathic composition.

The co-administration of a conventional drug and a homeopathic according to the invention goes against Classical Homeopathic teachings and techniques. According to Classical/conventional homeopathic teachings, homeopathic complexes must be taken on their own at least 20 minutes after ingesting any food or drink. On the contrary the present invention dictates that the homeopathic complex is either part of a combination therapy or co-administered with a pharmaceutical composition. This would not be expected in the field of classical homeopathy.

According to another aspect of the invention, there is provided a homeopathic complex of the invention for use in therapy.

Ideally, the homeopathic complex of the invention is for use in the treatment or prophylaxis of infection as an anti-infective agent. Specifically, the homeopathic complex of the invention may be used in the treatment of mastitis. Specifically, the homeopathic complex may be used in the treatment or prophylaxis of MRSA and other type of multi-resistant infections. Additionally, the homeopathic complex of the invention may be used in the regeneration of diseased or damaged tissue. In addition, the homeopathic complex of the invention may be used in the treatment of skin conditions, including acne, general infection, inflammation, pyrexia, wound healing, skin restoration and repair and skin disorders including eczema, puritis, sun damage, wrinkles, cracked skin warts, burns such as sun, heat and radiation burns and/or piles. The homeopathic complex of the invention may be used in the treatment of a stroke or as a first aid remedy.

According to another aspect of the invention, there is provided a method for the manufacture of a medicament comprising the homeopathic complex of the invention for use in the treatment or prophylaxis of infection and/or the regeneration of diseased or damaged tissue. According to yet another aspect of the present invention there is provided a method for the treatment or prophylaxis of infection and/or the regeneration of diseased or damaged tissue in a subject comprising the steps of administering an effective amount of a homeopathic complex of the invention claimed to a patient in need of such treatment.

The invention will now be described by reference to the following non-limiting figures and examples.

EXAMPLES

General Methodology

The general methodology in the following examples, in particular in examples 1 to 9, was to select patients where recovery was not expected despite having been treated with conventional treatments and there was no other conventional treatment to use. Thus, patients who received the homeopathic compositions according to the invention were selected as described on the basis of a non-response to conventional therapy.

Materials

Unless otherwise stated, it will be understood that each homeopathic ingredient is combined in approximate equal proportions from approximately 0.1% to 20% v/v based on the volume to of the total homeopathic complex.

Also unless otherwise stated, homeopathic complexes for topical use, in the forms of creams, are generally in the low potency range, from for example mother tincture to approximately 18x/9c. For internal use, for example as a liquid composition, the homeopathic ingredients are generally of the high potency range from 30 plus, preferably 200c plus.

Finally and unless otherwise stated, when used as a cream, the homeopathic complex is generally combined with a base comprising approximately 25% Lanolin, approximately 50% approximately Petroleum with 25% Mineral oil. When used as a liquid the homeopathic complex is generally administered in alcohol and water, for example 20% ethyl alcohol and 80% purified water or 30-40% glycerine and 70% purified water. Alternative bases and carriers, as expanded in the specific Examples following, include topical antibiotics and Aloe Vera Veterinary spray.

The following complexes, defined in Cores A to D, were used in the Examples 1 to 9. Core A Ingredients Hepar sulphuris calcareum [Hep]; Lachesis muta [Lach]; Mercurius Solubilis [Merc] and Silica [Sil].

These are the essential anti-infective/anti sepsis ingredients. It will be understood that Lachesis may be replaced or complemented with many snake or spider remedies which have a similar septic shock profiles e.g. Crotalidae (*crotalus* Horridalus) and Tarentula *Cubensis*. Core B Ingredients Aconite napellus [Acon]
*Arnica montana* [Arn]
Arsenicum iodatum [Ars-i]
*Belladonna* [Bell]
*Bellis perennis* [Bell-p]
Bryonia alba [Bry]
Calenula Offcinalis [Calen]
*Chamomilla Matricaria* [Cham]
*Echinacea angustifolia* [Echi]
*Echinacea purpurea* [Echi-p]
Graphites naturalis [Graph]
*Hamamelis virginiana* [Ham]
*Hypericum* Perforatum [Hyper]
Ledum *palustre* [Led]
*Millefolium achillea* [Mill]
*Phytolacca* decandra [Phyt]
*Rhus Toxicodendron* [*Rhus*-T]
Ruta Graveolans [*Ruta*]
*Stellaria media* [Stel]
Sulphur [Sulph]
Symphytum *officinale* [Symph]

*Thuja Occidentalis* [Thuj]

Additional Core B ingredients, *Conium maculatum* [Con] and Gunpowder [Gunp], were used in Examples 1 to 9 only.

Core C Ingredients
Arsenicum album [Ars]
Apis mellifica [Apis]
*Astragalus membranaceus* [Astra-mem.]
Baptisia *tinctoria* [Bapt]
*Bufo* rana [*Bufo*]
Carbo vegetabilis [Carb-v]
*Calcarea* carbonica [Calc]
*Calcarea* fluorica [Calc-f]
*Calcarea* phosphorica [Calc-p]
*Gelsemium sempervirens* [Gels]
Iodium purum [Iod]
Ipecacuanha [Ip]
*Kali* iodatum [*Kali-i*]
Lac *caninum* [Lac-c]
Lac Bovinum Lac Vaccinum (cow)
Lycopodium *clavatum* [Lyc]
Nux vomica [Nux-v]
Phosphorus [Phos]
*Pulsatilla nigricans* [Puls]
Pyrogen [Pyrog]
*Sabal serrulata* [*Sabal*]
Sepia succus [September]
Staphysagria [Staph]
*Urtica urens* [Urt-u]
Zincum metallicum [Zinc]

Core D Ingredients
Adrenalin [Adren]
*Aesculus hippocastanum* [Aesc]
Baryta carbonica [Bar-c]
*Caladium* seguinum [Calad]
Cantharis vesicatoria [Canth]
*Cocculus indicus* [Cocc]
Histaminium (Histamine) [Hist]
Hydrastis *canadensis* [Hydr]
Lavender [Lav-v.]
Mezereum [Mez]
Nitric acid [Nit-ac]
*Paeonia Officinalis* [Paeon]
Prednisolone [Predni.]
*Ranunculus bulbosus* [Ran-b]
*Rumex crispus* [Rumx]
Thiosinaminum [Thiosin]
Sol [Sol]

Optional Nosodes

Nosodes are ideally selected from Tuberculinum bovinum, Tuberculinium aviaire, *Staphylococcus aureus*, Strepococcus, *Corynebacterium, E. Coli*, Colibacillinum, Bacillinum and/or Medorrhinum.

The following complex was used in Example 10.

This treatment essentially comprises, Core A, Core B minus graphites, *millefolium* and *thuja* and Core C minus Arsenicum, *Gelsemium* and Staphysagria, plus *Conium*.

| Name Of Remedy | Preferred Potency Range | Potency Of Example | Preferred Concentration Vol/Vol % Range | Actual Working Example Vol/Vol % |
|---|---|---|---|---|
| *Aconitum napellus* | 4x TO 12C | 6C | .1% TO 20% | 1.15% |
| *Aconitum napellus* | 12c TO 197c | 30C | .1% TO 20% | 1.15% |
| *Aconitum napellus* | 198c TO 10M | 200C | .1% TO 20% | 1.15% |
| *Apis* Mel 6c | 6C TO 1M | 6C | .1% TO 20% | 0.69% |
| *Arnica Montana* | 6x TO 27C | 6C | .1% TO 20% | 0.69% |
| *Arnica Montana* | 27c TO 1M | 30C | .1% TO 20% | 0.69% |

-continued

| Name Of Remedy | Preferred Potency Range | Potency Of Example | Preferred Concentration Vol/Vol % Range | Actual Working Example Vol/Vol % |
|---|---|---|---|---|
| *Astragalus* | 6x TO 27C | 6C | .1% TO 20% | 0.69% |
| *Astragalus* | 27c TO 1M | 30C | .1% TO 20% | 0.69% |
| Arsencium Iod | 6x to 24x/12c | 8x | .1% TO 20% | 0.69% |
| *Baptista* | 27c TO 1M | 30C | .1% TO 20% | 1.15% |
| *Belladonna* | 6c TO 100c | 30c | .1% TO 20% | 2.29% |
| *Belladonna* | 101c TO 997C | 200c | .1% TO 20% | 2.29% |
| *Belladonna* | 998C TO 9997C | 1M | .1% TO 20% | 2.29% |
| *Bellis Perenis* | 6x TO 27C | 6C | .1% TO 20% | 1.15% |
| *Bellis Perenis* | 27c TO 1M | 30C | .1% TO 20% | 1.15% |
| *Bryonia* | 4x TO 12C | 6C | .1% TO 20% | 2.29% |
| *Bryonia* | 12c TO 197c | 30C | .1% TO 20% | 2.29% |
| *Bryonia* | 198c TO 10M | 200C | .1% TO 20% | 2.29% |
| *Bufo* | 6x TO 27C | 6C | .1% TO 20% | 0.69% |
| *Bufo* | 27c TO 1M | 30C | .1% TO 20% | 0.69% |
| Calc Carb | 6x TO 27C | 6C | .1% TO 20% | 1.15% |
| Calc Carb | 27c TO 1M | 30C | .1% TO 20% | 1.15% |
| Calc Phos | 6x TO 27C | 6C | .1% TO 20% | 1.15% |
| Calc Phos | 27c TO 1M | 30C | .1% TO 20% | 1.15% |
| Calc Fluor | 6x TO 27C | 6C | .1% TO 20% | 0.69% |
| Calc Fluor | 27c TO 1M | 30C | .1% TO 20% | 0.69% |
| *Calendula* | 6x TO 1M | 6C | .1% TO 20% | 0.69% |
| Carbo Veg | 6x TO 27C | 6C | .1% TO 20% | 2.29% |
| Carbo Veg | 27c TO 1M | 30C | .1% TO 20% | 2.29% |
| *Chamomilla* | 6x TO 27C | 6C | .1% TO 20% | 0.69% |
| *Chamomilla* | 27c TO 1M | 30C | .1% TO 20% | 0.69% |
| *Conium* | 6x TO 27C | 6C | .1% TO 20% | 0.69% |
| *Conium* | 27c TO 1M | 30C | .1% TO 20% | 0.69% |
| *Echinaccea Angustifolia* | 6C TO 1M | 6C | .1% TO 20% | 0.69% |
| *Echinacea purpurea* | 6C TO 1M | 6C | .1% TO 20% | 0.69% |
| *Hammamelis* | 6x TO 1M | 30c | .1% TO 20% | 0.69% |
| Hepar Sulph | 30C TO 200C | 200c | .1% TO 20% | 2.29% |
| Hepar Sulph | 201C TO 9997C | 1M | .1% TO 20% | 2.29% |
| Hepar Sulph | 9999C TO 50M | 10M | .1% TO 20% | 2.29% |
| *Hypericum* | 6x TO 27C | 6C | .1% TO 20% | 0.69% |
| *Hypericum* | 27c TO 1M | 30C | .1% TO 20% | 0.69% |
| Iodium | 6x TO 27C | 6C | .1% TO 20% | 0.69% |
| Iodium | 27c TO 1M | 30C | .1% TO 20% | 0.69% |
| Ipecac | 6x TO 27C | 6C | .1% TO 20% | 0.69% |
| Ipecac | 27c TO 1M | 30C | .1% TO 20% | 0.69% |
| Kali Iod | 6x TO 1M | 6C | .1% TO 20% | 0.69% |
| Lac Caninum | 6x TO 1M | 30c | .1% TO 20% | 2.29% |
| Lac Bovinum | 6x TO 1M | 30c | .1% TO 20% | 2.29% |
| *Lachesis* | 6x to 12c/24x | 6c | .1% TO 20% | 1.15% |
| *Lachesis* | 12c TO 197c | 30c | .1% TO 20% | 1.15% |
| *Lachesis* | 198c TO 10M | 200c | .1% TO 20% | 1.15% |
| *Ledum* | 6x TO 27C | 6C | .1% TO 20% | 0.69% |
| *Ledum* | 27c TO 1M | 30C | .1% TO 20% | 0.69% |
| *Lycopodium* | 6x TO 27C | 6C | .1% TO 20% | 0.69% |
| *Lycopodium* | 27c TO 1M | 30C | .1% TO 20% | 0.69% |
| Merc Sol | 30C TO 200C | 200c | .1% TO 20% | 1.15% |
| Merc Sol | 201C TO 9997C | 1M | .1% TO 20% | 1.15% |
| Merc Sol | 9999C TO 50M | 10M | .1% TO 20% | 1.15% |
| *Nux Vomica* | 6x TO 27C | 6C | .1% TO 20% | 0.69% |
| *Nux Vomica* | 27c TO 1M | 30C | .1% TO 20% | 0.69% |
| Phosphorus | 6x TO 1M | 30c | .1% TO 20% | 1.15% |
| *Phytolacca decandra* | 6x to 12c/24x | 6c | .1% TO 20% | 2.29% |
| *Phytolacca decandra* | 12c TO 197c | 30c | .1% TO 20% | 2.29% |
| *Phytolacca decandra* | 198c TO 10M | 200c | .1% TO 20% | 2.29% |
| *Pulsatilla* | 6x TO 1M | 30c | .1% TO 20% | 1.15% |
| Pyrogen | 30C TO 10M | 1M | .1% TO 20% | 1.15% |
| *Rhus toxicodendron* | 6x to 12c/24x | 6c | .1% TO 20% | 0.69% |
| *Rhus toxicodendron* | 12c TO 197c | 30c | .1% TO 20% | 0.69% |
| *Rhus toxicodendron* | 198c TO 996c | 200c | .1% TO 20% | 0.69% |
| *Rhus toxicodendron* | 997C TO 9997C | 1M | .1% TO 20% | 0.69% |
| Ruta Grav | 6x to 12c/24x | 6c | .1% TO 20% | 0.69% |

-continued

| Name Of Remedy | Preferred Potency Range | Potency Of Example | Preferred Concentration Vol/Vol % Range | Actual Working Example Vol/Vol % |
|---|---|---|---|---|
| *Ruta Grav* | 12c TO 197c | 30c | .1% TO 20% | 0.69% |
| *Ruta Grav* | 198c TO 10M | 200c | .1% TO 20% | 0.69% |
| *Sabal* | 6x TO 27C | 6C | .1% TO 20% | 0.69% |
| *Sabal* | 27c TO 1M | 30C | .1% TO 20% | 0.69% |
| *Sepia* | 6x TO 27C | 6C | .1% TO 20% | 0.69% |
| *Sepia* | 27c TO 1M | 30C | .1% TO 20% | 0.69% |
| Silica | 6c TO 100c | 30c | .1% TO 20% | 2.29% |
| Silica | 101c TO 997C | 200c | .1% TO 20% | 2.29% |
| Silica | 998C TO 9997C | 1M | .1% TO 20% | 2.29% |
| *Stellaria Media* | 6x TO 1M | 30c | .1% TO 20% | 0.69% |
| Suphur | 6x TO 1M | 30c | .1% TO 20% | 2.29% |
| *Symphytum* | 6x TO 1M | 30c | .1% TO 20% | 0.69% |
| *Urtica* | 6x TO 1M | 30c | .1% TO 20% | 0.69% |
| Zincum Met | 4x TO 12C | 4c | .1% TO 20% | 0.69% |
| Zincum Met | 6x TO 1M | 30c | .1% TO 20% | 0.69% |
| | | | | 100.00% |

The following optional nosodes may also be added, at a preferred potency of 30C to 1M and a 1:1 ratio of each ingredient: Tuberculinum Bovinum, Tuberculinium Aviaire, *Staphylococcus Aureus*, Strepococcus, Strepococcus Mix, *Corynebacterium, E. Coli* (ColibacillinuM), Bacillinum and Medorrhinum at a preferred potency of 30C. *E. Coli* was added at a preferred potency of 200C.

The following homeopathic complexes were used in Examples 11 to 20. Vet cream

This treatment essentially comprises, Core A and Core B with graphites, sulphur and *thuja* (the optional Core B ingredients).

Each homeopathic ingredient was combined in approximate equal proportions based on the volume to of the total homeopathic complex and administered as a cream with a base comprising approximately 25% Lanolin, approximately 50% approximately Petroleum with 25% Mineral oil.

| Remedy | [Short form] | Range for Topical Use | Preferred Potency |
|---|---|---|---|
| Hepar Sulphuris | [Hep-s] | Range 2x-12x/6c | 3x |
| Lachesis | [Lach] | Range 8x-12x/6c | 8x |
| Mercurius Solubilis | [Merc-s] | Range 6x-12x/6c | 6x |
| Silica | [Sil] | Range 2x-12x/6c | 3x |
| Aconitum Napellus | [Acon] | Range 2x-12x/6c | 3x |
| Arnica Montana | [Arn] | Range MT-12x/6c | 3x |
| Arsenicum Iod | [Ars-i] | Range 6x-12x/6c | 6x |
| Belladonna | [Bell] | Range 2x-12x/6c | 3x |
| Bellis Perenis | [Bell-p] | Range MT-12x/6c | 3x |
| Bryonia Alba | [Bry], | Range MT-12x/6c | 3x |
| Calenula Offcinalis | [Calen] | Range MT-12x/6c | 3x |
| Chamomilla Matricaria | [Cham] | Range MT-12x/6c | 3x |
| Echinacia augustifolia | [Echi-a] | Range MT-12x/6c | 3x |
| Echinacia Purpurea | [Echi-p] | Range MT-12x/6c | 3x |
| Graphites naturalis | [Graph] | Range 8x-12x/6c | 8x |
| Hamamellis Virginiana | [Ham] | Range MT-12x/6c | 3x |
| Hypericum Perforatum | [Hyper] | Range MT-12x/6c | 3x |
| Ledum | [Led] | Range MT-12x/6c | 3x |
| Millefolium | [Mill] | Range MT-12x/6c | 3x |
| Phytolacca | [Phyt] | Range 6x-12x/6c | 6x |
| Rhus Toxicodendron | [Rhus-t] | Range MT-12x/6c | 3x |
| Ruta Graveolans | [Ruta] | Range MT-12x/6c | 3x |
| Stellaria Media | [Stel] | Range MT-12x/6c | 3x |
| Sulphur | [Sulph] | Range MT-12x/6c | 4x |
| Symphytum | [Symph] | Range MT-12x/6c | 3x |
| Thuja Occidentalis | [Thuja] | Range MT-12x/6c | 3x |

Mastitis Treatment

This treatment essentially comprises, Core A and Core B with optional ingredients *thuja*, sulphur and graphites and additional ingredients *Urtica*, Gunpowder and *Conium*. The addition of Gunpowder is optional and depends on Regulatory Rules.

Each homeopathic ingredient was combined in approximate equal proportions based on the volume to of the total homeopathic complex and administered as a cream with a base comprising approximately 25% Lanolin, approximately 50% approximately Petroleum with 25% Mineral oil.

| Remedy | Preferred Potency Range for Topical Use | Preferred Potency | Effective Final dilution in Cream |
|---|---|---|---|
| Hepar Sulphuris | 2x-12x/6c | 3x | 4x |
| Lachesis | 8x-12x/6c | 8x | 9x |
| Mercurius Solubilis | 6x-1x/6c | 6x | 7x |
| Silica[Sil] | 2x-12x/6c | 3x | 4x |
| Aconitum Napellus | 2x-12x/6c | 3x | 4x |
| Arnica Montana | MT-12x/6c | 3x | 4x |
| Arsenicum Iod | 6x-12x/6c | 6x | 7x |
| Belladonna | 2x-12x/6c | 3x | 4x |
| Bellis Perenis | MT-12x/6c | 3x | 4x |
| Bryonia Alb | MT-12x/6c | 3x | 4x |
| Calenula Offcinalis | MT-12x/6c | 3x | 4x |
| Chamomilla Matricaria | MT-12x/6c | 3x | 4x |
| Conium maculatum | MT-12x/6c | 8x | 9x |
| Echinacia augstofolia | MT-12x/6c | 3x | 4x |
| Echinacia Purpurea | 8x-12x/6c | 3x | 4x |
| Graphites | MT-12x/6c | 8x | 9x |
| Gunpowder | MT-12x/6c | 3x | 4x |
| Hamamellis Virginia | MT-12x/6c | 3x | 4x |
| Hypericum Perforatum | MT-12x/6c | 3x | 4x |
| Ledum | 6x-12x/6c | 3x | 4x |
| Millefolium | MT-12x/6c | 3x | 4x |
| Phytolacca decandra | 6x-12x/6c | 6x | 7x |
| Ruta Graveolans | MT-12x/6c | 3x | 4x |
| Rhus Toxicodendron | MT-12x/6c | 3x | 4x |
| Stellaria Media | MT-12x/6c | 3x | 4x |
| Sulphur | MT-12x/6c | 3x | 4x |
| Symphytum | MT-12x/6c | 3x | 4x |
| Thuja Occidentalis | MT-12x/6c | 3x | 4x |
| Urtica Urens | MT-200c | 30c | 30c |

Trauma/First Aid treatment

Each homeopathic ingredient below was combined in approximate equal proportions based on the volume to of the total homeopathic complex and administered as a liquid in alcohol and water, for example 20% ethyl alcohol and 80% purified water.

| Remedy | Preferred Potency Range for Topical Use | Preferred Potency | Effective Final dilution in Cream |
|---|---|---|---|
| Hepar Sulphuris | 2x-12x/6c | 3x | 3x |
| *Lachesis* | 8x-12x/6c | 8x | 9x |
| Mercurius Solubilis | 6x-1x/6c | 6x | 7x |
| Silica[Sil] | 2x-1x/6c | 3x | 4x |
| *Aconitum Napellus* | 2x-12x/6c | 3x | 4x |
| *Arnica Montana* | MT-12x/6c | 3x | 4x |
| Arsenicum Iod | 6x-12x/6c | 6x | 7x |
| *Belladonna* | 2x-12x/6c | 3x | 4x |
| *Bellis Perenis* | MT-12x/6c | 3x | 4x |
| *Bryonia Alb* | MT-12x/6c | 3x | 4x |
| *Calenula Offcinalis* | MT-12x/6c | 3x | 4x |
| *Chamomilla Matricaria* | MT-12x/6c | 3x | 4x |
| *Conium maculatum* | MT-12x/6c | 8x | 9x |
| *Echinacia augstofolia* | MT-12x/6c | 3x | 4x |
| *Echinacia Purpurea* | 8x-12x/6c | 3x | 4x |
| Graphites | MT-12x/6c | 8x | 9x |
| Gunpowder | MT-12x/6c | 3x | 4x |
| *Hamamellis Virginia* | MT-12x/6c | 3x | 4x |
| *Hypericum Perforatum* | MT-12x/6c | 3x | 4x |
| Ledum | 6x-12x/6c | 3x | 4x |
| *Millefolium* | MT-12x/6c | 3x | 4x |
| *Phytolacca decandra* | 6x-12x/6c | 6x | 7x |
| *Ruta Graveolans* | MT-12x/6c | 3x | 4x |
| *Rhus Toxicodendron* | MT-12x/6c | 3x | 4x |
| *Stellaria Media* | MT-12x/6c | 3x | 4x |
| Sulphur | MT-12x/6c | 3x | 4x |
| *Symphytum* | MT-12x/6c | 3x | 4x |
| *Thuja Occidentalis* | MT-12x/6c | 3x | 4x |
| *Urtica Urens* | MT-200c | 30c | 30c |

Example 1

Subject-Springer Spaniel Female neutered, age 5 years old on Day 0.
Condition/Symptoms of Subject
The patient presented with non-healing wound of what appeared to be a MRSA-type infection resulting from minor surgical wound as a result of elective surgery in the area of the stopper pad. The owner described the original wound as having been completely closed after surgery.
The patient had an ulcerative skin lesion which had started after minor surgery and had gradually extended.
There had been no response to repeatedly changed conventional antibiotics (Fuciderm®) or the antibiotic impregnated dressings used
After using a number of conventional antibacterial therapeutics the owner had decided to try an alternative approach.
Treatment
On Day 0 the patient was taken off all oral conventional medication. A cream consisting of Core A and Core B with the addition Fucidin was applied by mixing a tube of Topical Ophthalmic Antibiotic FUCITHALMIC® Viscous Eye Drops (1% fusidic acid). The Cream was applied to the affected area generously and the area bandaged up with cotton wool and an elastic self adhesive bandage and covered with an elastic adhesive bandage. Four days later, a very substantial improvement in the patient's condition was observed. Treatment with just a cream consisting of core A and core B was then repeated without the addition of the Fucidin. The patient was next seen in 5 months later and the treatment had been successful.

Conclusion

The dramatic and unexpected response in this subject confirms what has been seen in many other patients that the homeopathic complex of the invention work. There are no reported side effects, toxicity, administration was easy and the effectiveness in this species was dramatic and successful.

The homeopathic complex of the invention comprising Core A and Core B work when co-administered with conventional therapeutics, when the conventional therapeutic (antibiotic) did not work on its own. It shows the synergy with conventional therapy with no negative interaction This example also indicates that the homeopathic complex of the invention is capable of saving lives as in the case of this subject where it was non-responsive before treatment, with the potential of having a limb amputated if the condition had continued to progress as it had been, not only did it save the subject from an amputation with possible similar consequences, but it restored the limb to full normality completely healing the ulcers Example 2

Figure 1B:

Subject-Feline Male Neutered of Indeterminate Age
Conditions/Symptoms of Subject
The subject originally presented as a post road traffic accident patient, with multiple traumatic skin injuries and multiple fractures of the left femur the latter were repaired by open reduction and intramedullary pining. The fracture site had to be partially re-broken as there was already cartilaginous callus repair with very mal-aligned bone fragments.
The subject was post shock. It was already in the healing phase of injury, but the wounds were still open and fresh. The bone fractures were attempting to heal out of alignment. The subject was initially unable to walk on the hind legs despite having one un-fractured leg. The musculature bones and wounds were all painful. The wounds were due to grazing probably from contact with a road surface and so friction burns as well as wounds, bruising and fractures were present.
Treatment
The fractures were treated by open reduction. Immediately post surgery the patient was administered a 0.21 ml liquid dropper dose of a complex of Cores A, B and C combined in an excipient of 20% ethyl alcohol and 80% purified water. This was given on a first aid basis to aid recovery and promote rapid healing. Subsequently, a cream comprising Core A and B for topical application in a base carrier of 25% Lanolin and 50% white petroleum at 2 oz/lb and 25% mineral oil with the homeopathic combination added at 3.33% Vol/Vol (3.33 ml/100 ml) w/w (3.33g/100g) was applied topically to all wounds and known bruised regions including the surgical wound particularly over the fracture site. Antibiotic cover was provided by Crystapen into the surgical wound and parental Amoxycillin and Clavulanic Acid (Synulox Pfizer), but would not explain the rapidity of recovery other than the absence of infection.
Result
FIG. 1a shows the subject of Example 2 pre-treatment and FIG. 1b shows the subject of Example 2 after a 24 hour of treatment.
The results were dramatic with the patient walking to obtain food within 48 hours of the surgery. Not only that but as pictures FIG. 1a and FIG. 1b show the rate at which healing progressed in this patient with the gap between photographs of the same wound being of the order of 24 hours. All wounds had completely resolved in a 10 day period.

Conclusion

This case shows the unexpected rapidity of wound, fracture and injury resolution brought about by the use of the Cream with Core A and B combined topically and the oral administration of just a single unrepeated dose of Core A, B and C in a liquid dose form.

It once again shows the synergy with conventional therapy with no negative interaction. Once again there were no reported side effects, toxicity, administration was easy and the effectiveness in a different species to Example 1 was just as dramatic and successful Example 3 (A)

Figure 2A:
FIGS. 2A & 2B show the "Sambo" Equine Gelding at Day 1/Day 11 of Example 3A prior to treatment (FIG. 2A) and after treatment (FIG. 2B)

Subject-"Sambo" Equine Gelding 14-16 Years Old
Conditions/Symptoms of Subject
  Subjects, "Sambo" Equine Gelding 14-16 years old and a piebald mare, presented with acute severe photo-dermatitis due to sun over-exposure.
  All the un-pigmented skin on the nose was suffering from severe solar radiation burns (FIG. 2a)
  The skin on the nose was sunburnt, oozing, scabby, cracked, and painful to movement and touch. There were also patches of sloughing.

Treatment

Figure 2B:
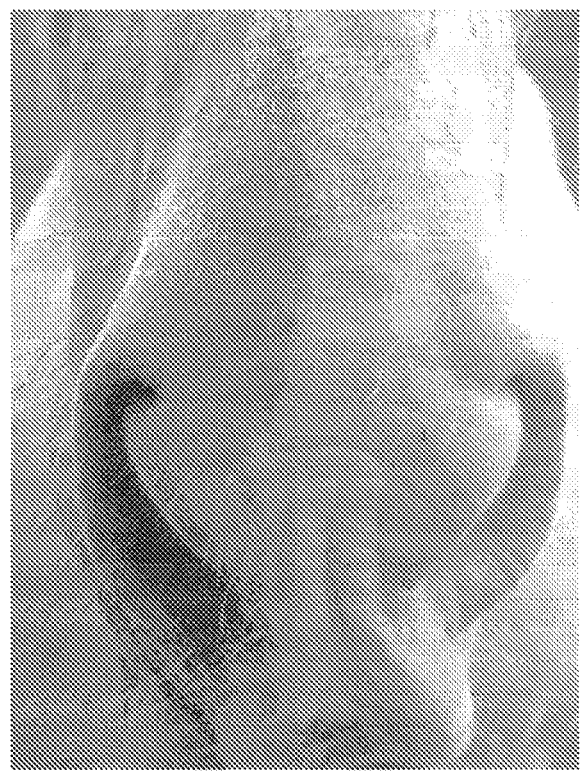

A cream comprising Core A and B for topical application in a base carrier of 25% Lanolin and 50% White Petroleum at 2 oz/lb and 25% mineral oil with the homeopathic combination added at 3.33% (3.33 ml/100 ml) was applied topically on a twice daily basis for 5 days to the affected areas of the subject and then once daily due to the rapidity of improvement. Results FIG. 2a was taken on day one with FIG. 2b taken 11 days later. The homeopathic complex used promoted rapid healing and also conferred some form of resistance to further sunburn or sun sensitivity This protocol has been repeated with other horses with exactly similar results. In one patient so severe was the reaction that the glands on the neck swelled up in acute response. The affected area was so sore cream could only be applied around the affected area. However, a similar response was achieved.

Conclusion

Previous cases of equine photo-dermatitis had taken between 3 months in mild cases, to 6 months in similarly severe cases to recover and then in many cases residual scarring was present. This case shows the unexpected rapidity of burn resolution brought about by the use of a topical cream with Core A and B.

Example 3 (b)

Figure 3A:
FIGS. 3A & 3B show the pig of Example 3b prior to treatment (FIG. 3A) and after treatment (FIG. 3B)

Subject-Herd of Male and Female Pigs Less than 1 Year of Age
Conditions/Symptoms of Subject
  Subjects were presented with acute severe photo-dermatitis after being left out on new pasture during a period of unbroken sunshine. The subjects presented much as a case of bad human sunburn would (FIG. 3a) with the whole patient having a bright red burning hot inflamed tender skin with crusting of the skin at the worst affected areas where there was deep cracking due to third degree burning. There were areas of peeling and scabbing of the affected skin. Treatment Due to success with previous cases in a range of other species a treatment with Core A and Core B combined was used. However, due to the number of animals a novel delivery method was required. Aloe Vera Veterinary Spray (Forever Living Products) was used as a carrier for Core A and Core B. Once daily spraying of the carrier with Core A and Core B was decided upon with a second spray when possible at feeding time.

Result

Figure 3B:

A complete and total resolution of all the symptoms of severe sunburn leaving normal healed skin was achieved in 10 days and this change is shown in FIG. 3b. The skin is normal pink and healthy with no signs that would normally be expected with this degree of sunburn having been present 10 days earlier. This similar to Example 3a the improvement and healing was achieved in a very short time period.

Conclusion

This case shows yet again the unexpected rapidity of burn resolution brought about by the use of the Cream with Core and Core B combined topically. In addition, it demonstrates both the healing properties of the invention and the anti-sepsis properties of the Cores (none of the burns in the group became infected despite the muck, dirt and flies that were present). Additionally, the homeopathic complex minimized scarring. Furthermore, the homeopathic complex may be used with groups, herd, flocks etc.

Example 4

Subject-Cavalier King Charles Female—not Neutered Age 31/4 Years Old.
Conditions/Symptoms of Subject
  Patient presented with acute mastitis. Initial examination showed the patient to have a temperature in excess of 104° F./40° C. The mammary glands were hard swollen and in danger of gangrene on assessment. The patient was treated with a combined homeopathic and conventional therapy.

Treatment

As the condition was acute severe and life threatening, it was decided to treat with a combination of homeopathic and conventional therapy.

An initial injection of Synulox® (Amoxycillin Trihyd, Clavulanic Acid) at a dose of 1 ml SC and Clamoxyl LA® (Amoxycillin Trihyd) at a dose of 2 ml SC and an oral dose of 15 drops of Cores A, B and C with nosodes at doses of 0.07 ml/drop which was approximately 1 ml liquid dropper dose of complex of Cores A, B and C combined in an excipient of 20% ethyl alcohol and 80% purified water to act as an anti-infective was administered as a single initial dose. Topical application of a cream comprising Core A and B for topical application in a base carrier of 25% Lanolin and 50% white Petroleum at 2 oz/lb and 25% Mineral oil with the homeopathic combination added at 3.33% (3.33 ml/100 ml) was also carried out. The patient was checked the following day and the mammary glands as evidenced in the picture below had virtually returned to normal. The owner was told to complete the antibiotic course to prevent any resistance developing.

Results and Conclusion

The owner reported that by the time the dog got home some 15 minutes after being given the Cores A, B and C orally as a liquid preparation and having topically applied a cream with Cores A and B the subject had already started to improve.

Figure 4:
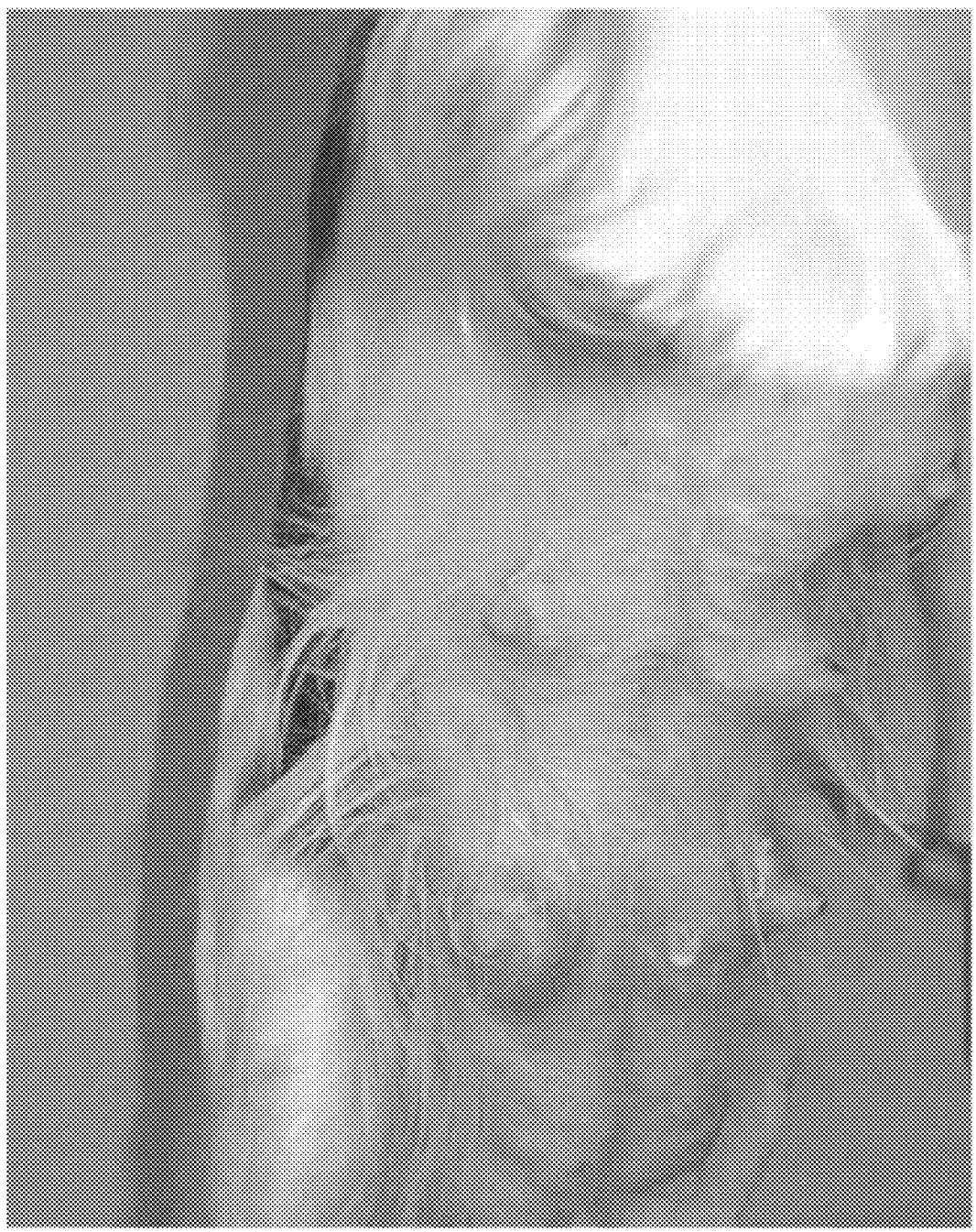
FIG. 4 show the Cavalier King Charles Female of Example 4 within 24 hours start of treatment.

FIG. 4 shows the subject within 24 hours of the start of treatment. The patient was checked the following day and the mammary glands had virtually returned to normal within a 24 hour period. The owner was told to complete the antibiotic course to prevent any resistance developing.

Conclusion

This example demonstrates the synergy of the homeopathic complex of the invention and correctly chosen conventional pharmacotherapy, an antibiotic in this case. It demonstrates the speed of action of this invention as some 15 minutes after initiation of therapy there had been an improvement and within 24 hours there appeared to be almost complete resolution of the mastitis, which was severe and septic in nature. It demonstrates that this medication is capable of speeding the resolution of a very severe case of acute sepsis in conjunction with conventional therapy.

Example 5

Figure 5A:
FIGS. 5A & 5B shows the Canine Collie of Example 5.
Figure 5B:

Subject-Canine Collie Cross Male 1 Year Old
Conditions/Symptoms of Subject
  Subject presented with several skin reaction (around nose area) to hogweed or other related plants (FIG. 5(a) before (b) after).
  The skin had vesicles which were intensely itchy and were oozing serum as a result of intense puritus.
Treatment
  Twice daily topical treatment with cores A and B and oral treatment with modulator Rannunculus *Bulbosa*, Sol 30c from core D.
  Core A and B were administered as a cream in a buffered cream base carrier of Purified water BP, Soft White Paraffin BP, Dehydag Wax, Liquid Paraffin BP, DiSodium Hydrogen Phosphate BP Citric Acid BP and Chlorocresol BP for Core D modulators added at 3.33% and combined and 50% White Petroleum at 2 oz/lb and 25% Mineral oil with the homeopathic combination added at 3.33% (3.33 ml/100 ml).
  *Rhus* Tox and *Urtica Urens* 6c were also administered with Core A and Core B.
Result
Condition Disappeared after Homeopathic Complex Administration
Conclusion
  This example demonstrates the antipuritic and anti-inflammatory as well as the wound resolution capabilities of the homeopathic complex. Both plant chemical burns and auto-immune conditions are generally very difficult to resolve even over a prolonged period often leaving severe scarring or a constantly recurrent condition. The resolution of this case alone was unexpected without having a protracted treatment period with considerable scaring.
  This example also demonstrates the speed, efficacy, safety (as dogs continually lick off the cream in this location) and ease of use where the condition was painful and puritic and yet was alleviated on administration of the cream.

Figures 6A, 6B:
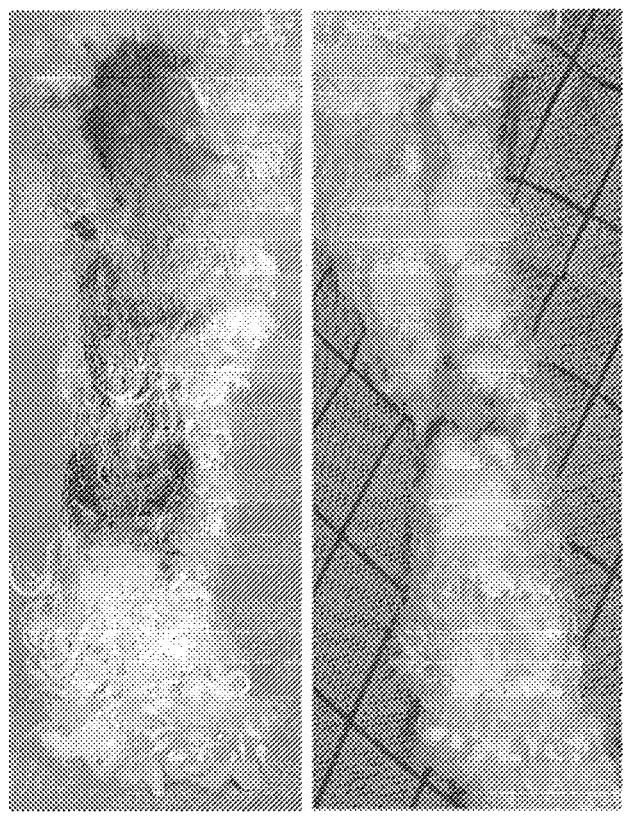
FIGS. 6A-6D show the Bichon Frise Male 6 years of Example 6. The state of the wound is and the repairs due to the cream are shown in FIG. 6A to 6D.
Figures 6C, 6D:
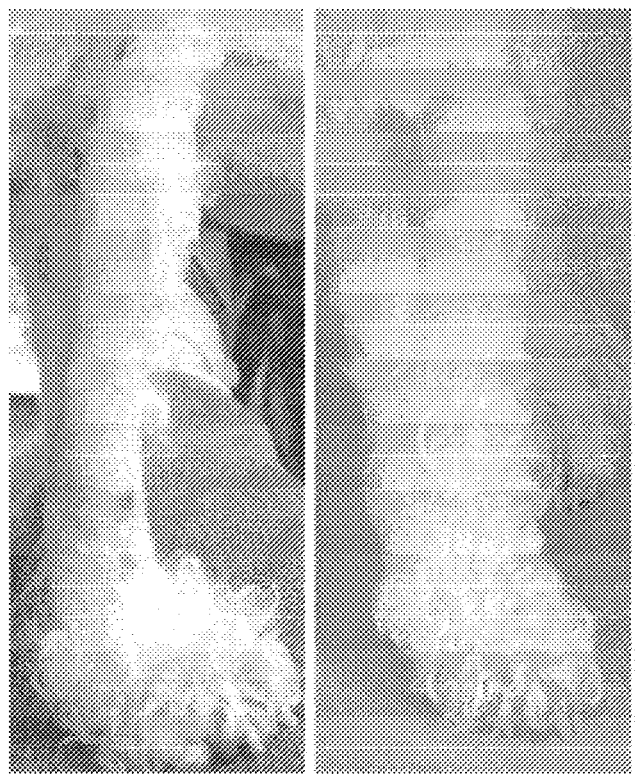

Example 6: Wound Healing Case Study-Wound Closure of a Chronically Infected Non Healing Wound Subject-Bichon Male Neutered 6 Years Old.
Conditions/Symptoms of Subject
  The subject presented with severe damage to tissues of the leg where there were areas of necrotic tissue that sloughed leaving even more exposed areas. The patient presented with a suspected hairline fracture of a digit. The leg was severely wounded and was bandaged.
  The patient was already on antibiotic therapy and there was antibiotic dressing on the wounds. The owner sought a second opinion on the basis that the wound smelled strongly offensive, the patient was much more tender and lame on the affected leg. FIG. 6a gives a very accurate idea of the condition the leg was in when the dressing was removed initially, although the picture was taken after ten days of treatment following the initial second opinion consultation Treatment
  Initial treatment was with antibitiotics Synulox® 250 mg composition (200 mg amoxicillin and 50 mg clavulanic acid) was given orally at a dose of ½ tablet twice daily for 7 days along with Metronidazole 200 mg ½ tablet twice daily for 7 days. The wound was left open. At this point due to lack of progress the antibiotic was changed to Lincocin (Antirobe 50 mg) 1 tablet twice daily. Calendula 6c was given orally three times daily to try promote healing. Although the wound no longer smelled, its healing had failed to progress at all.
  It was decided at this point to abandon systemic antibiotic therapy to treat the wound. The patient was anaesthetised using ACP2 mg/ml as a premed.05 ml IM, Thiopentone 2.5% IV as a knockdown anaesthetic and maintained on Isoflourane. A swab was taken for culture at this point despite antibiotic therapy, as it was hoped that it might give some indication of a suitable treatment. The area around the wound was clipped and tension sutures placed in the wound which failed to provide reasonable apposition but did reduce some of the wound size. The wound was once again washed with Hibiscrub Surgical Wash, followed by povodine Iodine surgical scrub and then rinsed with saline and then bathed in sterile water with Homeopathic Mother tincture of Calendula (Marigold) at a dilution of 20 drops of mother tincture add to 100 ml of sterile water. The wound was then allowed to dry fully and a cream comprising Core A and B for topical application in a base carrier of 25% Lanolin and 50% White Petroleum at 2 oz/lb and 25% Mineral oil with the homeopathic combination added at 3.33% (3.33 ml/100 ml). The cream was to be applied to the open wound 2 to 3 times daily. All antibiotic therapy was discontinued. The most open upper part of the wound had tension sutures placed in it to draw the edges somewhat closer together. This was to be followed by the application of the cream as described as the wound still remained very open.
  Within 10 days as in the previous examples a huge amount of healing had taken place with the photograph FIG. 6b showing the change at day 12. Within 30 days the wound was completely healed and only a thin scar remained (FIG. 6c) and within a year the scar was virtually completely gone and almost the entire area had normal hair re-growth (FIG. 6d)
  Result 20 days after the initial injury and just 7 days after starting treatment the healing results were amazing the odour was completely gone the skin and wound showed a dramatic healing even in the area where the skin was black and hard it had gone soft and pink.
  Three weeks later, the wound is fully closed, clean with hair re-growth.

Conclusion
  The homeopathic complex when applied to this wound acted as an anti-infective as antibiotic therapy was terminated when therapy with the cream comprising Core A and B was initiated in addition to this the rate of wound healing and resolution was dramatically accelerated as shown in FIGS. 6(a-d). The end result was an almost total return to normal of the affected area, a dramatic result by any standards.
  This example demonstrates the true extent of action of Core A and B when used on their own in a cream delivery system to a wound with indolent healing features as in this case where after over 10 days there was no sign of granulation or healing in the wound yet with the introduction of the invention the wound which was large and non healing suddenly started to show accelerated healing.

It also demonstrated that this invention acts with similar efficacy across many different types of wound and skin condition a very unique feature. It demonstrates the usefulness of the invention with septic wounds and particularly those with antibiotic resistant infections (Multi-resistant Infections) as in this wound a range of antibiotics had been used with no resolution of the wound. The prolonged nature of the treatment also demonstrated the safety and lack of toxicity or side effects of the invention as the owner continued to apply the cream sparingly to the affected area for months till almost any signs of scarring let alone the wound had resolved. It also shows how well tolerated the invention is in this format-despite how painful, raw and sensitive the area was the owner was able to apply the invention several times a day.

Example 7 (A)

Subject-Human 31 Year Old Lactating Female.
Conditions/Symptoms of Subject
The subject a 31 year old female developed a complaint of sore swollen painful breasts associated with the breast feeding of her second child.
The symptoms began to appear within 10 days of leaving the hospital post birthing.
The glands were swollen and painful to the touch, the breasts were engorged with milk and the patient complained that breast feeding was difficult at best. There had been no previous history of any mammary gland infection with the pervious child birth. A diagnosis of post birthing mastitis was given and a course of antibiotics were prescribed by the treating physician. After several days the patient still had no relief and began to seek alternative options.

Treatment
The patient began treatment with oral dosing of the homeopathic medication complex for mastitis comprising Cores A, B and C (no nosodes) in dropper dose in an excipient of 20% ethyl alcohol and 80% purified water twice daily with the product being sprayed onto the oral mucosa 13 days post birthing.

Result
Relief was established within 24 hours and a total elimination of symptoms in 48 hours. There has been no re-occurrence of the condition or symptoms since treatment Example 7 (B)

Subject-Human 30 Year Old Lactating Female.
Conditions/Symptoms of Subject
A 30 year old white female was presented with health concerns that arose 4 days after leaving hospital after giving birth to a female child. The patient was in hospital for 3 days and the condition did not manifest until 4 days post hospital. This was a second child and the patient did not have a history of mastitis-mammary gland infections.
Symptoms included a high fever, painfully swollen mammary glands with pain extending under left arm. Breasts were extremely painful to the touch and breast feeding was problematic at best. General movement was also guarded due to the inflammation and pain associated with movement.

Treatment
Three sprays, 2 ml, of the liquid homeopathic medication complex for mastitis comprising Cores A, B and C (no nosdoes) in dropper dose in an excipient of 20% ethyl alcohol and 80% purified water was administered by the subject 3 times daily for 2 days based on the nature of the condition and the lack of response to antibiotic therapy on its own.

Result
Pain was reduced after 3 hours, inflammation was reduced within 24 hours and a total resolution was achieved in 48 hours.

Conclusion
The response confirmed that Cores A to C work as an anti-infective and anti-inflammatory in humans. It demonstrates a rapid response in humans to the invention and that the invention is safe and side effect free in humans.

It shows that the use of Cores A to C internally (this can also be delivered transdermally, orally, perivaginally or parentrally) demonstrates a consistent response as a potent anti-infective agent.

Example 7 (C)

Subject-Human Male 60+Year
Conditions/Symptoms of Subject
Subject was diagnosed with meningioma and had surgery to remove the same. As follow up radiation therapy was done 5 days a week for 6 weeks. The subject presented with itching and soreness of the skin over the area of radiotherapy, a known consequence of radiotherapy.

Treatment
The invention was provided in the form of a cream comprising Core A and B for topical application in a base carrier of 25% Lanolin and 50% White Petroleum at 2 oz/lb and 25% Mineral oil with the homeopathic combination added at 3.33% (3.33 ml/100 ml). The cream was to be applied to when the skin was itchy and sore after radiotherapy on an as needed basis. Result As soon as the patient applied the cream the skin conditions were relieved. The patient was able to complete the radiotherapy course with simple easy to apply relief when required Conclusion Core A and Core B formulated as a cream works in humans similar to animals and this is one of a series of similar cases all with similar positive results. The invention has a rapid and immediate effect. The invention is effective in treating burns, burn wounds, itch, soreness and radiation burns.

Example 8: Wound Healing Case Study-Septic Post Surgical Mastectomy Wound Healing Subject-Tabby and White Domestic Short Haired Cat Female not Neutered Estimated Age 6-7 Months
Conditions/Symptoms of Subject
The subject presented as a second opinion case where a unilateral mastectomy had been carried out due to gangrenous mastitis. The subject had had the surgery a little less than a week previous to being brought to us, all her kittens had died prior to the mother arriving with us from a combination or the initial malnutrition and sepsis from the mastitic milk. Thus only the mother was presented and she had continued to deteriorate during the post surgical period much as had occurred with the kittens. The subject presented with a fever of 103.5° F. and was already on Convenia, a 14-day duration antibiotic containing the active ingredient Cefovecin, a cephalosporin, and was failing to improve. The patient was in appetent and a large area of tissue was still on the point of sloughing. The initial presentation was fairly dramatic with a lack of response to conventional medications (FIGS. 7a to 7d).

Treatment

The subject was given twice daily oral dosing with 5 drops or 35 ml of the delivery dose was administered by mouth twice daily. The delivery dose comprised of Cores A, B and C with the following Nosodes: Tuberculinum Bovinum, Tuberculinium Aviaire, Staphylococcus Aureus, Strepococcus,Strepococcus Mix, Corynebacterium, E. Coli (ColibacillinuM),E. Coli, Bacillinum and Medorrhinum, in a liquid dropper. Cores A, B and C with Nosodes were combined and added at a rate of 0.07 ml/ml in an excipient in glycerine 30% with purified water to act as an anti-infective. In addition cream comprising Core A and B for topical application in a base carrier of 25% Lanolin and 50% White Petroleum at 2 oz/lb and 25% Mineral oil with the homeopathic combination added at 3.33% (3.33 ml/100 ml). The cream was to be applied to the open wound 2 to 3 times daily. All antibiotic therapy was discontinued.

Result

Within 24 hours the non responsive subject had a decrease in it pyrexia from 103.5° F. to 102.2° F. and had started eating. The patient has also started drinking again, the wound still looked appalling, but had a less putrid odour FIG. 7a and within in 3 days the patient had improved dramatically with the gangrenous area having sloughed and healing had started to rapidly occur in the affected area the cat was now eating, drinking, walking around and purring again.

Within 7 days the entire wound area was dry an all oozing gone due to the rapid rate of healing the fact that the patient had previously been under general anaesthesia for the original surgery and non responsive treatment Applicants decided to allow the wound to heal by second intention.

Figure 7A:
FIGS. 7A to 7D show the Cat of Example 8.
Figure 7B:
Figure 7C:
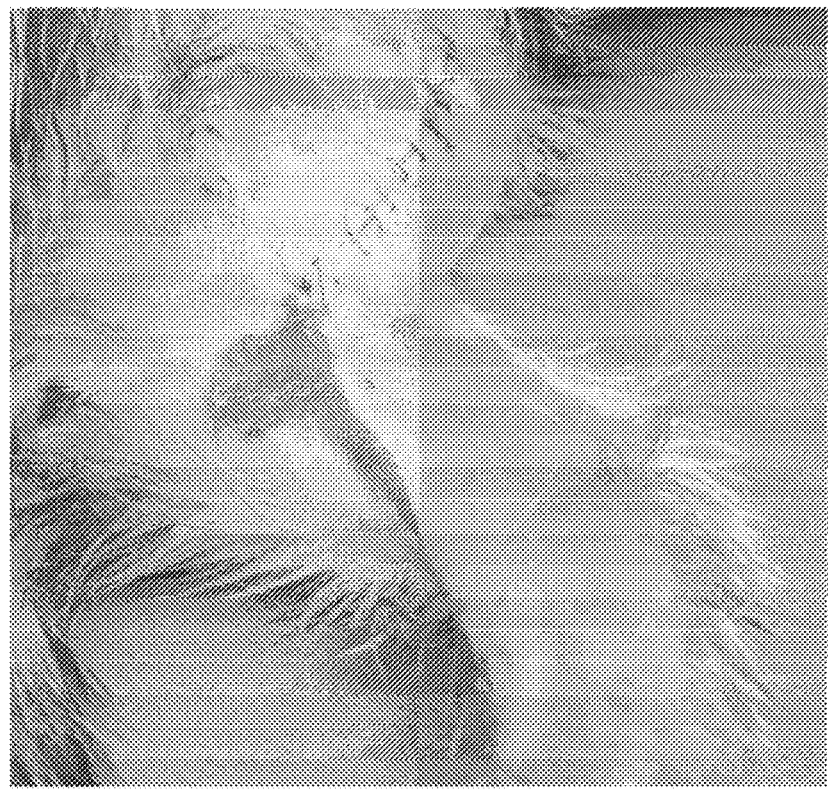
Figure 7D:
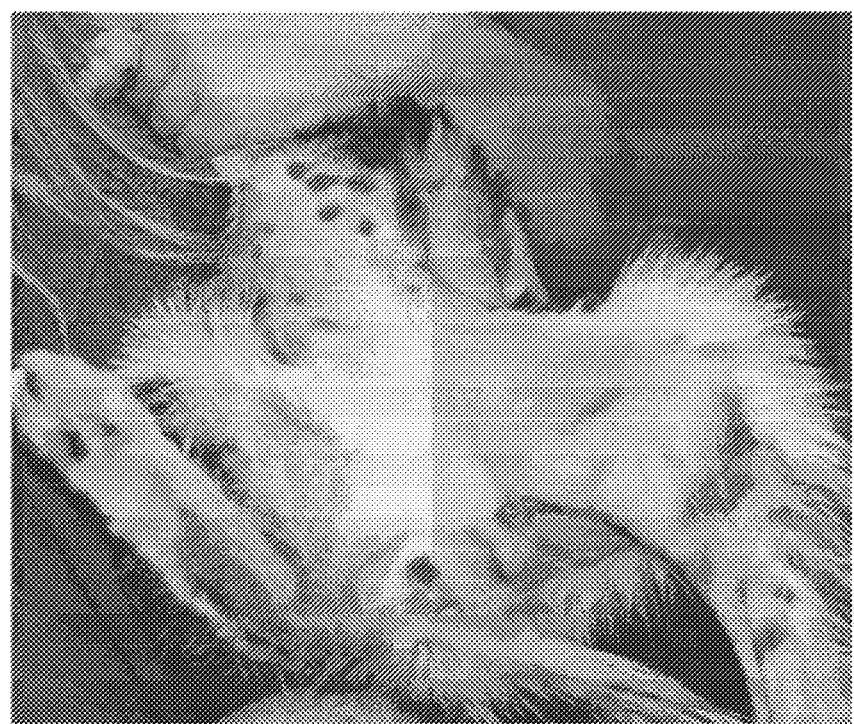

FIG. 7c-ten days after initiating treatment the patients wound had reduced in surface area sufficiently for some areas of the wound to have started to close showing no trace scarring. FIG. 7d—at the three week stage healing was virtually complete and the patient sent home. Further reports on the subject is that it continues to do well and no one would know the problem was ever there Conclusion The homeopathic complexes administered are effective in the presence of resistant infection not susceptible to previously chosen antibiotic cover and produce a rapid response with a fast drop in temperature showing the invention acting as an anti-pyretic. The invention is safe as there were no side effects seen where the invention was applied both internally and externally over a large surface area for a prolonged period in a subject. The invention acts as a potent anti-infective composition. The invention promotes wound healing even in very large septic wounds. The invention can be co-administered with antibiotics. The invention is non-toxic, the subject being a cat continually washed the cream off its coat for the entire duration of treatment and showed no ill effects. The invention has anti-inflammatory and analgesic properties as the subject was rapidly able to get up and walk around. The invention is easy to use due to the above the subject allowed easy administration of the invention to area that were obviously sore. The invention can be administered by multiple routes and by multiple delivery methods.

Example 9: Wound Healing Case Study-Treatment of Mastitis and Mammary Hypertrophy Subject-Domestic Short Haired Cat F<2 Years Conditions/Symptoms of Subject The subject had already received treatment before being brought for a second opinion. The subject had already been given Convenia, a 14 day duration antibiotic with active ingredient Cefovecin (a cephalosporin), and had failed to improve over the subsequent treatment period and had in fact got worse with the mammary glands continuing to increase in size and discolouration, the patient had become lethargic and in-appetent, but still continued to eat some food.

Figure 8A:
FIGS. 8A & 8B shows the cat's mammary gland and comparably sized golf ball of Example 9.
Figure 8B:
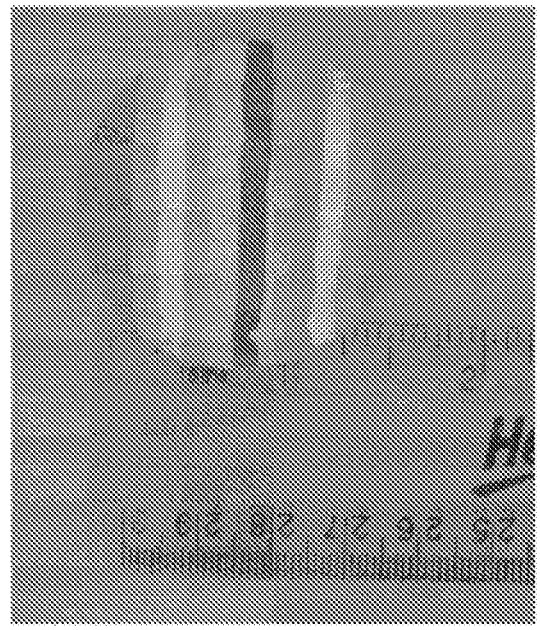

The subject presented with massive mammary hypertrophy and a history of what was diagnosed as mastitis. FIG. 8a shows the degree to which the mammary glands were enlarge discoloured. FIG. 8b shows the ball that was placed between the glands as a reference to show the true size of the gland swelling.

Treatment

The subject was given twice daily oral dosing with 5 drops or .35 ml of the delivery dose was administered by mouth twice daily. The delivery dose comprised of Cores A, B and C with Nosodes as per Example 8 in a liquid dropper. Cores A, B and C with Nosodes were combined and added at a rate of 0.07 ml/ml in an excipient in glycerine 30% with 70% purified water to act as an anti-infective. In addition cream comprising Core A and B for topical application in a base carrier of 25% Lanolin and 50% White Petroleum at 2 oz/lb and 25% Mineral oil with the homeopathic combination added at 3.33% (3.33 ml/100 ml). The cream was to be applied to the entire mammary are 2 to 3 times daily. All antibiotic therapy was discontinued.

Result

Within 10 days there was complete resolution of the condition the speed and rapidity of which is evidenced when one compares FIG. 8a and FIG. 8b. The glands which were sufficiently large to hold the ball between them and were much larger than the 1.5 cm ball had within 10 days returned to an almost flat in active state. A remarkable change considering the starting point and the lack of response to previous therapies Conclusion Thus, the homeopathic complex of the invention is effective in the presence of resistant infection not susceptible to previously chosen antibiotic cover and produces a rapid response with a rapid reduction in size of the affected mammary glands on a daily basis.

The invention is safe as there were no side effects seen where the invention was applied both internally and externally over a large surface area for a prolonged period in a subject. The invention is non toxic.

The homeopathic composition of the invention acts as an effect anti-infective in cases of mastitis which is both complementary and synergistic with conventional medication and promotes healing as demonstrated in this Example.

The invention can be co-administered with antibiotics.

Furthermore, conventional treatments for mastitis and mammary hypertrophy did not achieve the same effect and the nine day return to normal of the patient in this example was exceptionally rapid. The authors note a case where the hypertrophy had been present for 8-12 weeks and after starting after an injection of delvosterone had continued to get larger on a daily basis until Delvosterone 11c was given. In this case the reduction was slower and damage took longer to heal.

Example 10: Homeopathic Therapy Evaluation for Subclinical Mastitis in Lactating Holstein Cows Field trials were carried out using an anti-infective homeopathic complex Materials The Mastitis treatment was administered as defined in the General materials section. Nosodes were not included for the purposes of this trial.

The homeopathic ingredients were extracted in 95% ethanol (USP, BP, EP) and 10% triple distilled water. The following carrier was used for the resultant homeopathic complex 20% ethanol and 80% purified water.

Objective:

The objective of this study was to evaluate the effect of the homeopathic treatment above, on somatic cell counts and immune status of cows.

INTRODUCTION

High somatic cell counts (SCC) in milk are the primary indicator of an infection in the mammary gland and intra-mammary infections result in reduced milk production and lower quality of milk. Elevated somatic cell counts can be the result of a clinical or sub-clinical infection or, in some cases, SCC may be elevated in the absence of a pathogenic organism. Generally, if a cow exhibits clinical mastitis, then this cow is treated with an antibiotic, by intramammary infusion or systemically, depending on the severity of the clinical signs. If a sub-clinical infection is determined from a microbial culture of the milk, the cow is monitored but not treated until the end of lactation, since treatment of these cases during lactation is not usually effective. Treatment at dry-off has been established to be the most effective treatment for a sub-clinical mastitis infection. Sub-clinical infections result in reduced milk production that can be a loss of several thousand dollars per animal per lactation. In addition, elevated SCC results in the loss of quality premiums for producers. Therefore, reducing SCC and sub-clinical infections are beneficial for both animal health and profitability. Alternative treatments, including homeopathic treatments, have been suggested as effective treatments for sub-clinical mastitis or other health concerns for dairy cows. However, these products have not been adequately researched under controlled study conditions and the only information available is from testimonial reports and studies conducted by the industry that did not have appropriate controls and have not been published. It is unknown if the product, Mastoblast, is effective in reducing SCC and if the product can reduce the incidence of intramammary sub-clinical infections.

Protocol:

Twenty-four lactating cows from the University of Connecticut diary herd were selected based on the pattern of somatic cell counts in milk and the presence of a mastitis pathogen (sub-clinically infected) from the CT Mastitis Laboratory. Animals were then paired by SCC, infection status, age and stage of lactation and randomly assigned to one of the two treatments within classes of infection status.

Treatment design was follows:

| Treatment A | Mastitis Treatment |
|---|---|
| | 6 cows with postive cultures (if possible) |
| | 6 cows with negative cultures |
| Treatment B | Control Treatment |
| | 6 cows with postive cultures (if possible) |
| | 6 cows with negative cultures |

Cows were housed separately by treatment group within the Kellogg Dairy Centre throughout the study period.

Cows were aseptically cultured at day-3 and day-1 and day 3 to verify the intramammary infection status and SCC and at least nine cows will be assigned to each treatment. The homeopathic treatment and control treatment were administered as a spray on the nasal membranes for 10 days starting at day 5. Starting at day 2, milk was sampled from the afternoon milking for SCC analysis every three days for two weeks. Thereafter, milk was sampled for SCC once weekly through 8 weeks. Milk was sampled aseptically for pathogen analysis on a two-week basis up to 10 weeks. Daily milk production was recorded. Monthly milk fat and protein content was determined from DHI testing. Blood, from veni-puncture and milk samples was collected from each animal at twice per week to measure differential counts of white blood cells to assess immune status in the cows. Effect of the treatment on SCC, milk production and immune status was analyzed by ANOVA and the GLM procedure of SAS.

Materials and Methodology

The study was 60 days in length. At day 1, foremilk was aseptically collected from each quarter of all cows and analyzed for mastitis pathogens at the University of Connecticut Mastitis Laboratory and bacteriological status of milk samples was determined by diagnostic procedures recommended by the National Mastitis Council (1987). Milk was then sampled from the total milking of each cow on day-1 and analyzed for SCC (Marshall, 1992) and for the immunoglobulins $G_1$ ($IgG_1$) using ELISA quantitation kits (Bethyl Laboratories, Inc; Montgomery, TX). These values provided baseline nonspecific estimates of the intramammary infection status of each quarter and the immune system status.

On day 1 through day 10, the homeopathic therapy and the placebo were administered twice daily before each milking. On days 3, 7, 10, 13, 16, 22, 28, 35, 42, 49, and 56 milk was sampled and analyzed for SCC. On days 3, 13, 22, 28, 35, 42, 49 and 56 the milk samples were also analyzed for $IgG_1$. In addition, on days 28 and 56, foremilk from each quarter for all cows was aseptically collected and analyzed for mastitis pathogen as described earlier. If a cow developed clinical mastitis, the data from that cow were removed from the analysis due to marked increases in SCC and immunoglobulins due to clinical mastitis that may bias the analysis. In this study, the sample size was not large enough to accurately determine treatment differences for clinical mastitis, because clinical mastitis is usually a low incidence disease.

Results

| | P Values Treatment | Time | Treatment time |
|---|---|---|---|
| SCC | 0.87 | 0.48 | 0.46 |
| IgG1 | 0.006 | 0.0001 | 0.0001 |
| IgG2 | 0.52 | 0.17 | 0.0002 |
| Infections | 0.12 | 0.63 | 0.35 |
| Significant effects from IgG1, only | | | |

Figure 9A:
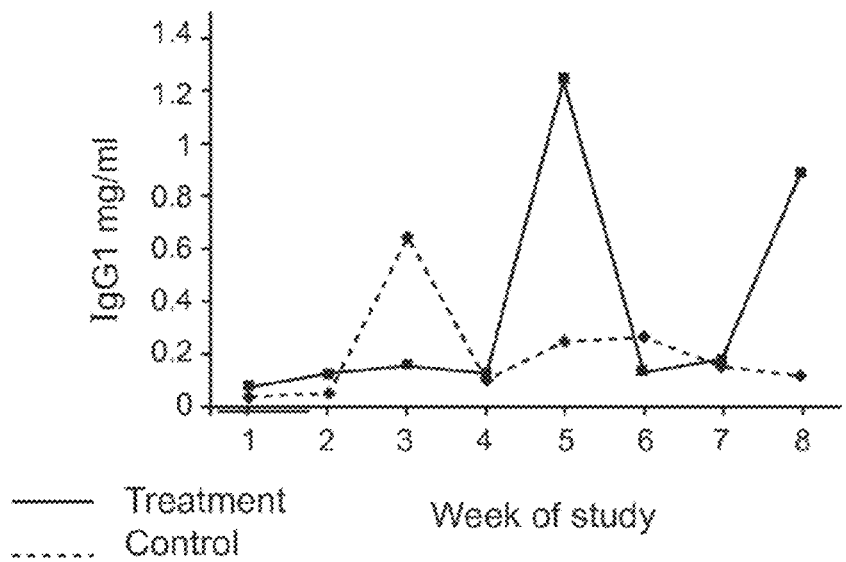
FIGS. 9A and 9B show the results of the non-nosode homeopathic treatment on the IgG levels in a group of Lactating Holstein Cows for Subclinical Mastitis. Based on these results there is an effect even with out the inclusion of nosodes of Example 10.
Figure 9B:
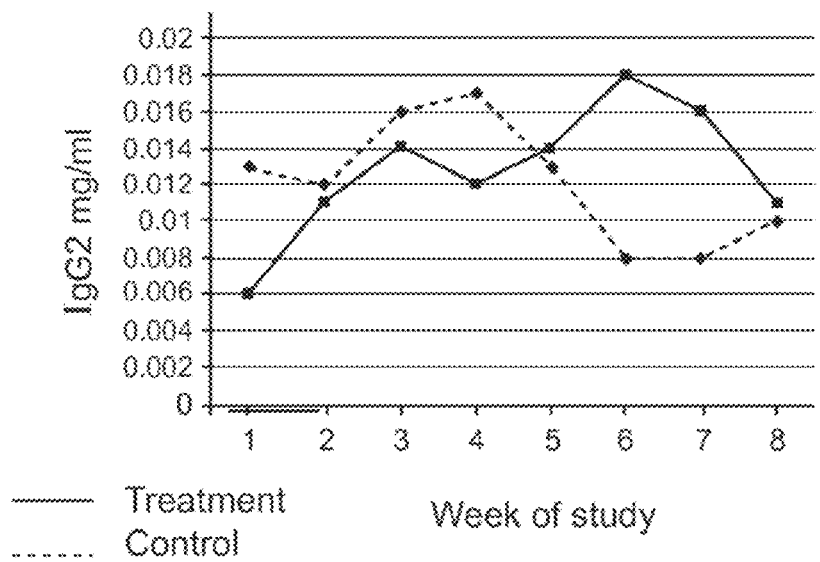

These results show significant effects for $IgG_1$ only. The $IgG_1$ is the only immunoglobulin to show significant change the $IgG_2$ section was affected by the cattle not receiving homeopathy developing mastitis and having to be removed from the trial. This factor was not part of the trial results as it was not part of the parameters to be examined, but the actual incidence of mastitis in the animals not receiving the homeopathic medication was much higher than those who received the homeopathic medication. The change in the significant changes in $IgG_1$ may have been related to the reduced incidence of mastitis. The lack of change in $IgG_2$ may have been related to the masking of this effect by the intrusion of clinical mastitis into the trial in the non homeopathic group-without this there may also have been a change in $IgG_2$. Both IgG's have been associated with mastitis and conferring protection against mastitis in cattle (see FIGS. 9a and 9b).

Conclusion

Applicants found that the actual incidence of mastitis in the animals not receiving the homeopathic medication was much higher than those who received the homeopathic medication. Thus, the conclusion is that an effect in $IgG_1$ was seen while the animals were on homeopathic treatment.

Example 11: Wound Healing Case Study-Accelerated Wound Closure and Healing

Subject: Jack Terrier, Male Neutered, 10 Years Old
Conditions/Symptoms of Subject The patient presented in shock with multiple bite wounds, which were acutely painful, with difficulty in breathing and the danger of an injured trachea temporarily ruled out treatment under general anaesthesia.

Examination of the wounds revealed that the bites had penetrated through the skin to cause substantial damage to the underlying muscles at the junction of the neck and chest between the axillae, around the dorsal aspect of the left foreleg, and over the rib cage on the left side.

Treatment

Initial therapy included clipping the wounded area and washing the skin margins with Hibiscrub surgical scrub followed by povidone iodine. The open wound was then bathed in sterile water with Homeopathic Mother tincture of Calendula (Marigold), at a dilution of 20 drops of mother tincture add to 100 ml of sterile water. The wound was gently dabbed dry and Vet Cream (Core A and Core B in the form of a cream) was liberally applied to the entire affected area and the surrounding tissue close to the wound margin. The owner was instructed to apply the cream to the affected area 2-3 times daily.

When wound treatment was complete the patient was given a single 15 drop dose of Trauma/First Aide Complex. Antibiotic cover was instigated with a single 0.5 ml intramuscular injection of Synulox RTU (Pfizer Animal Health). Maintenance of antibiotic cover was supplied by Synulox 250 mg tablets (Pfizer) at a dose rate of ½ a tablet twice daily for 5 days.

Results

Two days after the initial consultation the tissue around the wounds was obviously bruised, but dramatically less. The painful breathing initially apparent on the day of presentation was considerably better and the fluid from the underlying lacerated muscle layer was draining from the wounds. A decision was taken not to suture the wounds weighing up the benefits of the drainage as well as the absence of sepsis and the dramatic decrease in pain.

Figure 10A:
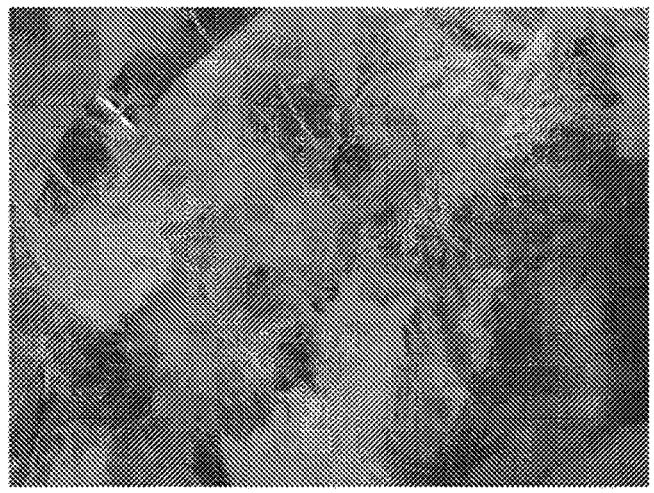
FIGS. 10A to 10C show the dog of Example 11.
Figure 10B:
Figure 10C:

Seven days after the initial attack, the wounds were already closing over and there was no evidence of bruising or local skin damage (see FIGS. 10a to 10c).

Conclusion

The rapidity of healing is very clear where there is a total disappearance of tissue bruising and all surface injuries, other than the major wound points, had literally vanished. In the same period the wound holes themselves had produced healing edges and had filled in the open areas completely. In general with wounds like this one expects sepsis or at the very least a large amount of tissue swelling and bruising that lasts some weeks and that a drain might be required. In a patient with no anti-inflammatory or analgesic treatment (as in this case) one would not normally have expected the patient to be fully mobile in two days.

Example 12: Wound Healing Case-Bite Wound Healing

Conditions/Symptoms of Subject

The patient (canine) originally presented with what was thought to be a self inflicted skin condition from scratching, described as hair coming off with scabby eruptions. However, on further examination this appeared to be like that of a dog that had been savaged and the area around the eye in fact looked like a wound rather than a self inflicted injury.

Treatment

Considering that the initial appearance of the skin resembled that of a traumatic wound, it was decided to treat the presenting signs rather than any underlying condition as no underlying cause could be determined.

Vet Cream (Core A and Core B in the form of a cream) was administered. Sulphur 9x (Sulphur at a dilution 1:10-9) homeopathic was also supplied to be used on a twice daily basis just in case the owners assumption of a parasite cause such as sarcoptic mange was correct and to provide a non steroid anti-puritic effect. However, this was stopped after confirmation from the owner that the wounds were the result of a fight, and administration twice daily of the Vet Cream was continued.

Results

The area below the eye with the open wound had completely disappeared in the intervening five weeks, with no trace of an open area. No trace of any wound was visible on the dorsal area.

Example 13: Wound Healing Case Study-Treatment of a Simple Slow Healing Wound

Subject: Blonde Coated Lurcher, Female Neutered, 14 Months Old
Conditions/Symptoms of Subject The patient was presented three weeks after the initial injury with an incised-type wound that although small just would not heal.

Treatment

No antibiotic cover was provided during treatment, nor were any anti-inflammatoir either topical or oral used during the treatment of this case. The only treatment used from the initial presentation to final cure was Vet Cream (Core A and B in the form of a cream) on a twice daily basis till the wound appeared to be healing and then to apply it once daily.

Within two days of starting the application of Vet Cream the wound had started to heal and the owner reduced application of the cream to once daily. Within six days the wound had healed completely.

Example 14: Wound Healing Case Study

Subject: Greyhound Brindle & White Neutered Male 7 Years Old

Conditions/Symptoms of Subject

The injury was caused by running under a wooden pole and him catching his back on a protruding nut. The skin on the back literally peeled back.

Treatment & Results

The wound was repaired under general anaesthesia 0.1 ml Acetylpromazine 2 mg/ml IM as premed and Thiopentone 2.5% IV to effect (15 ml used) as a knockdown dose and anaesthesia was maintained with Halothane. There was 90 minutes of surgical time excluding the time taken for preparation of the wound for surgical repair which included clipping the area and washing the skin margins with Hibiscrub surgical scrub followed by povodine iodine. The open wound was then bathed in sterile water with Homeopathic Mother tincture of Calendula (Marigold) at a dilution of 20 drops of mother tincture add to 100 ml of sterile water. The wound was then sutured using mattress sutures to appose the edges, as the patient had a history of tearing wounds open. The large areas which were unattached to the underlying facial tissue were tacked down using single interrupted sutures to enhance the chances of reattachment. A decision was taken not to insert a drain into the wound initially. When wound repair was complete the patient was given a single 15 drop dose of Trauma/First Aide. Antibiotic cover was instigated with a single 2.5 ml intramuscular injection of Synulox RTU (Pfizer). Maintenance of antibiotic cover was supplied by Synulox 250 mg tablets (Pfizer)×15 at a dose rate of 11/2 tablets twice daily.

Vet Cream (standard combination Core A and B in the form of a cream) was liberally applied to the entire affected area and the surrounding tissue close to the wound margin. The owner was instructed to apply the cream to the affected area 2-3 times daily. The patient had an uneventful recovery despite the degree of degloving and the extent of the wound and the previous history of the patient's wounds breaking down. The antibiotic cover was not extended beyond the initial 5 days and no analgesic or anti-inflammatory other than the Vet Cream was used. There was no wound breakdown nor was there any need for a drain in the wound despite its extensive size, which is a common event with injuries such as this.

Example 15: Severe Bruising (Case with Two Fractured Legs)

Subject-Labrador Cross Retriever Male 1 Year Old

Condition

Both hind legs were fractured as a result of a car impact. The damage done to the car indicated that the patient was lucky to be alive.

The endotracheal tube used to intubate the patient during anaesthesia was covered in blood indicating severe damage not just to the legs but also to the lungs with some degree of pneumothorax.

Treatment

The subject received three doses of Trauma/First Aid in the first twenty four hours, and then once daily for three days. The entire bruised area had a formulation of Vet Cream (Core A and Core B) applied on a daily basis for the first five days. The subject was also placed on Clindamycin 22 mg/Kg twice daily for the initial 5 days but no anti-inflammatory or analgesic drugs were required.

By the end of the 5 day treatment period the subject was considered recovered to the point of being able to support weight on the legs. The subject also removed his sutures after less than twenty four hours following presentation, but as the wound remained closed this healed uneventfully despite the severe bruising of the immediate tissue. This case indicates that the Trauma/First Aid treatment promoted rapid healing, promoted extremely rapid resolution of the wounds, bruising and fractures. What is unexpected for an injury such as this is the speed of recovery and the disappearance of all bruising in less than 6 days such that the subject was able to put weight on both back legs.

Example 16: Use of Anti-Infective Core a for Paw that was Golf Ball Sized Due to Bite Abscess Subject: Cat 3 Years Condition: Injured Paw with Bite Abscess Treatment Core A at a low C potency was administered to the subject in liquid form for oral mucosal administration.

| Remedy | Concentration Vol/Vol % | Potency |
|---|---|---|
| Hepar Sulphuris | 25% | 6c |
| Lachesis | 25% | 6c |
| Mercurius Solubilis | 25% | 6c |
| Silica | 25% | 6c |

Figure 11A:
FIGS. 11A to 11B show the cat's paw and comparably sized golf ball of Example 16.
Figure 11B:
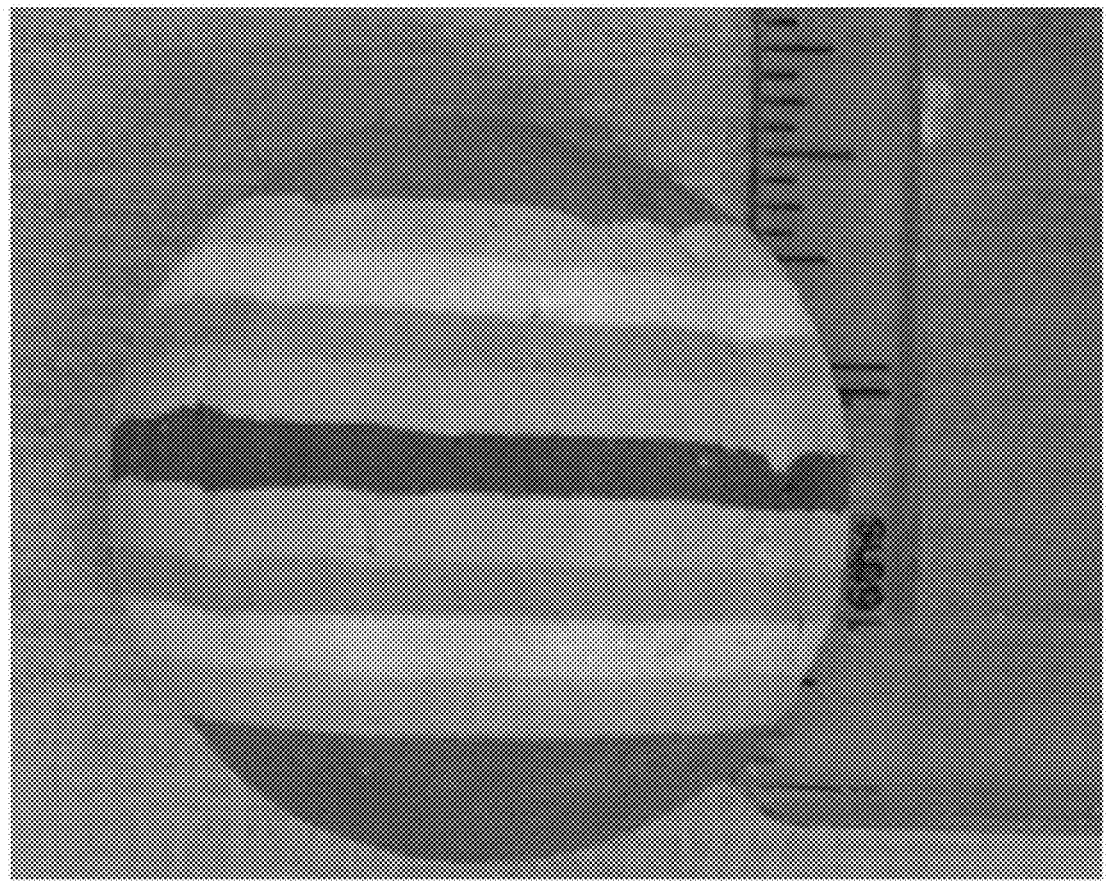

The above homeopathic complex was supplied in a base of 20% alcohol and 80% water, as well as second base of 30% glycerine and 70% purified water. Both were administered to the same patient to assess if any difference in efficacy could be noted and both worked equally well. The paw on Day 1 is shown in FIG. 11a, and FIG. 11b shows a comparably sized golf ball.

At day 10 the subject was putting equal weight on both feet.

Example 17: Use of Anti-Infective Core A

Figure 12A:
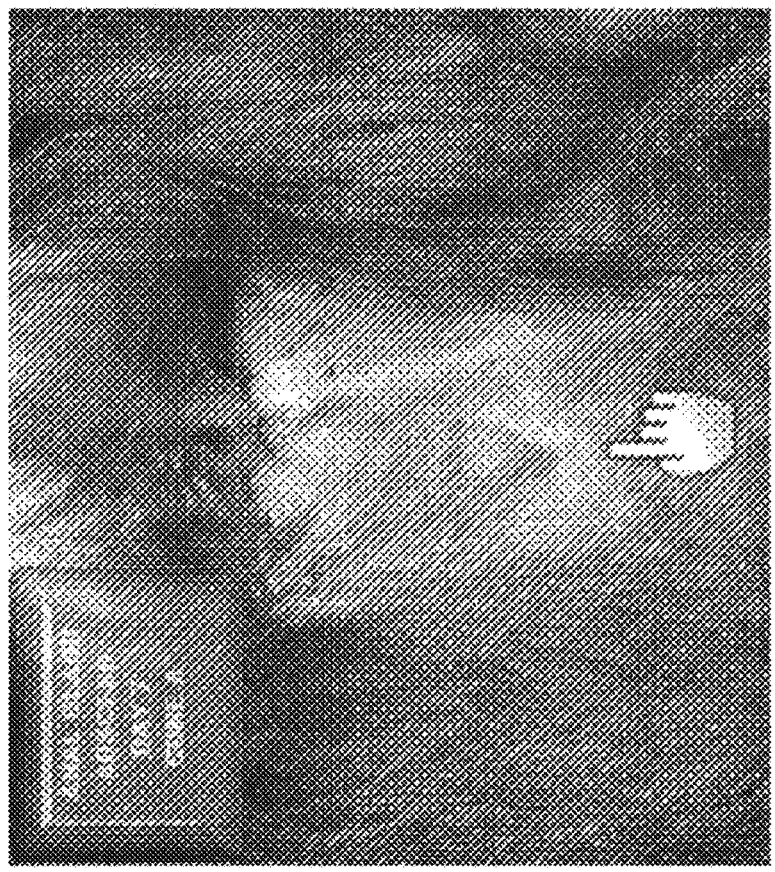
FIGS. 12A and 12B show the dog of Example 17.

Subject & Condition:

Canine presented with anal gland abscess. FIG. 12a shows, on Day 1, an Anal Gland Abscess (arrowed) in the Left anal gland where the whole L side of the peri-anal area was extremely swollen and a sinus was discharging pus Treatment The pus was cleaned away from the sinus and the midline and showed how much the area was swollen. The patient was given Core A only in high potency, above 200c, for oral administration.

| Remedy | Concentration Vol/Vol % | Potency |
| --- | --- | --- |
| Hepar Sulphuris | 25% | 200c |
| Lachesis | 25% | 200c |
| Mercurius Solubilis | 25% | 200c |
| Silica | 25% | 200c |

The above homeopathic complex was supplied in a base of 20% alcohol and 80% water, as well as second base of 30% glycerine and 70% purified water. Both were administered to the same patient to assess if any difference in efficacy could be noted and both worked equally well.

No other form of medication (including antibioitics) was used.

On Day 3, the wound was no longer discharging pus and the swelling in the area was vastly reduced.

Figure 12B:

As the abscess had cleared, a Vet Cream (comprising Core A and Core B in the form of a cream) formulation was applied to the affected area to enhance the healing. FIG. 12b shows the anal gland abscess on Day 7 which had completely cleared and the sinus was completely closed. 4 days after administration of Vet Cream complete resolution of the wound had occurred. Both the speed of abscess and wound resolution in this case were remarkable.

Example 18

Subject & Condition

A surface tissue injury to the left thumb of a human subject caused by the trapping of the thumb between a power hose and a granite stone.

Treatment

The injury was treated with Vet Cream (Core A and Core B in a cream) which was liberally applied to the entire affected area and the tissue immediately surrounding the wound margin.

Within 24 hours following treatment with Vet Cream Formulation the left thumb showed a significant degree of healing allowing the subject to continue to work manually with dirt and water and no protective covering on the wound. Despite regular immersion in water during the subject's work day, the wound healed further (data not shown).

Two days from the initial injury and after a full day's work again, which includes manual labour and immersion in water while being unprotected, it was observed that further rapid healing had occurred despite it being on a point of flexion where healing is usually much slower.

Less than one month after the original injury (Day 27), the wound was entirely healed despite continuous manual work and daily immersion in water.

This example demonstrates how effective the Vet Cream Formulation is in treating human injuries as well as animals under even more rigorous conditions than would normally be expected, as the wound was on a flexing region and was immersed daily in water and subjected to hard manual work.

Example 19

Subject & Condition

The subject presented with severe bruising and pain around the ankle joint and foot immediately after a hamstring injury.

Treatment

Trauma/First Aid treatment was taken three times in the 8 hours post injury and Vet Cream (Core A and Core B in a cream formulation) was applied to the area of the injury and the area of subsequent bruising.

The cream was applied twice daily for 3 days in morning and evening and then daily for 3 days. After that the cream was applied approximately every 2nd day twice daily.

A similar injury had occurred to the opposite leg a few years previously which took in excess of 6 weeks to recover and walk without a leg stocking to keep down the oedema, swelling, and bruising. In this case where the subject was treated with the Trauma/First Aid treatment and Vet Cream Formulae, the subject was walking reasonably comfortably by the 7th day post injury, and by the 15th day post injury the subject was back cycling despite the fact that the initial assessment of the injury was much worse.

Example 20: Wound Healing Case Study-Treatment of a Septic Compound Fracture and Accompanying Wound Subject: Black and White Domestic Shorthaired Cat MN less than 1 year old Conditions/Symptoms of Subject The subject had been presented to two different veterinary surgeries. The first veterinary surgeon had given Betamox LA (suspension containing 150 mg/ml amoxycillin as Amoxycillin Trihydrate BP) at the correct dose of 15 mg per kg bodyweight and was given further antibiotic cover provided by a single long acting injection of Convenia at the correct dose of 8 mg cefovecin/kg body weight (1 ml/10 kg body weight of) by a second veterinarian surgeon. About 24 hours after returning to his carers the wound started to discharge pus again, but it was decided to wait as the patient was on Convenia and improvement might still occur. However, the wound continued to discharge purulent material.

Treatment

Figure 13C:

On initial presentation the affected region produced a profuse purulent discharge, which was foetid in odour, when pressed and the whole area felt like it might slough due to the purulent undermining. The femur could be felt under the skin and had obviously penetrated through the wound site, before slipping back in giving a compound fracture. The wound was flushed with Calendula & Echinacea Mother tincture diluted at a rate of 20 drops (1 ml) per 100 ml of Sterile water and 1 ml of Antirobe (clindamycin hydrochloride) 100 mg/ml. The subject was also injected with Antirobe (clindamycin hydrochloride) 100 mg/ml at a dose rate of 22 mg/Kg. A request was put in to the original veterinary practice for a full case history and x-rays, which are shown in FIGS. 13c and 13d.

The condition of the leg following a 2nd flushing with Calendula Echinacea and Clindamycin solution was improved, with the discharge being less purulent. However, some small clots of pus and necrotic debris could still be seen in the serous discharge that still came profusely from the wound.

A decision to surgically repair the leg, if possible, was taken. FIG. 13f shows that some of the muscle shearing caused by the distal portion of the femur which perforated the skin had become septic.

Pre-surgery the subject was put on a daily injection of Antirobe (clindamycin hydrochloride) 100 mg/ml at a dose rate of 22 mg/Kg. The subject was anaesthetised using xylazine and ketamine as knock down agents and maintained in isoflourane. A decision to try and repair the leg was taken at this point and surgical intervention was under taken to attempt a full reduction of the fracture site. When the lower portion of the femur was exteriorised both veterinarians involved in the surgery were absolutely taken aback by the absolutely foetid odour of the distal femur, particularly the bone marrow. A decision was taken remove as much bone marrow as possible and then to wash out the cavity with a homeopathic complex consisting of Echinacea, Hepar Sulph, Calendula, Symphytum and Gunpowder in various potencies, chosen on the basis of the foetid odour and the osteomyelitis. 500 I of Clindamycin 100 mg/ml was also introduced into the cavity. An intramedullary pin of a size smaller than would normally be used was introduced into the upper fragment of the femur and then into the lower portion of the femur resulting in a complete reduction of the fracture. Crystapen as a white soluble dry sterile powder, containing 95.7% w/w Sodium Benzylpenicillin BP, for reconstitution (with Water for Injection Ph. Eur), in bottles containing 5 mega-units (3 g) at a dose of rate of 10 mg/Kg and Antirobe (clindamycin hydrochloride) 100 mg/ml at a dose rate of 22 mg/Kg. were introduced directly around the fracture site. The wound was then closed with simple interrupted cat gut sutures for the internal layers and the skin wound was sutured using polyamide sutures.

FIG. 13a and FIG. 13c show the post surgical wound site with Vet Cream applied and it shows the sinus tract to the infected bone. Immediately post surgery 10 drops of Trauma/First Aid treatment was given.

Post surgical care involved cage rest for 26 days. Initially twice daily applications of Vet Cream were done, a 10 day course of Clindamycin 100 mg/ml at a dose rate of 22 mg/Kg IM, a 5 day course of Silica 200c homeopathic in liquid Solution was administered at a dose rate of 5 drops twice daily. Subsequent to stopping the treatment, the subject was started on Calc Phos homeopathies in high potency daily for 3 days to improve bone healing and Symphytum in low potency was administered twice daily at a different time of day for 10 days. Both were administered away from food.

Twenty four hours after surgery the patient's wound was already healing well and the sinus had actually closed. Probiotics and Prebiotics were given for the first 10 days and neither anti-inflammatoires nor were analgesics administered. The subject was attempting to walk from the next day, which is a common result where Trauma/First Aid has been used with Vet Cream. Just two days after surgery, the subject was standing unsupported on the injured leg and the large open wound is already starting to heal. Also, it was noticed that with Vet Cream treatment, hair re-growth is enhanced as well as wound repair.

As the subject developed a liking to the taste of the Vet Cream, it was necessary to simply apply the Vet Cream just as the subject was being fed. In addition, the subject was still being given Clindamycin daily, probiotics, Vet Cream a course of Silica 200c at this point.

FIG. 13b demonstrates that merely 11 days post surgery, the subject's wound has dramatically healed. What is also of note is the level of hair re-growth as can be seen when compared to FIG. 13a.

At this point it was decided to temporarily stop applying the Vet Cream and allow the wound to heal as it was doing. What was remarkable was that little healing took place over the next 10 days. As such, Vet Cream was reapplied daily for a couple of days which once again promoted not just rapid healing but further hair growth prior to the subject's discharge.

Conclusion

Both veterinarians and the nurse involved had not expected this case to resolve following surgical intervention based on the incredibly foul sepsis at the time of the surgery. Apart from all the other factors mitigating against recovery, the initial lack of response to antibiotic cover and the introduction of a foreign substance in the form of an intramedullary pin into such septic circumstances would normally further add to the difficulty in having any success in clearing up the sepsis. The results obtained were completely unprecedented.

Furthermore, in a large number of cases enhanced tissue regeneration has been seen with hair regrowth. Such enhanced tissue regeneration appears to extend to septic bone healing in this case. The patient returned to normal function extremely rapidly demonstrating an analgesic effect, a tissue restoration effect covering hair skin, muscle, connective, and bone tissue while at the same time enhancing organ function recovery.

Example 21

A 9 year old female, spayed SharPei/Lab Mix that was hit by a snow plow. She also suffers from epilepsy and SharPei Fever. She was far enough on her driveway that it only severed the lateral 2 digits off her right front paw.

The results from the HP Vet Cream (Aconitum Napellus 3×, Arnica Montana 3×, Arsenicium lodatum 6×, Belladonna 3×, Bellis Perenis 3×, Bryonia 3×, Calendula Offcinalis 3×, Chamomilla Matricaria 3×, Exchinacea Angustifolia 3×, Exchinacea Purpurea 3×, Graphites 8×, Mamamellis Virginia 3×, Hepar Sulphuris 3×, Hypericum Perforatum 3×, Lachesis 8×, Ledum 3×, Millefolium 3×, Mercurius Solubilis 6×, Phytolacca 6×, Ruta Graveolans 3×, Rhus Toxicodendron 3×, Silica 3×, Stellaria Media 3×, Sulfur 3×, Symphytum 3× And Thuja 3×) were very impressive. The owners started with daily sugar bandages for 11 days, then switched to daily furacin bandages for 10 days, and HP cream for 14 days.

Figure 14A:
FIGS. 14A to 14G show the dog of Example 21.
Figure 14B:
Figure 14C:
Figure 14D:
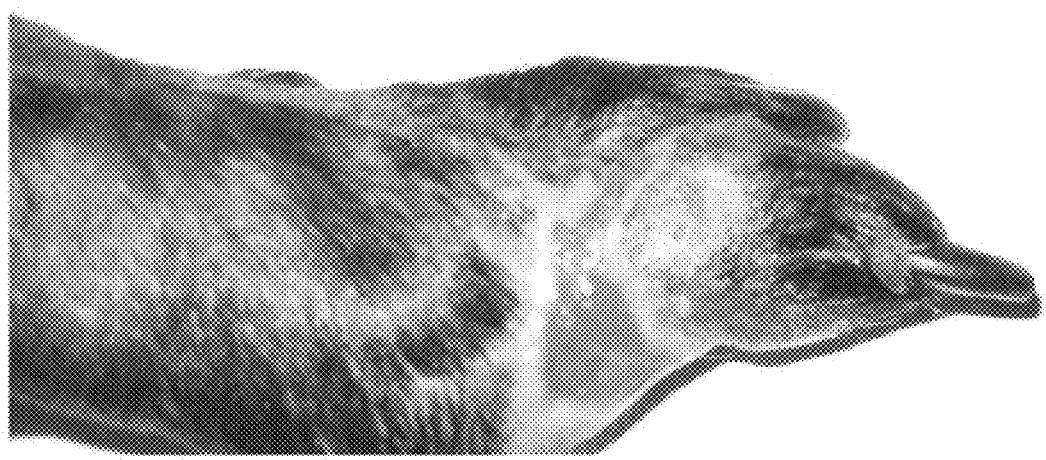
Figure 14E:
Figure 14F:
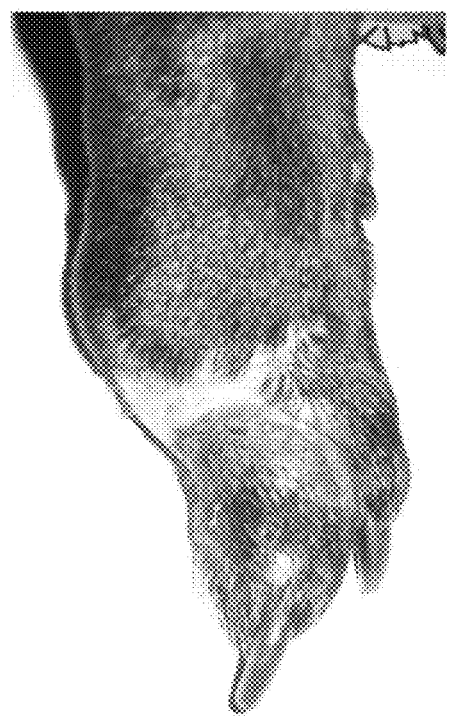
Figure 14G:
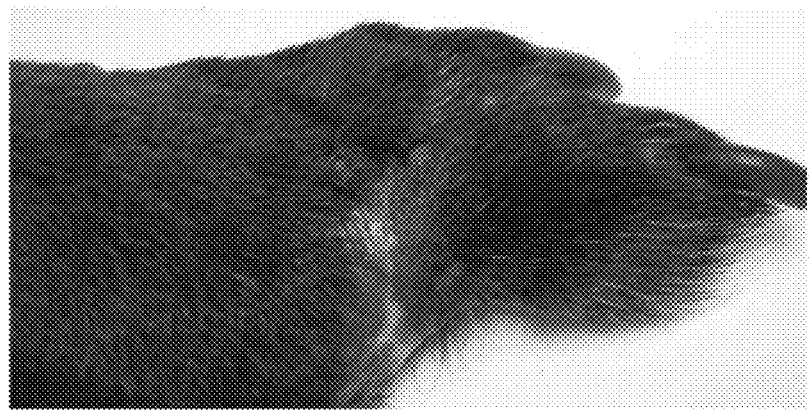

The results are depicted in FIGS. 14A-14G. FIG. 14A depicts the initial accident, FIG. 14B depicts the furacin bandages started and Baytril for 14 days, FIG. 14C depicts the efucain bandages stopped and the HP healing cream started, FIG. 14D depicts 6 days after HP cream started, FIG. 14E depicts 14 days after HP healing cream was started, FIG. 14F depicts one month after HP healing cream was started and FIG. 14G depicts three months after the initial trauma. As indicated in FIG. 14G, the wound is almost completely healed three months after the initial trauma.

Example 22: Wound Healing Case Studies: Integrating a Homeopathic Approach with Conventional Medicine for Favourable Outcomes The primary focus of skin lesion management is thorough removal of all foreign material and of all devitalized or contaminated tissue. Effective debridement can reduce but not completely eliminate the concern about infections. To this end, it is a clinical judgement as to the need for antibiotic therapy, and if used whether it should be applied topically, administered systemically or a combination of both. Additionally, sutures and/or bandaging can help provide protection and structural support that will facilitate wound healing. Nonetheless, even for the most skilful veterinarian, some wounds and non-traumatic skin lesions just will not heal.

One aspect of wound healing on which few data are available concerns the use of homeopathic treatments. Whether as part of routine wound management or in situations of refractory wounds, homeopathic remedies can be a valuable addition to the clinician's armamentarium. To this end, a homeopathic cream has been developed and tested clinically to determine its utility in clinical practice. The following example presents a number of case studies that suggest that use of the cream facilitates wound healing in dogs in a range of varied situations.

Case Study 1: Trauma-Induced Foreleg Injury in a Bichon Frise

After being hit by a car, a 7 year-old, male, neutered Bichon Frise suffered a penetrating wound through the full depth of the dermis of the medial aspect of the left forelimb, extending from the proximal metacarpus to the axilla. Radiological examination indicated no bone damage had occurred and there were no additional injuries. Under general anesthesia, the hair bordering the wound was clipped and the wound debrided. However, the extent of skin damage, and high risk of wound contamination and secondary infection precluded suturing. Topical antibiotic was applied, the wound was bandaged and the patient was sent home on daily oral trimethoprim (5 mg/kg)/sulphadiazine (25 mg/kg), and carprofen tablets (2 to 4 mg/kg/day).

Three days later, the dog was bright, but there was no evidence of healing, and an extensive malodorous, purulent discharge had matted the hair beyond the border of the wound. The owner rejected a second general anaesthetic, but the dog's docile temperament allowed cleansing of the wound with a water/antiseptic solution and povidone iodine. The dog was sent home with owner instructions to keep the wound as clean as possible using saturated salt water. Five days later, the wound had not improved and the antibiotic was changed to 50 mg clindamycin twice daily, and the owner was instructed to clean the wound with a homeopathic mother tincture calendula (marigold) twice daily (20 drops in 100 ml of sterile water).

Figures 15A, 15B, 15C, 15D, 15E:
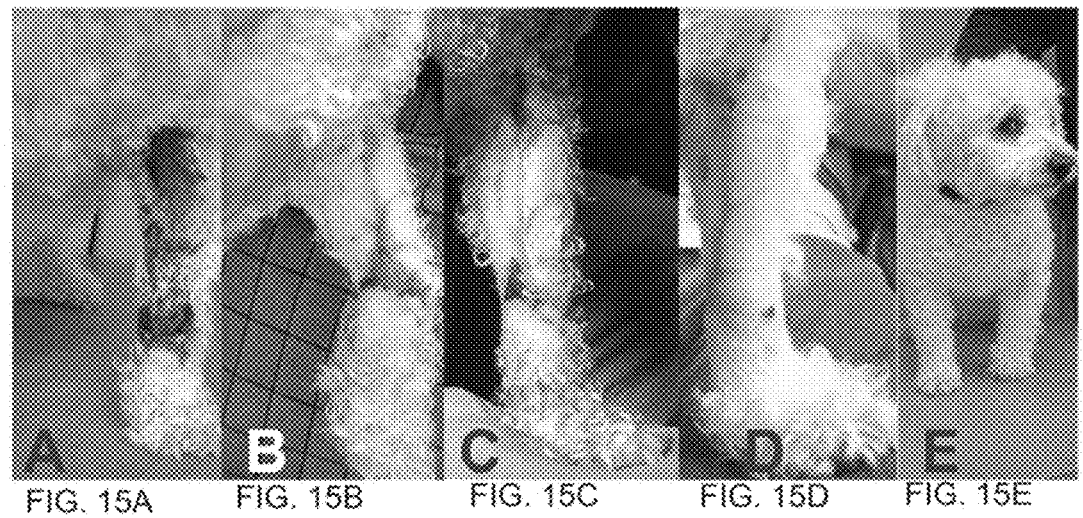
FIGS. 15A-E depict the dog of Case Study 1 of Example 22. A. Wound condition prior to general anaesthesia, 2 weeks post injury. B. 6 days post second anesthetic procedure and initiating therapy with HP Vet Cream. C. 6 days, and D. 21 days post second anaesthetic procedure and initiating therapy with HP Vet Cream. E. Approximately one year later.

Two weeks after the initial injury (FIG. 15A), healing was not occurring and the wound continued to emit an odour. The dog was again anesthetized and the wound was clipped, cleaned and bathed in the homeopathic mother tincture calendula and tension sutures were placed, systemic antibiotic therapy was halted and the owner consented to trial a developmental homeopathic cream (HP Vet Cream®). After the wound had dried the cream was liberally applied along with antibiotic ointment. Twenty days after the initial injury, and 6 days after the second anaesthetic there was substantial improvement (FIG. 15B), and from this point the owner ceased all other treatment, but continued applying the cream (FIGS. 15C and 15D). Approximately one year after the accident, the dog showed complete healing with minimal scarring and almost complete hair regrowth (FIG. 15E).

Case Study 2

Figures 16A, 16B, 16C:
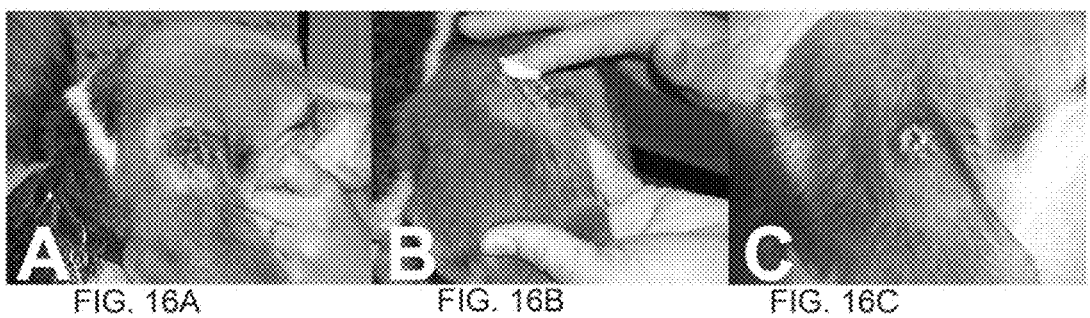
FIGS. 16A-C depicts the dog of Case Study 2 of Example 22. A. Clipped lesion on right pinna on day of presentation, B. Application of HP Vet Cream to the ear. C. 10 days post initial presentation with substantial healing.

A 4 year old neutered male Beagle presented with a persistent, circular, purulent wound with necrotic skin on the right pinna (FIG. 16A). Although the etiology was unknown, the owner suspected that the wound originated from a spider bite. The dog was administered systemic antibiotic (penicillin injection), and the owner was provided with amoxicillin and HP Vet Cream for application twice daily for one week (FIG. 16B). The dog was re-presented 10 days later for a recheck when the wound was significantly reduced in diameter with no sign of infection (FIG. 16C). The owner was advised to continue applying the cream and the dog recovered uneventfully.

Case Study 3

Figures 17A, 17B, 17C:
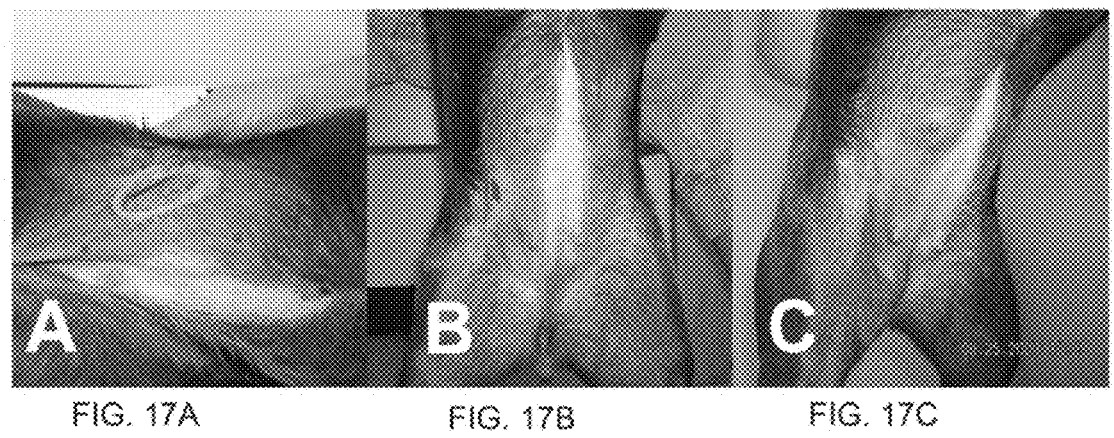
FIGS. 17A-C depict the dog of Case Study 3 of Example 22. A. Right inguinal penetrating wound on the day of presentation, B. Following twice daily application of the homeopathic cream, the wound showed progressive improvement after B., 2 weeks, and C. 4 weeks of treatment involving only the application of HP Vet Cream.

A 2-year-old female crossbreed dog was presented with an open wound in the right inguinal area that penetrated through the superficial muscle layer (FIG. 17A). The wound appeared clean and antibiotics were not considered necessary. HP Vet Cream was the only treatment advised, to be applied to the wound twice daily. FIG. 17 shows the progressive improvement in the condition of the wound at 2 weeks and 4 weeks post initial presentation.

Case Study 4.

Figures 18A, 18B, 18C:
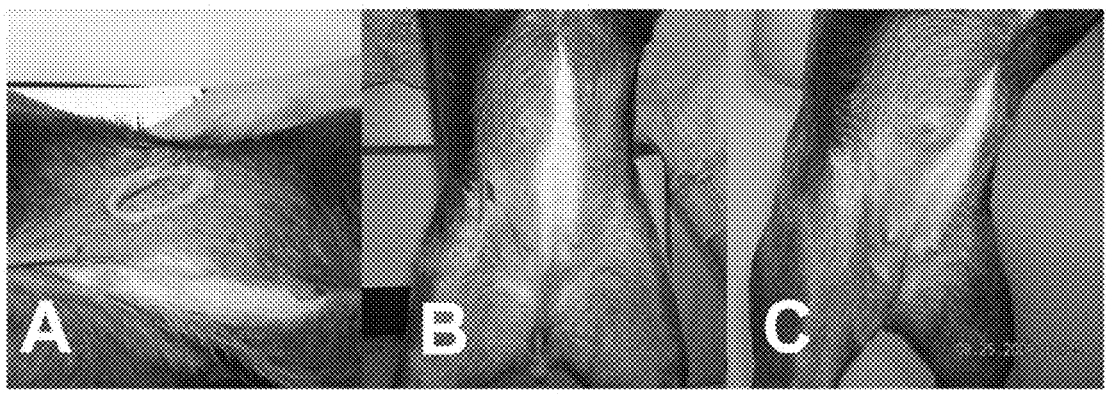
FIGS. 18A-C depict the dog of Case Study 4 of Example 22. A. Wound on the ventromedial surface of the stifle on the day of presentation, with evidence of infection. B. The wound at 2 weeks after initial presentation following a course of amoxicillin/clavulanic acid and twice daily application of HP Vet Cream. C. 4 weeks post initial presentation, with the homeopathic cream the only intervention during the previous 2 weeks.

A 6 year-old spayed female, mixed breed dog presented with an open wound on the medial aspect of the left stifle. The wound was approximately one inch in diameter and appeared inflamed and granulomatous (FIG. 18A). The dog was given an injection of penicillin and the owner dispensed 2 weeks supply of amoxicillin/clavulanic acid tablets. As adjunctive therapy, HP Vet Cream was applied, and dispensed for twice-daily application. At examination 2 weeks later, the wound was almost completely healed with new hair growth present and no evidence of infection (FIG. 18B). The only treatment advised at this time was to continue twice daily application of the homeopathic cream. Two weeks later, the wound appeared to be completely healed (FIG. 18C).

Case Study 5.

Figures 19A, 19B, 19C, 19D:
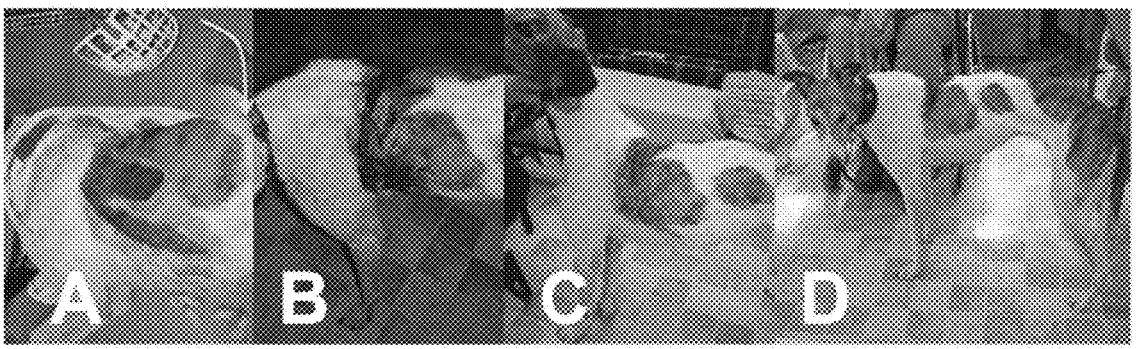
FIGS. 19A-D depict the dog of Case Study 5 of Example 22. A. Photograph of the anesthetized dog's severe dorsal skin wound on presentation. B. 24 hours post surgical repair and application of HomeoPet Vet Cream. C. 21 days post surgery D. 1 year post surgery.

A neutered, 7 year-old male greyhound suffered an extensive full depth skin shearing injury of the dorsum by running under a pole from which there was a protruding nut. The extent of affected skin area is shown by the arrow in FIG. 19A. The wound was debrided and cleaned under general anaesthesia, including bathing in sterile water with homeopathic mother tincture of calendula (marigold) at a dilution of 20 drops of mother tincture add to 100 ml of sterile water. Mattress sutures were inserted to appose the wound edges, with supporting subcutaenous sutures. Antibiotic cover was instigated with intramuscular amoxicillin/clavulanic acid and maintained with twice daily oral administration for 5 days. HP Vet Cream was liberally applied to the affected area and the owner (a veterinary nurse) was instructed to apply the cream to the area at least twice daily. At follow up visits the dog appeared to be recovering well and at a routine visit 12 months after the surgery, the wound was seen to have healed well.

In describing four separate cases of trauma induced wounds, this paper demonstrates the potential for integration of a homeopathic cream into conventional approaches to managing a range of skin lesions presented for veterinary treatment. In the first case, a wound that was refractory to initial conservative treatment with debridement and antibiotic showed rapid improvement following a change in antibiotic and the application of HP Vet Cream. Similarly, a combination of antibiotic with HP Vet Cream (Case Study 4) produced a good healing response in an infected stifle wound, and in the most severe wound (Case Study 5), a comprehensive surgical intervention, combined with topical and systemic antibiotic administration and at least twice daily application of HP Vet Cream produced a full cure.

Not all traumatic wounds described in this paper required supporting antibiotics—in one case of (Case study 3), a deep penetrating wound responded quickly and thoroughly to application of HP Vet Cream without any additional therapy. One case report (Case study 2) described the favourable response of a wound of unknown origin to combined therapy with the HP vet cream and topical antibiotic.

In case studies such as those described in this paper, it is not possible to define which of a number of interventions produced a cure, or if it was the exact combination of components together that was responsible. However, the positive healing response in which HP Vet Cream was used alone (Case study 3) does suggest that it offers properties that can enhance wound healing. Regardless, the cases reported here raise expectations that HP Vet Cream, as either a single agent or in combination with other topical and systemic therapies such as antibiotics, has the potential to be a valuable addition to the clinician's armamentarium, whether or not surgery and suturing is utilized.

Example 23: Additional Case Studies

The disclosures of the case studies on www.homeopet-pro.com are hereby incorporated by reference.

Case #142: 4 yr Old Neutered Male Beagle

Figure 20A:
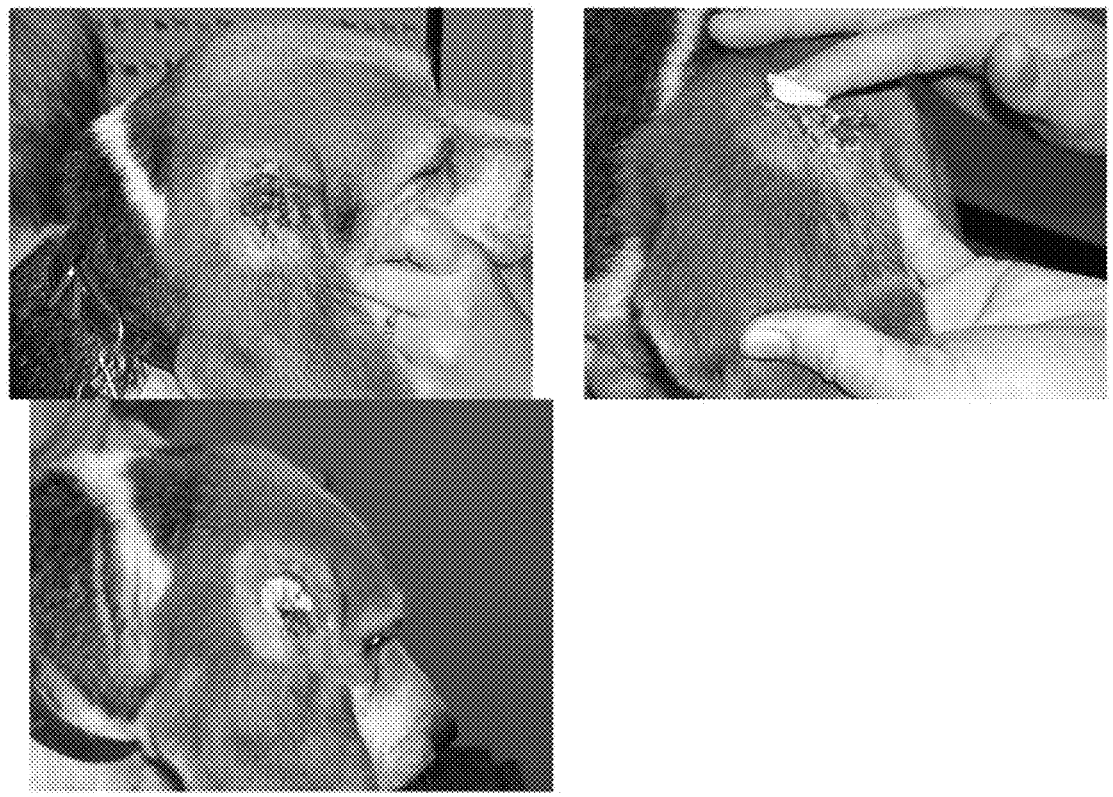
FIGS. 20A-B depict the animal of Case Study 142 in Example 23.
Figure 20B:

Patient presented with a "sore" on right pinna. It was suspected that the wound was from a possible spider bite. Wound was a circular wound with necrotic skin and pus exuded. Patient was given an injection of penicillin. Wound was clipped and scrubbed with beta dine solution. Patient was sent home with Amoxitabs twice daily for one week. The Homeopet cream was prescribed for two times per day. Pictures taken are illustrated at FIG. 20A. Patient returned 10 days later for a recheck visit. Wound was significantly reduced in diameter and infection was not present. Owner was advised to continue Homeopet cream. Photo taken is shown at FIG. 20B.

Figure 21A:
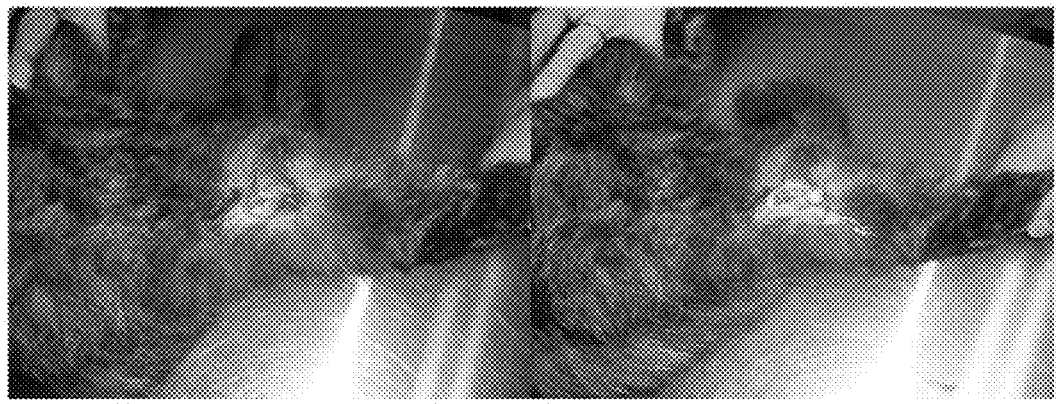
FIGS. 21A-B depict the animal of Case Study 143 in Example 23.
Figure 21B:

Case #143 1 ½ yr old spayed DSH feline Patient presented as non-weight bearing on right front leg. Upon further examination an open, infected, necrotic wound was found. Leg was previously swollen per owner before bringing patient in. Wound was approximately the size of a nickel. Patient was given a convenia (antibiotic injection) and Homeopet cream prescribed. Photos taken are shown in FIG. 21A. Patient was brought in for a recheck visit after 2 weeks. Wound was almost completely healed. Infection was not present and fur was already growing back. Wound was approximately the size of a pea and basically just scabbed over. No further treatment except Homeopet Cream was advised. Photos taken are shown in FIG. 21B.

Case #144 2 yr Old Unneutered Shih Tzu Mix

Figure 22:
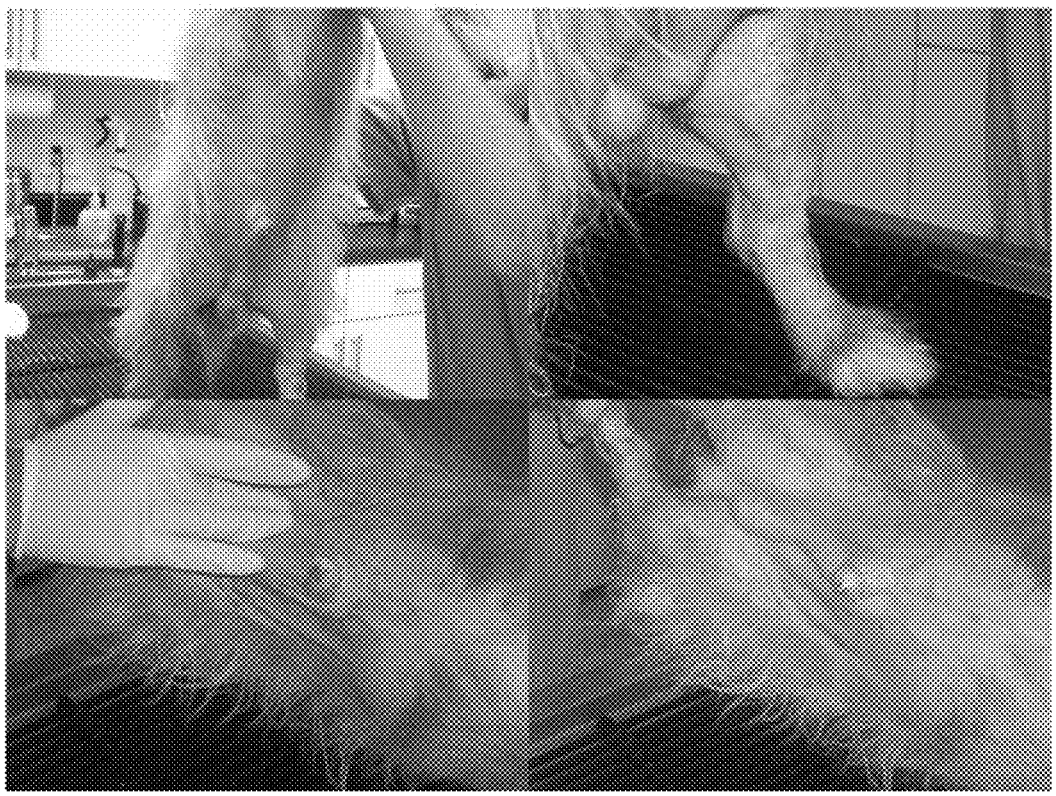
FIG. 22 depicts the animal of Case Study 144 in Example 23.

Patient presented after being hit by a car. Oxygen was given and IV cath was placed. PCV & Total Protein values were obtained. Patient was sedated with Ketamine and Domitor. X-rays were taken. No significant problems were noted on the x-rays. Abrasions were clipped and cleaned with beta dyne solution. Patient was given an injection of penicillin and metacam. The abrasions were treated with Homeopet Cream. The patient was sent home the following day with pain medication (Novox 75 mg) and Homeopet Cream twice daily for the multiple abrasions in the inguinal area. Owner was advised to bring patient in two weeks for a recheck visit. Photos taken are shown in FIG. 22.

Case #145 2 yr Old Female Mix Breed Canine

Figure 23A:
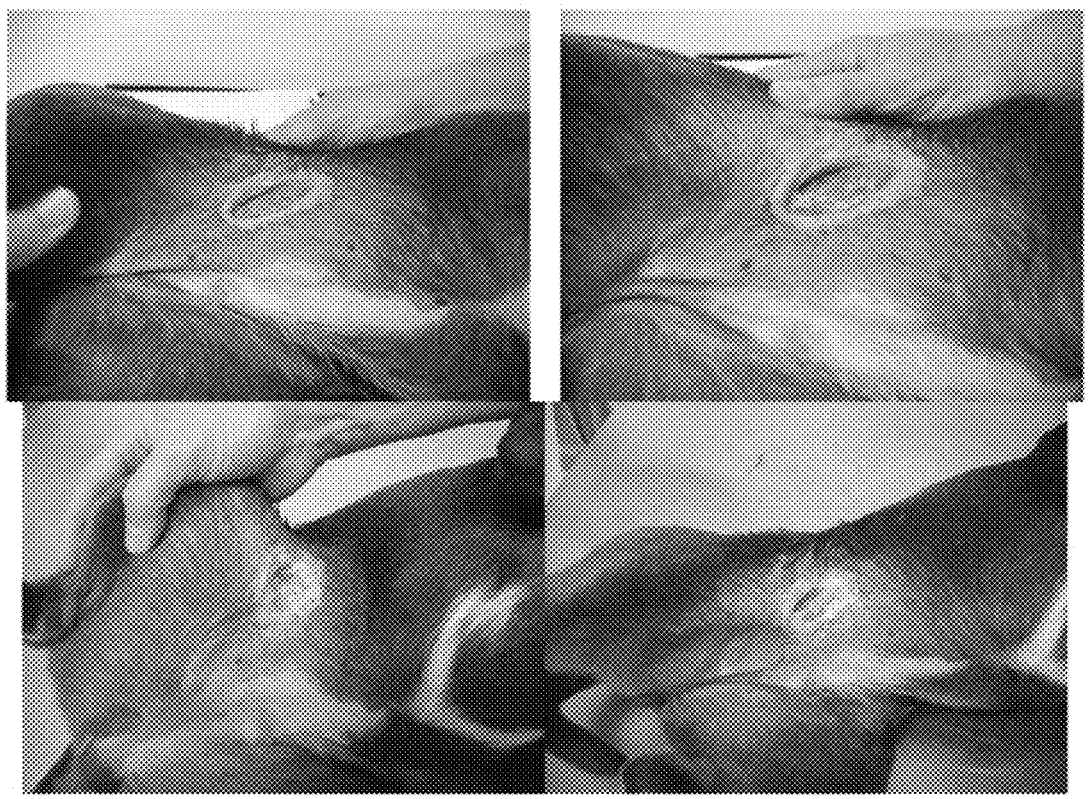
FIGS. 23A-C depict the animal of Case Study 145 in Example 23.

Patient presented with a wound on the right back side. The wound was granulating, non-smelly but open wound in right inguinal. It was suspected possibly a knife injury-had separation of muscle fibers. Homeopet Cream was the only treatment advised. Patient received Homeopet Cream twice daily. Photos taken are shown in FIG. 23A.

Figure 23B:
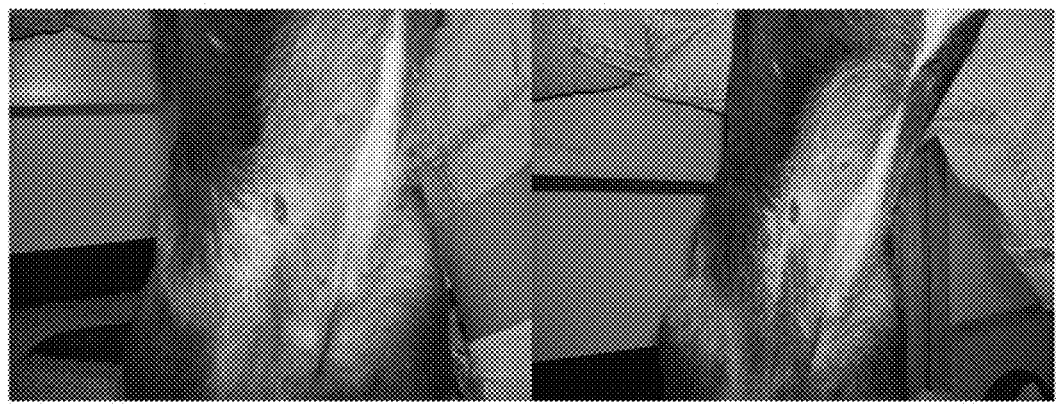
Figure 23C:

Patient returned 2 weeks later for recheck visit. Wound healing well. Photos taken are shown in FIG. 23B. In a recheck visit 2 weeks later, the wound was completely healed at this date. A small scar was present; fur was already trying to come in and cover where wound used to be. Photos taken are shown in FIG. 23C.

Case #146 6 yr Old Spayed Female Canine (Brown)

Figure 24A:
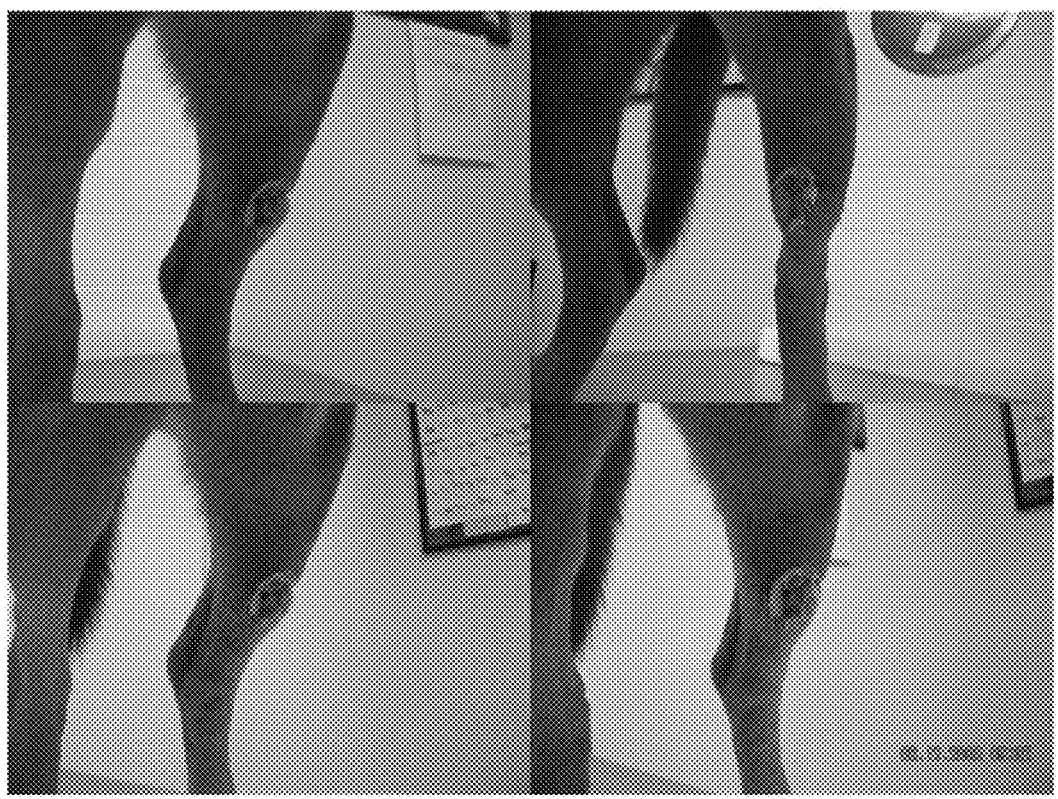
FIGS. 24A-C depict the animal of Case Study 146 in Example 23.

Patient presented with an open wound on inside of left rear leg, possibly from a metal shingle. Wound was quarter sized and very inflamed. The patient was given an injection of penicillin and put on Clavamox for 2 weeks. Homeopet Cream was advised and given 2 times daily. Photos taken are shown in FIG. 24A.

Figure 24B:
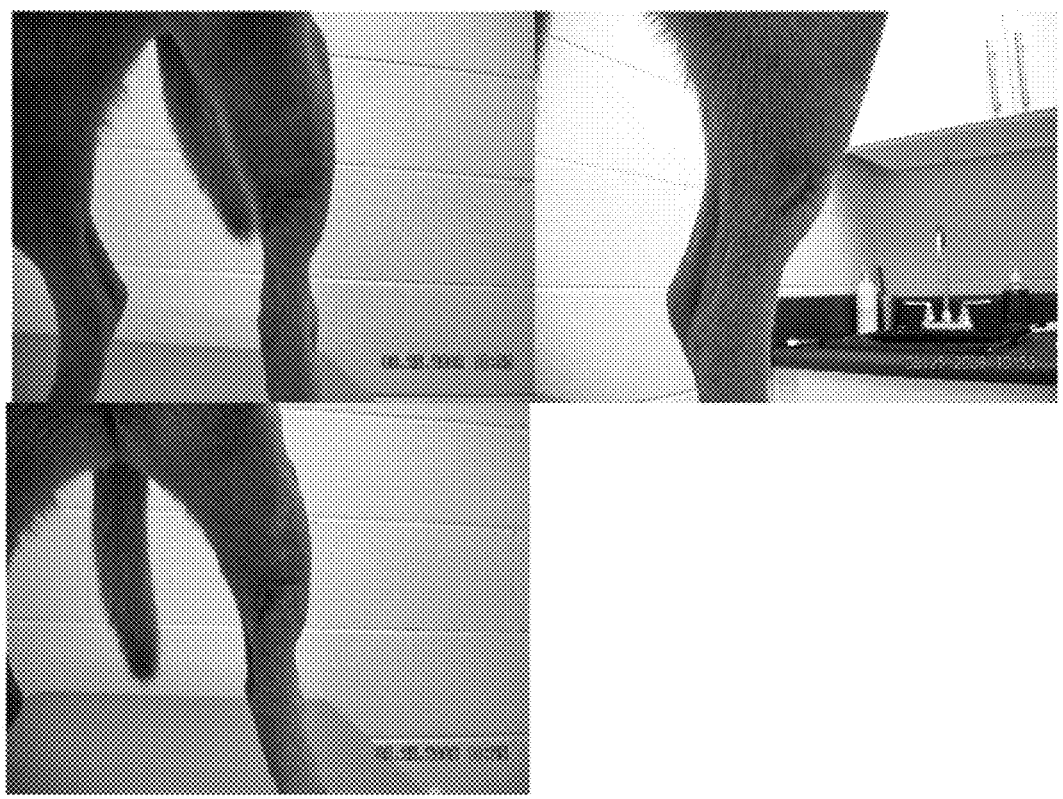

Patient returned 2 weeks later for a recheck visit. Wound was almost completely healed. New hair growth was present. Wound was now dime sized and healing very well. No infection was present. The only treatment advised at this time was to continue the Homeopet Cream. Photos taken are shown in FIG. 24B.

Figure 24C:
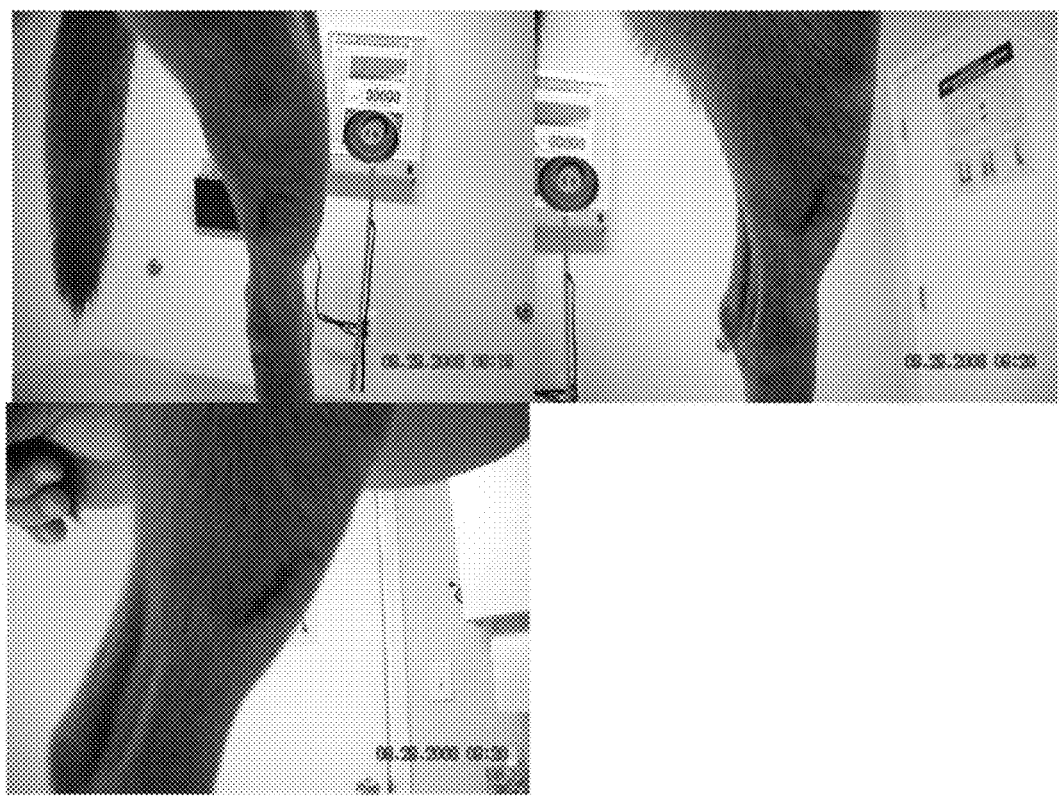

The patient returned 3 ½ weeks later. The wound was healed and a small scar present. Photos taken are shown in FIG. 24C.

Case #147 10 yr Old Female/Spayed Collie

Initial Exam: Presented red inflamed, malodorous skin. The patient also had difficulty in getting up and down—in obvious pain. A deep pyoderma and a decubitus ulcer were found on the right elbow. There were multiple papules and pustules all over skin. The patient was in obvious pain as the ulcer was on a pressure point on the elbow.

Figure 25A:
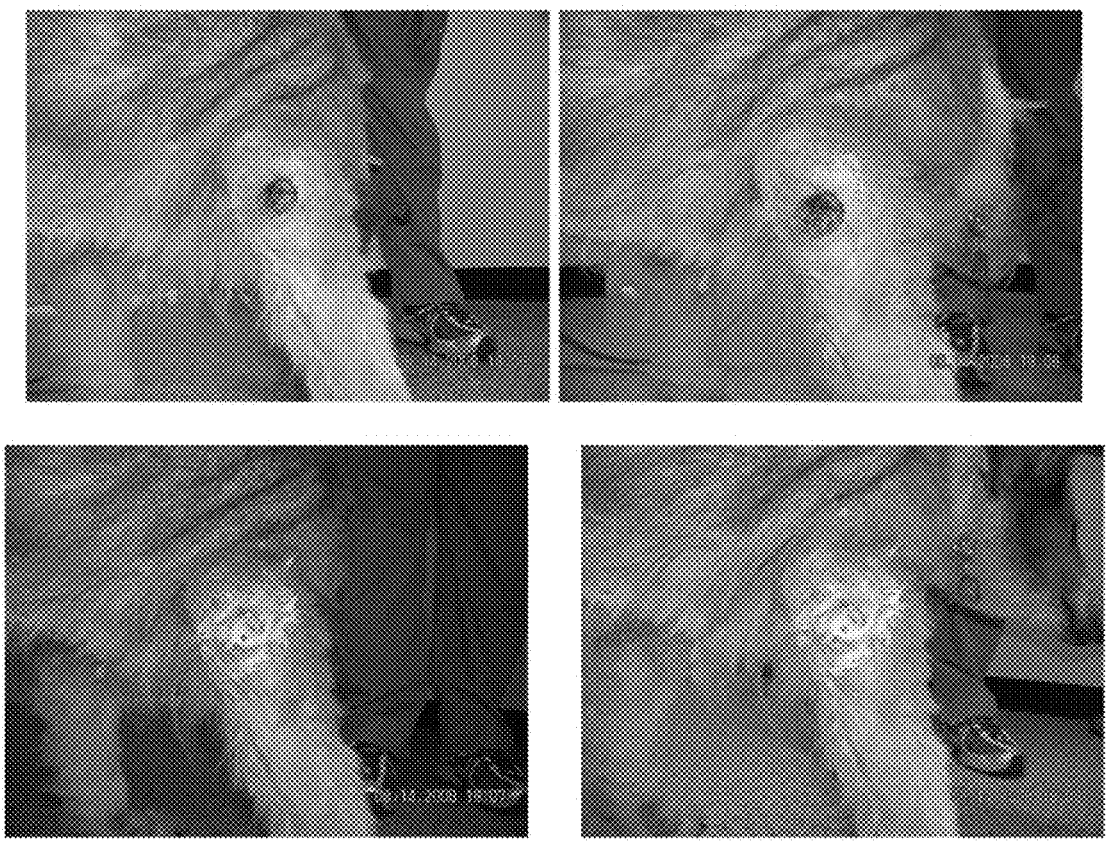
FIGS. 25A-C depict the animal of Case Study 147 in Example 23.

The patient was given an injection of penicillin and prednisone. Patient was sent home with follow up antibiotics and prednisone tablets. The Homeopet vet cream was advised to be used two times daily. Photos taken are shown in FIG. 25A.

Figure 25B:
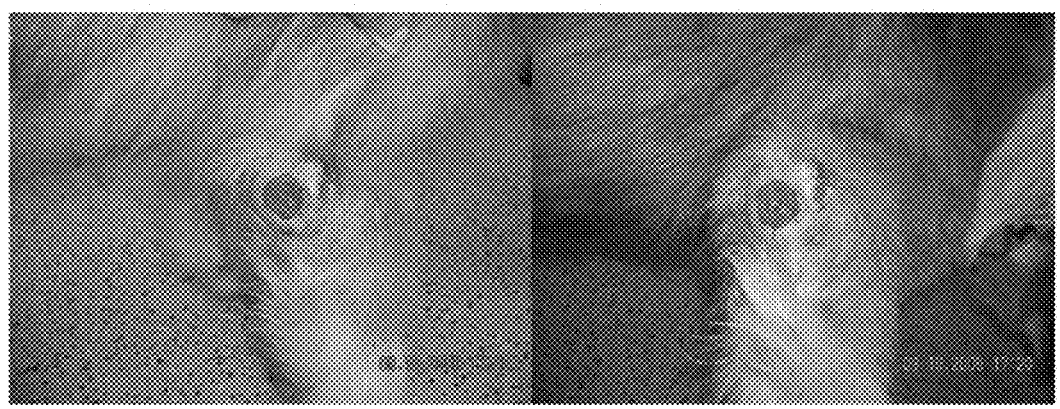

Patient came in for a recheck visit after 3 weeks. The area on right elbow was slightly improved. Patient was still scratching constantly. New hot spots were forming on the right hip and rump. Patient was given another injection of steroid (Depo Medrol) and penicillin. Patient was sent home with 2 more weeks of antibiotics and prednisone tablets. Photos taken are shown in FIG. 25B.

Figure 25C:
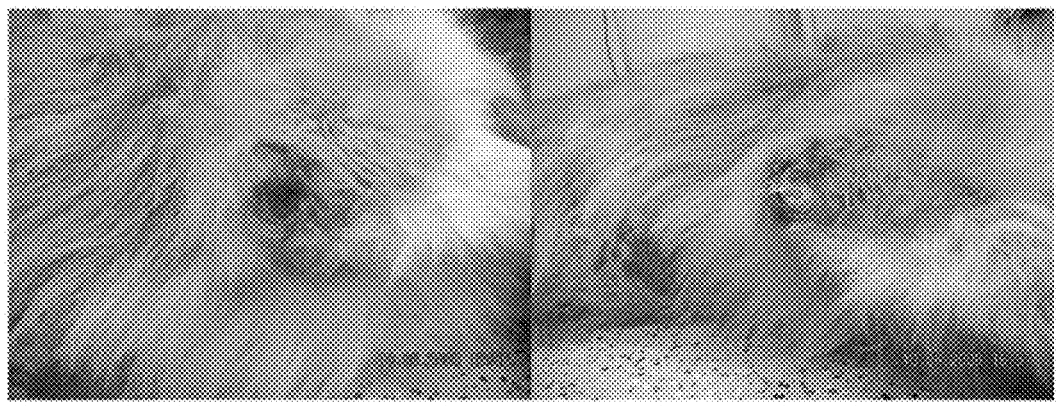

Patient came in for another recheck after 3 more weeks. Foul odor, scabs and sores were still present on skin. The ulcer on right elbow was still present but not as deep. Patient was sent home with more prednisone tablets. A new antibiotic was started on this date (Primor 100 mg). Patient also was given another steroid injection (Dep Med). A second bottle of Homeopet cream was sent home with the patient. Patient was advised to do a recheck visit in 30 days and never returned. Photos taken are shown in FIG. 25C.

Case #148 6 Mth Old Spayed Female Miniature Pinscher

Figure 26A:
FIGS. 26A-C depict the animal of Case Study 148 in Example 23.

Patient presented with dewclaw incision site open. The patient had an ovarian hysterectomy and front dewclaw removal 5 days prior. The dewclaw incision site opened presenting open wounds. The wounds were open, red and dime sized. The dewclaw surgery site on both front paws was open but granulating well. The patient was enrolled in the Homeopet Cream study. The owner was advised to apply the Homeopet cream to both dewclaw surgery sites twice daily. This was the only treatment advised. Photos taken are shown in FIG. 26A.

Figure 26B:
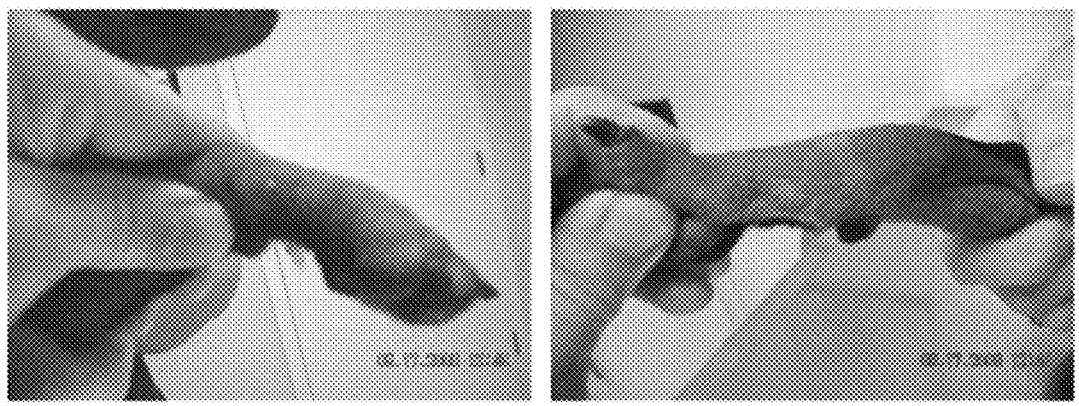

The patient was brought in 2 weeks later for a recheck. The wounds were almost completely healed-now pea sized. The fur was almost completely regrown. The owner was advised to continue Homeopet Cream. Photos taken are shown in FIG. 26B.

Figure 26C:
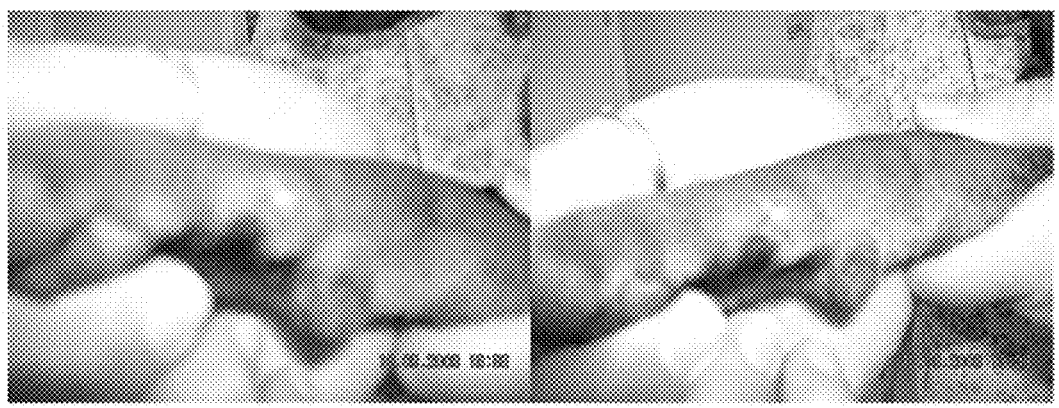

The patient returned 3 weeks later for another recheck. Small scars were present but wounds were completely healed. Photos taken are shown in FIG. 26C.

Case #149 4 Mth Old DSH Kitten

Figure 27A:
FIGS. 27A-B depict the animal of Case Study 149 in Example 23.
Figure 27B:
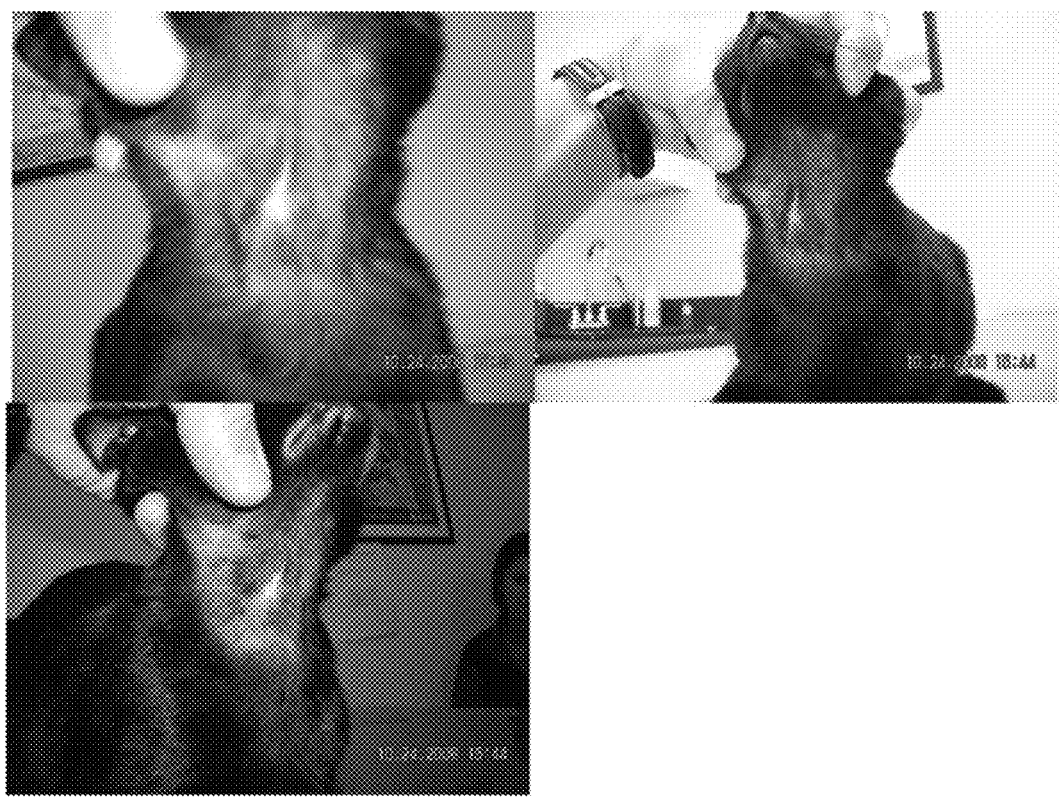

Patient was presented with a possible wolf wound on ventral neck. Wound presented was open (½ dollar sized) with muscles exposed and odor present. The patient was sedated with 25 mg Telazol. The wound was clipped, scrubbed with Technicare. The patient received an injection of penicillin and Metacam. Patient was started on Amoxi Drops twice daily and Homeopet Cream. The patient's rear right leg was bandaged so that the patient would not be able to cause more damage from scratching at wound. Photos taken are shown in FIG. 27A. Patient returned 2 ½ weeks later for a recheck visit. The wound was almost completely healed with small scar present. Fur was already growing in and wound was ¼ the original size. No further treatment but Homeopet Cream was advised. Photos taken are shown in FIG. 27B.

Example 24: Human Studies

Figure 28A:
FIGS. 28A-B depict a patient of Example 24.
Figure 28B:

A 33 year old Male patient with stage 3 renal failure and childhood diabitices had a non responsive ulcerated wound on the left foot is depicted in FIG. 28A. The wound had been treated with conventional, antibiotics, Hyperbaric chamber, formal surgical wound debridement and wound edge cleaning treatments over a three year period with no success. After just five weeks of once daily treatment with Eycnan LL's Nan's Healing Cream, (the name of the present invention employed in the human market), the improvement is shown in FIG. 28B. This level of response is both dramatic and unexpected based on the lack of response to previous treatments clearly demonstrates that the cream is as effective in humans as it is in animals.

Figure 29A:
FIGS. 29A-C depict a patient of Example 24.
Figure 29B:
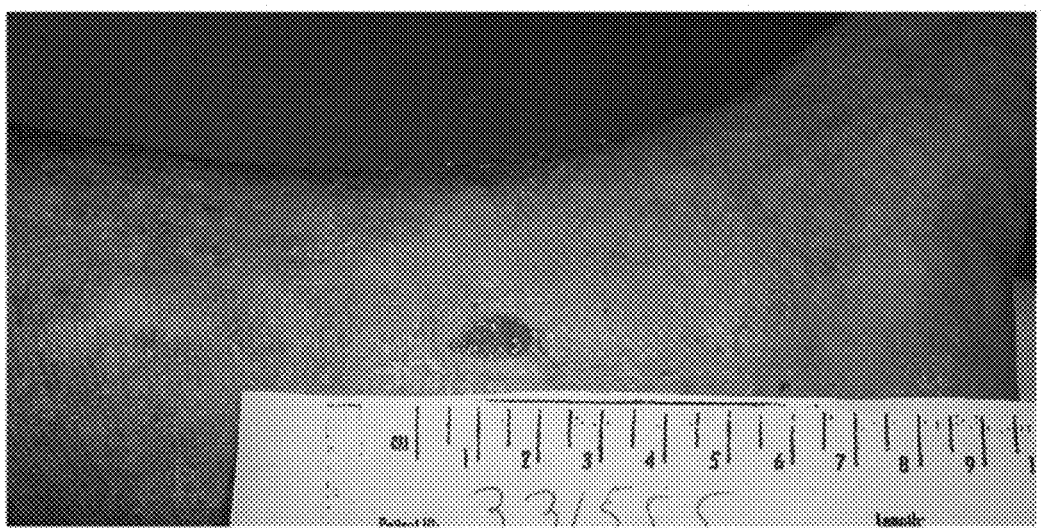
Figure 29C:

An 53 year old male patient with a chronic non responsive wound that was treated with conventional antibiotic coverage and Hyberbaric chamber, formal surgical wound debridement and wound edge cleaning treatments over a one year period with no success depicted in FIG. 29A. After $3^{rd}$ week of cream and compression dressing, the improvement is shown in FIG. 29B. The improvement after an additional week is depicted in FIG. 29C. The wound closure in just four weeks is based on once daily application of the cream in the wound center.

Figure 30A:
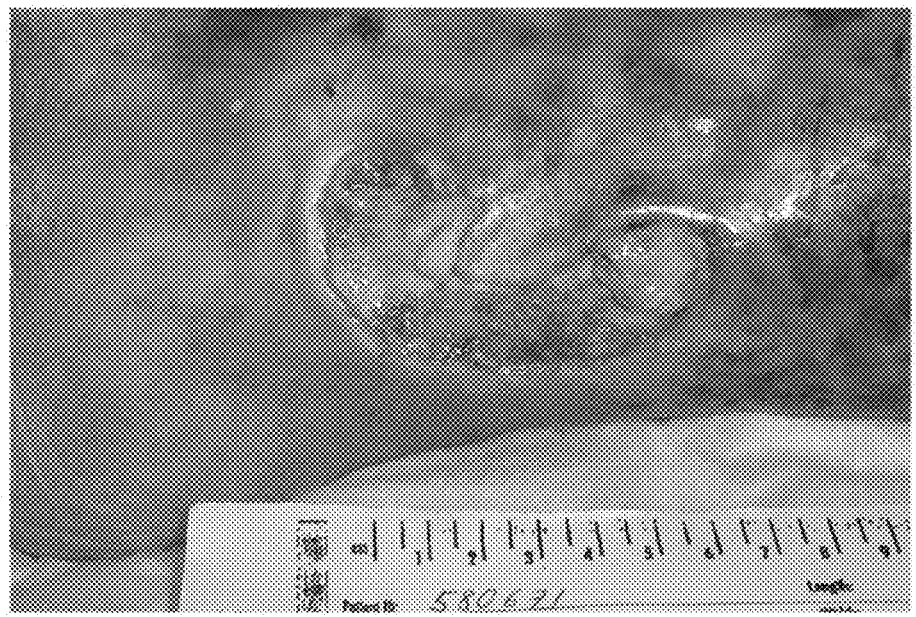
FIGS. 30A-E depict a patient of Example 24.
Figure 30B:
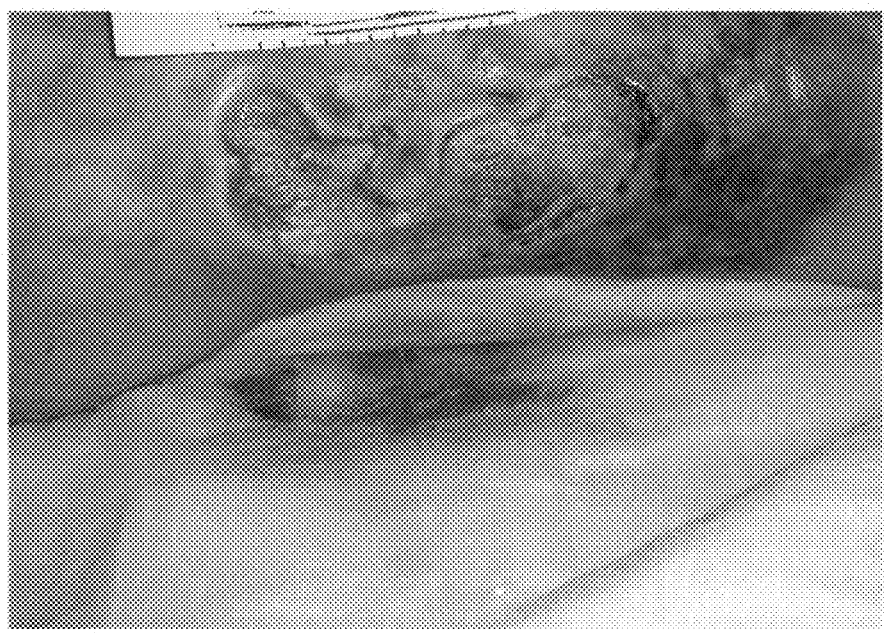
Figure 30C:
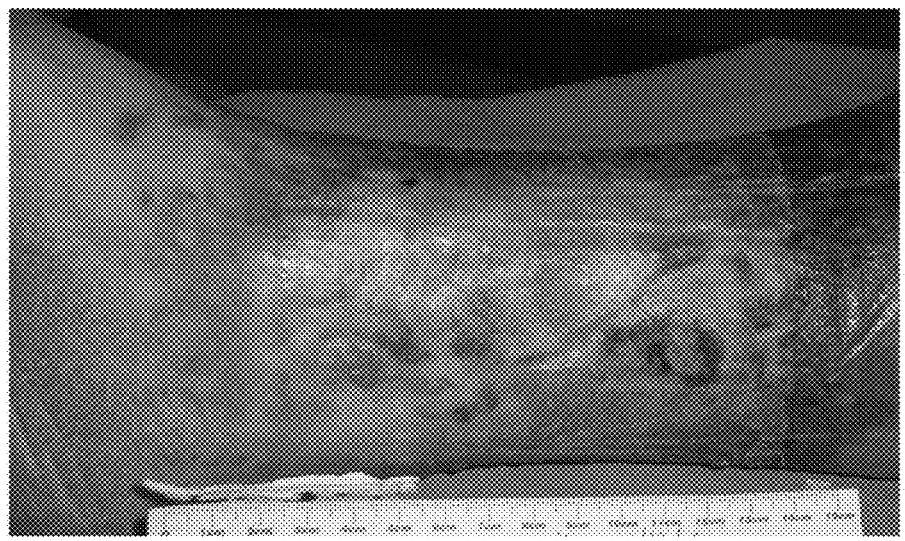
Figure 30D:
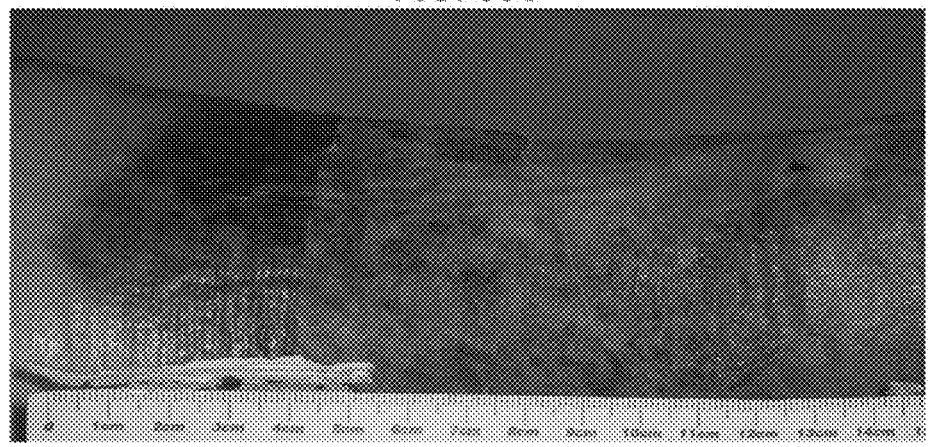
Figure 30E:

An 83 year old male patient with a chronic non responsive wound to the right leg was treated with conventional antibiotic coverage and Hyberbaric chamber, formal surgical wound debridement and wound edge cleaning treatments over a one year period along with alternating wet to moist compression bandaging is depicted in FIG. 30A. The next week, cream with compression dressing was added as depicted in FIG. 30B. The improvement after the fourth week of treatment is depicted in FIG. 30C. During the 6th week of treatment, compression dressing is no longer needed as shown in FIG. 30D. The improvement two months after the depiction in FIG. 30A, is shown in FIG. 30E.

Example 25: HomeoPet Pro HP Healing Cream Case Studies

The cream of the present invention, as exemplified by the present example, has proven to be effective on previously non-responsive wounds. The cream creates a protective barrier around a wound and may be used on open or bandaged wounds. The cream also possesses anti-infective actions, has no known negative drug interactions, is anti-inflammatory and has no known contraindictions. The cream is in a safety sealed tube for ease of application to a wound site.

Figure 31A:
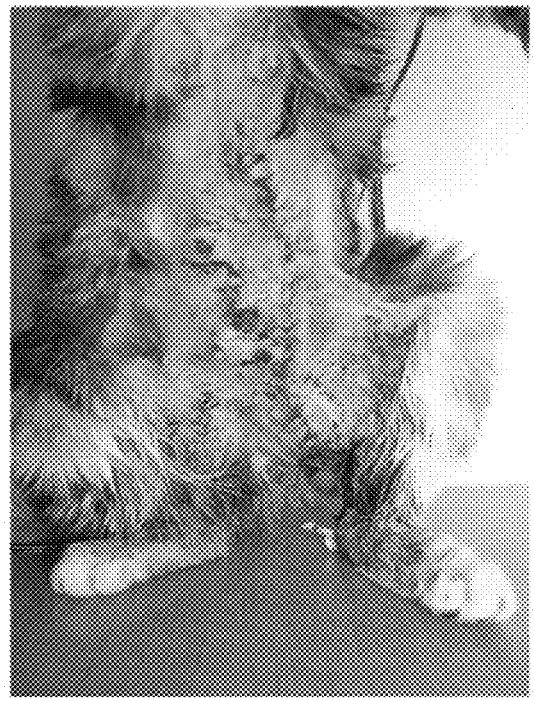
FIGS. 31A-B depict a patient of Example 25.
Figure 31A:
Figure 31B:
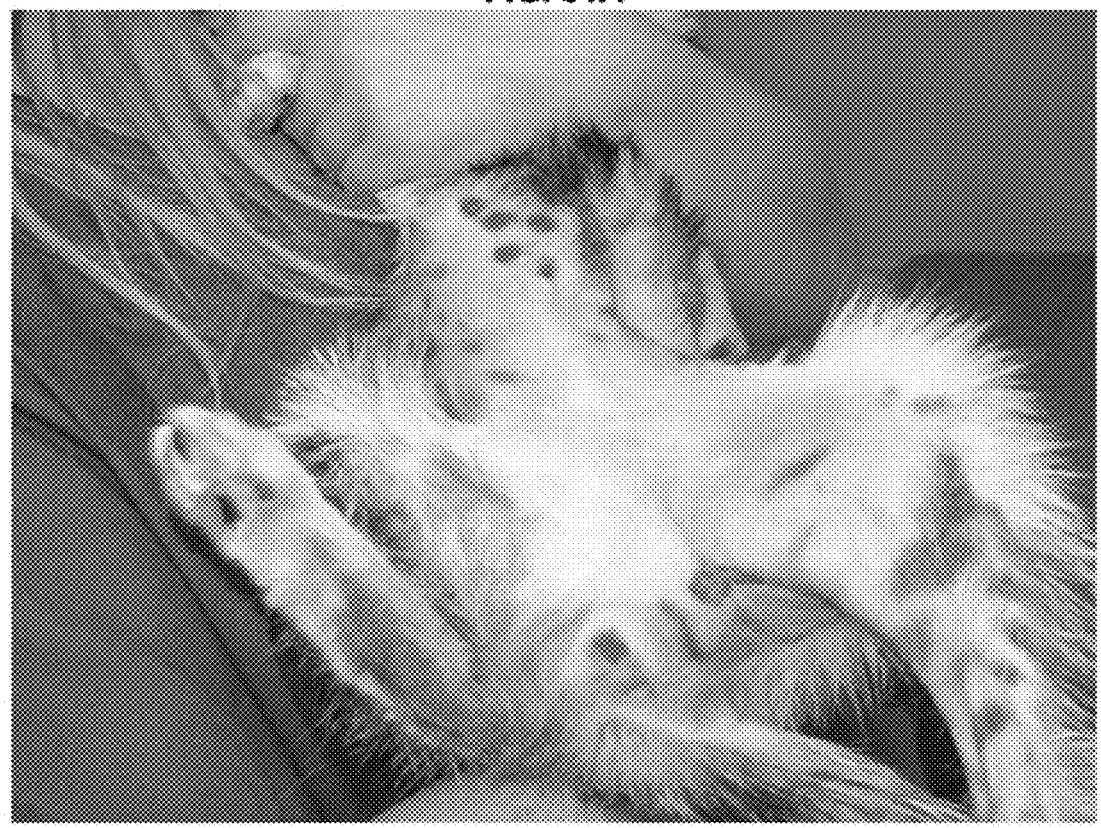

The healing effect is transferred over the entire wound. As shown in FIG. 31A, septic post surgical mastectomy wound healing with a large area of slough due to purulent under run of skin tissue which was non responsive to the initially selected antibiotic cover in a patient with a febrile state. FIG. 31B demonstrates that the response of this patient to just the use of HP Anti-infective Solution and HP Vet Cream in a case which was non responsive to Convenia was to say the least dramatic and provides an opportunity for the treatment of non-responsive cases in the future. Not just did the treatments deal with infection, but they brought this case from a pretty hopeless state to complete cure in less than twenty one days.

Figure 32A:
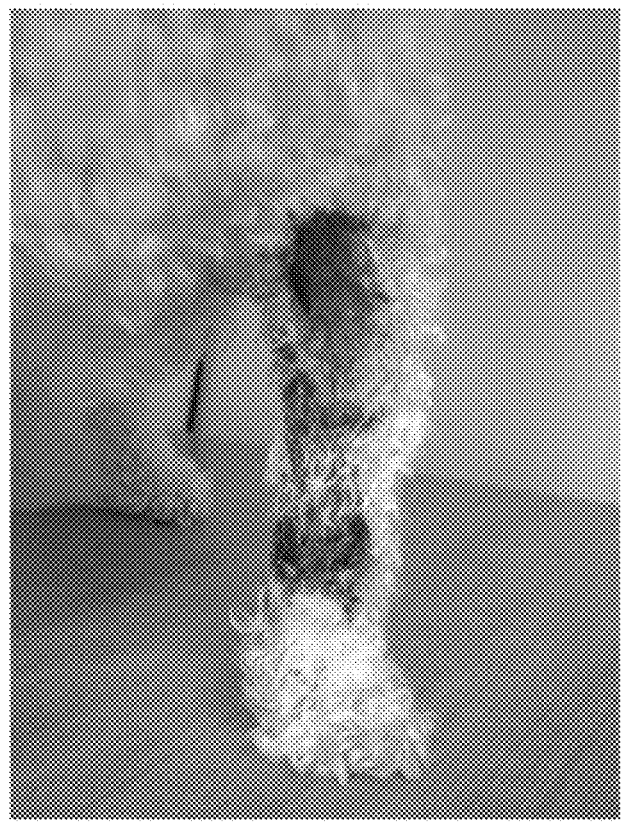
FIGS. 32A-B depict a patient of Example 25.
Figure 32B:

The cream has shown, in clinical use, to be effective on previously non responsive wounds and ulcerations. As shown in FIG. 32A, wound closure of a chronically infected festering open non healing wound with failure to respond to multiple different antibiotics including topical creams. The dog's owner consented to the use of the dog's case record, so that other patients could benefit in the way that the dog had. So impressed by the result of the treatment was the dog owner that he not only consented to the use of the initial case records, but he brought the dog back for follow up photographs (see, e.g., FIG. 32B). One of dog owner's more interesting comments was on how well the dog tolerated the creams application to such a large open and obviously tender wound as the initial bandaging and un-bandaging had obviously been so painful. The dog has returned to completely normal activity and unless one knew there had been a problem no one would know that the dog had ever been injured.

Figure 33A:
FIGS. 33A-B depict a patient of Example 25.
Figure 33A:
Figure 33B:
Figure 33B:

The cream creates a protective barrier around the entire wound. As shown in FIG. 33A, the wound healing of a very extensive degloved injury to the skin on the back and sides of a greyhound pictured only 24 hours after cream application. As shown in FIG. 33B, the patient had an uneventful recovery despite the degree of degloving and the extent of the wound and the previous history of the patient's wounds breaking down. The antibiotic cover was not extended beyond the initial 5 days and no analgesic or anti-inflammatory other than the HP Vet Cream was used.

Figure 34A:
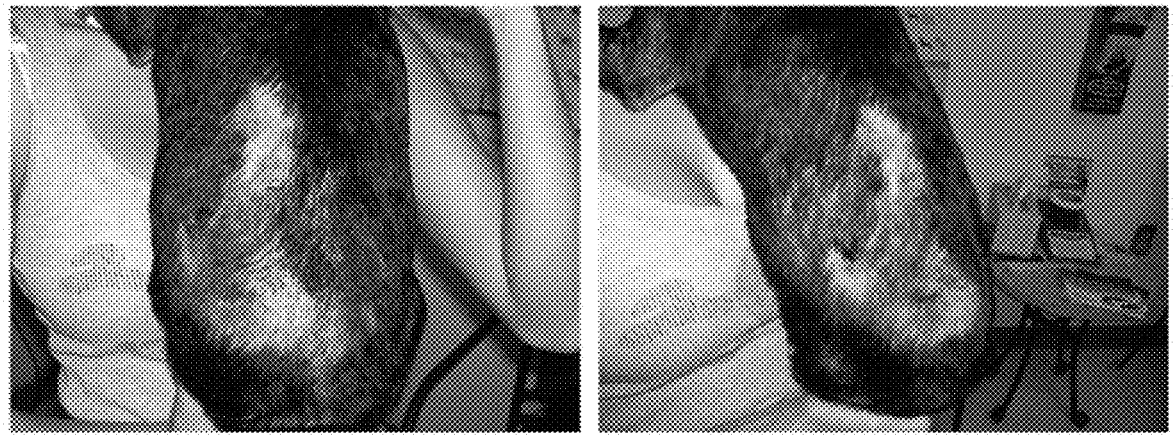
FIGS. 34A-B depict a patient of Example 25.
Figure 34B:
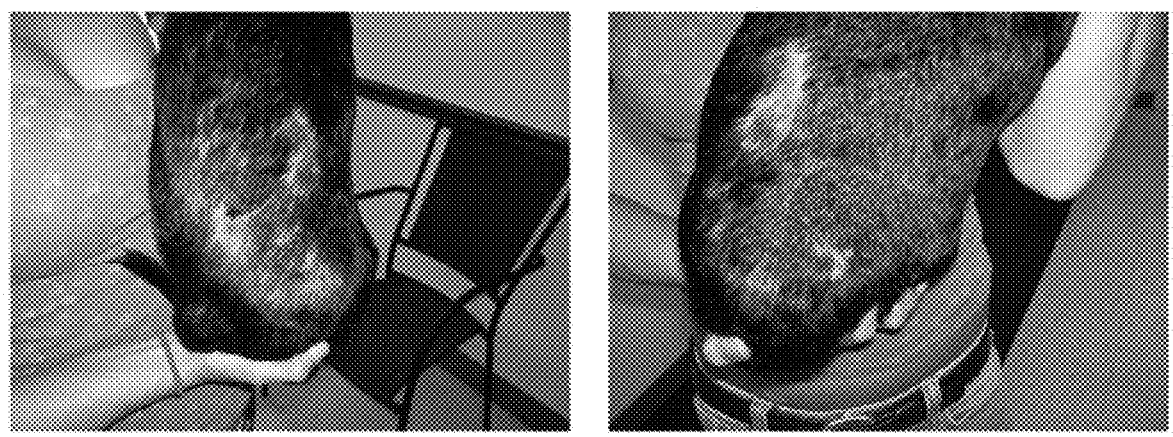

The cream may be used in conjunction with conventional antibiotic therapy to enhance effect. As shown in FIG. 34A, a dog had hair loss, itching and a skin disorder. The owner was administering triple antibiotic cream twice daily, baking soda baths once a week and dipping in happy jack flea and tick dip. The owner noticed the abrasions began to turn yellow and looked infected. The owner was subsequently instructed to apply HP Healing cream twice daily for 7-10 days. As shown in FIG. 34B, seven days later, The owner noted that itching had ceased. The skin was much improved and the hair had began to grow back in.

Figure 35A:
FIGS. 35A-B depict a patient of Example 25.
Figure 35B:
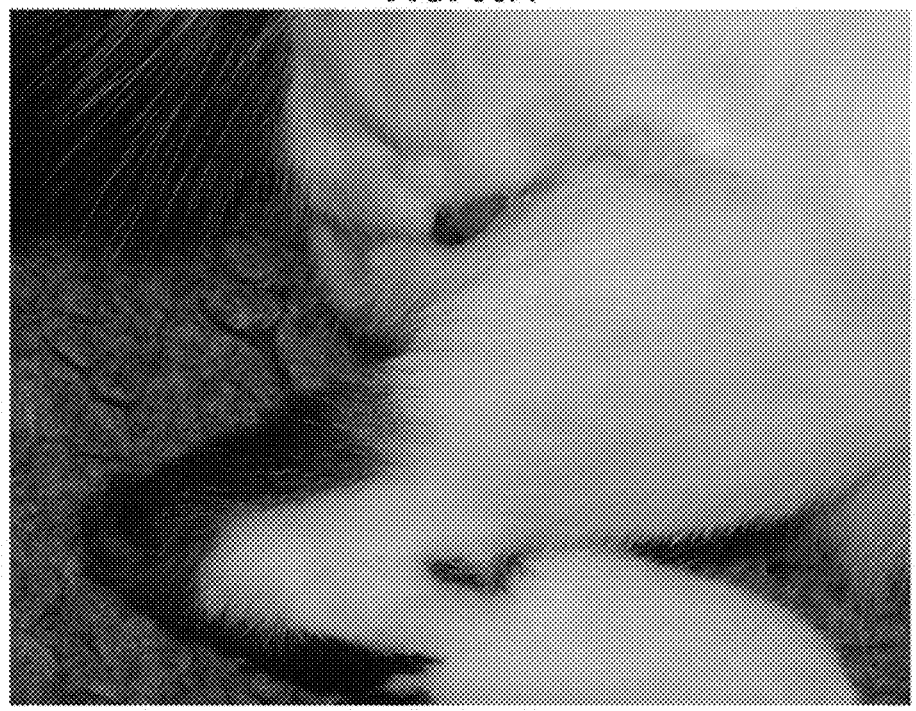
Figure 36A:
FIGS. 36A-B depict a patient of Example 25.
Figure 36A:
Figure 36B:
Figure 36B:

The non-steroidal cream also has a non-stringent property and seals in moisture. FIG. 35A depicts incorporation of HP Vet Cream in the treatment of a septic compound fracture and accompanying wound. FIG. 35B depicts the recovery in the case, which was dramatic considering the initial prognosis. What was interesting with the use of HP Vet Cream in this case was how its withdrawal resulted in slower healing until it was reintroduced and also how it improved hair growth around the wound The cream acts as a barricade under which cell regeneration can go unhindered and speed the closure and bridging of wounds. As shown in FIG. 36A, a dog was presented for a laceration on right side. The dog jumped off a fenced in area and caught herself on the fence. The dog was treated with HP Healing Cream, applied twice daily for 7 days. The dog was presented 7 days later for a re-check on the laceration on the right side. Laceration was reduced in size by half, as shown in FIG. 36B. The owner was instructed to continue to apply HP Healing Cream another two weeks.

Figure 37A:
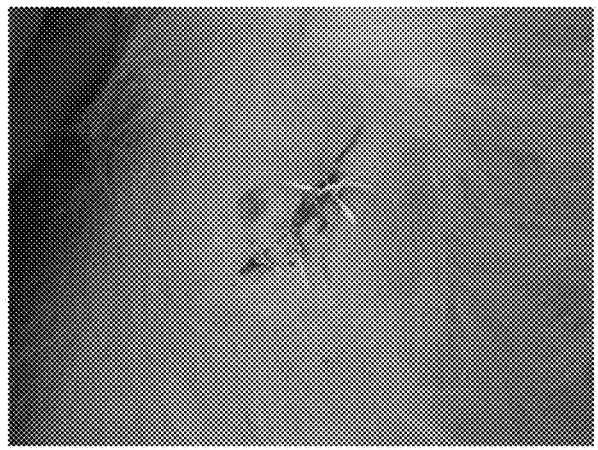
FIGS. 37A-B depict a patient of Example 25.
Figure 37A:
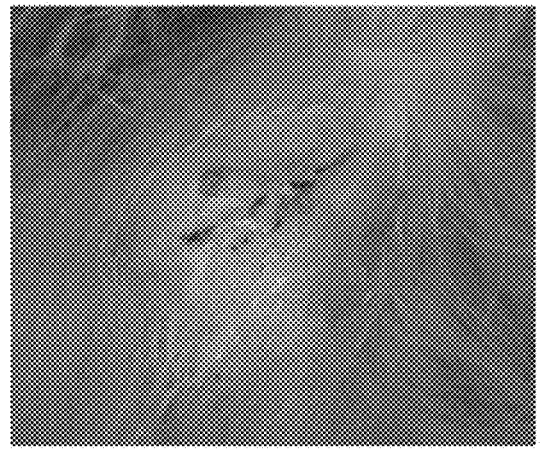
Figure 37B:
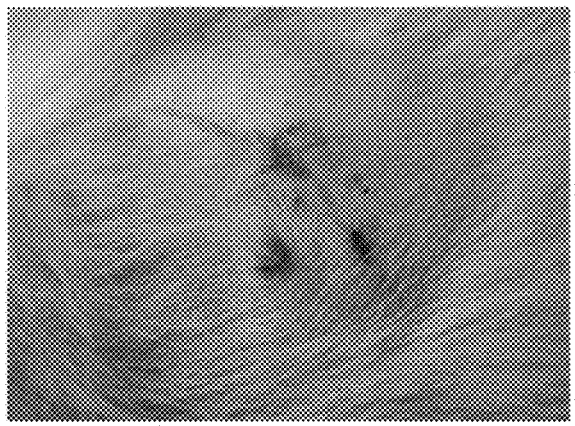
Figure 37B:
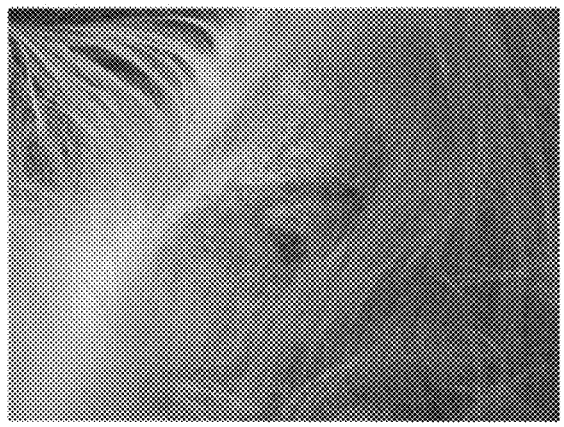

The cream can be used externally on open or bandaged wounds. Liberal application is recommended under bandage. FIG. 37A depicts the treatment of a simple slow healing wound with HP Vet Cream. The patient was presented to the clinic three weeks after the initial injury with an incised type wound that although small just would not heal and this was in part the patients own fault as it objected to normal forms of wound closure. As shown in FIG. 37B, Within two days of starting the application of HP Vet Cream the wound had started to heal and the owner reduced application of the cream to once daily. The wound had healed completely within six days of starting application of HP Vet Cream and the owner ceased applying the cream at that stage with no further problems and this was despite the fact that for the three previous weeks the wound had steadfastly refused to heal.

Figure 38A:
FIGS. 38A-B depict a patient of Example 25.
Figure 38B:
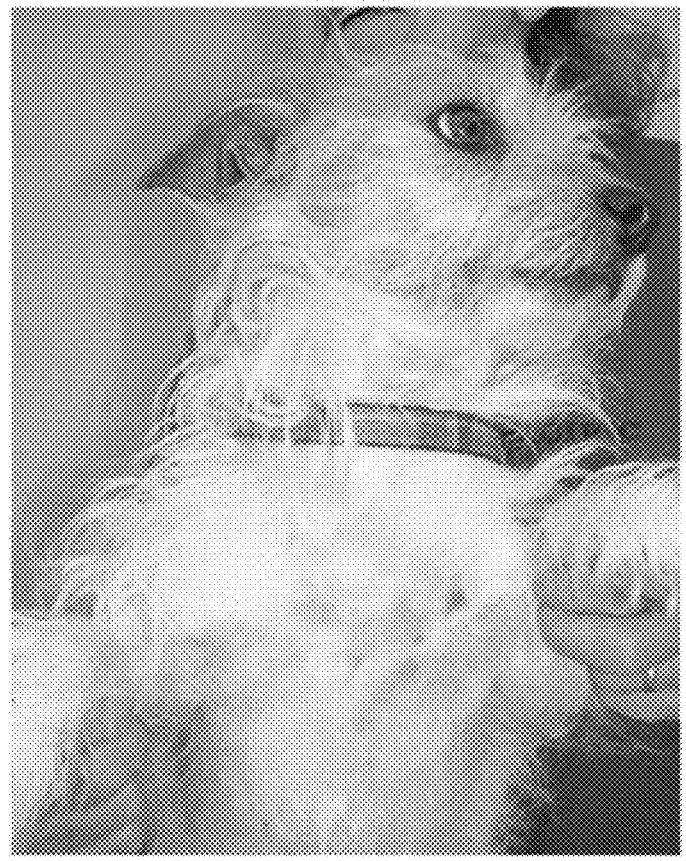

The cream works in conjunction with the body's natural healing mechanisms. As shown in FIG. 38A, accelerated wound closure and healing without suturing of acute bite wounds compounded with muscle laceration and severe deep and surface tissue bruising with the use of HP Vet Cream. As shown in FIG. 38B, the rapidity of healing is very clear when one looks at the state of the patient where there is a total disappearance of tissue bruising and all surface injuries other than the major wound points had literally vanished. In a patient with no anti-inflammatory or analgesic treatment one would not normally have expected the patient to be fully mobile in two days.

Figure 39A:
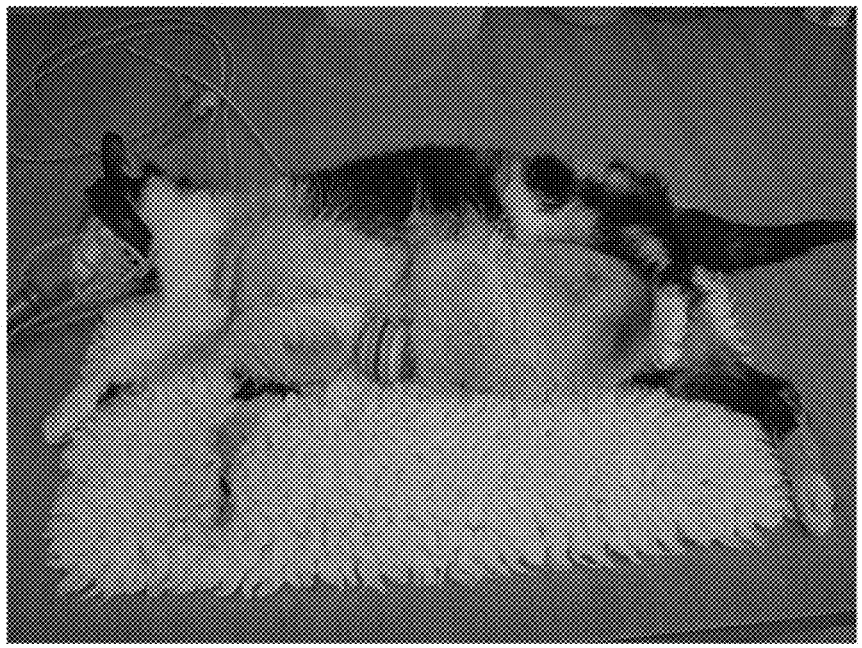
FIGS. 39A-B depict a patient of Example 25.
Figure 39A:
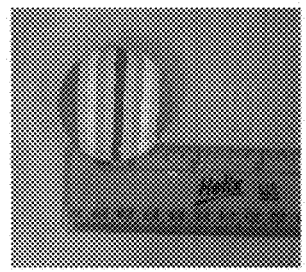
Figure 39B:

An anti-infective and anti-inflammatory effect are naturally provided. As shown in FIG. 39A, acelerated wound closure and healing without suturing of acute bite wounds compounded with muscle laceration and severe deep and surface tissue bruising with the use of HP Vet Cream. As shown in FIG. 39B, just 9 days after initial admital, the entire mammary hypertrophy had disappeared. One can see from the indentations on the practice golf ball that the cat was back to her initial kitten like self playing with toys.

Figure 40A:
FIGS. 40A-B depict a patient of Example 25.
Figure 40A:
Figure 40B:
Figure 40B:

The cream is not listed for use in cases of eczema. As depicted in FIG. 40A, there were lesions over the head, has hair loss with crusting and wrinkling of the skin. The cream was possibly being groomed off by kitten. As shown in FIG. 40B, the cat was presented to clinic again one week later for no improvement suggesting that the cream may not be suitable for cases of eczema.

This example demonstrates that the cream seals in moisture, an anti-infective, anti-inflammatory effect are naturally provided, a healing effect is transferred over the entire wound, may be used with conventional antibiotic therapy to enhance effect and is non stringent. The cream acts as barricade under which cell regeneration can go unhindered and speeds the closure and bridging of wounds. The cream can be used externally on open or bandaged wounds (liberal application is recommended under bandages). The cream has been shown in clinical use to be effective on previously non-responsive wounds and ulcerations. The cream also works in conjunction with the body's natural healing mechanisms.

Example 26: Additional Human Studies

White Female: 60 Years Old

Figure 41A:
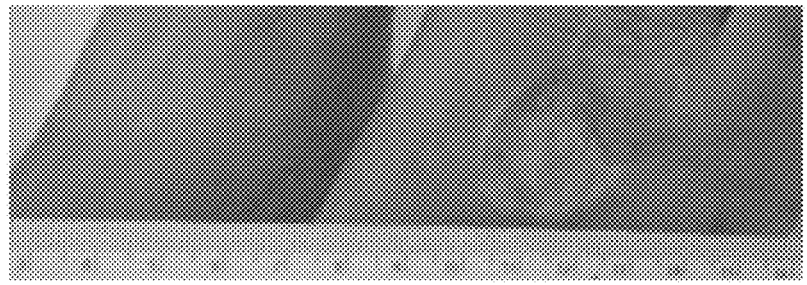
FIGS. 41A-G depict a patient of Example 26.
Figure 41B:
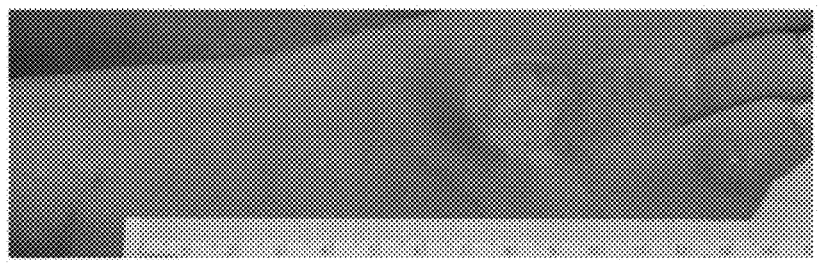
Figure 41C:
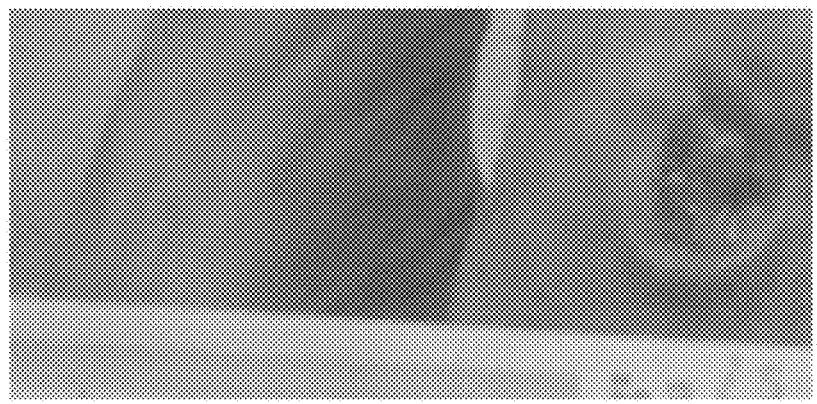
Figure 41D:
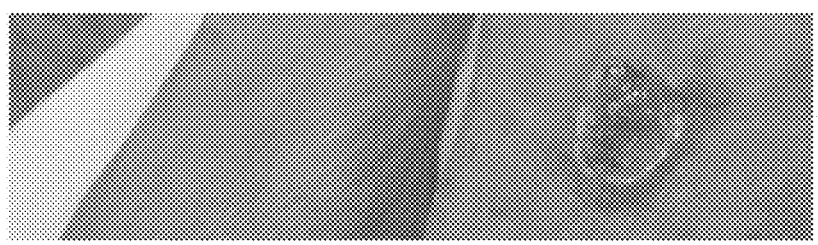
Figure 41E:
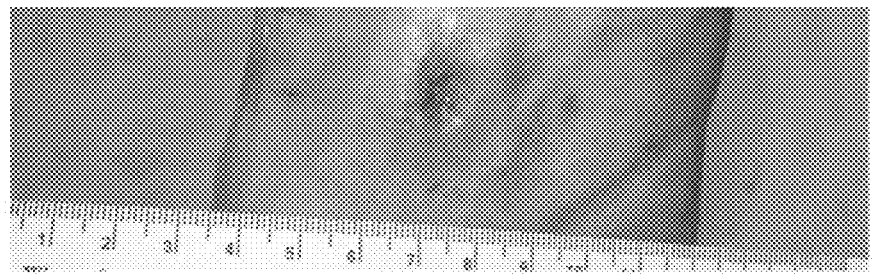
Figure 41F:
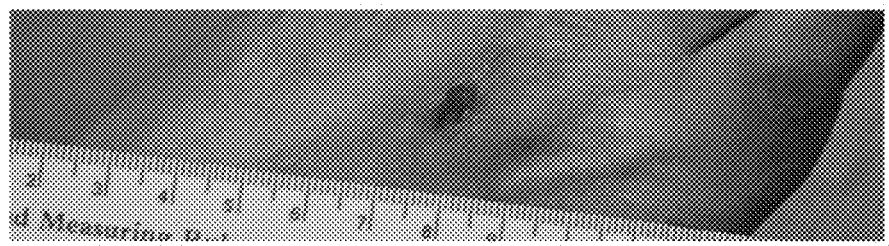
Figure 41G:
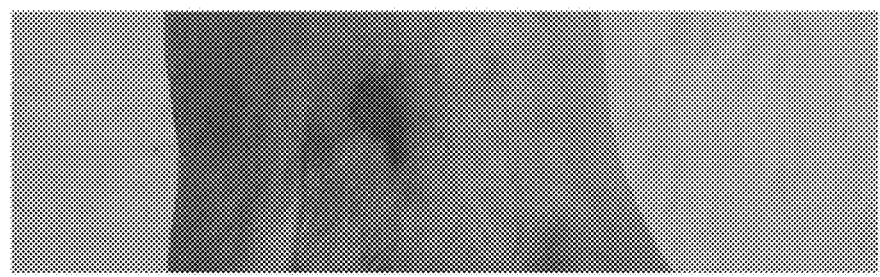

After no response from conventional treatment, including antibiotics and Hyperbaric chamber (FIGS. 41A-B), client was placed on the cream (FIGS. 41C-D). Improvement was visible after six weeks (FIGS. 41D-E) and two months (FIG. 41F). She was able to attend a wedding with open shoes.

Male with Ingrown Hair

A 33 year old male with an ingrown hair that had become a 6 month long treatment course. The wound was surgically treated to attempt to bring the wound walls closer to attempt to support healing. Pain medication along with conventional antibiotic coverage and Hyberbaric chamber, repeated surgical wound debridement and wound edge cleaning treatments over a one year period along with alternating wet to moist compression bandaging with no success.

Figure 42A:
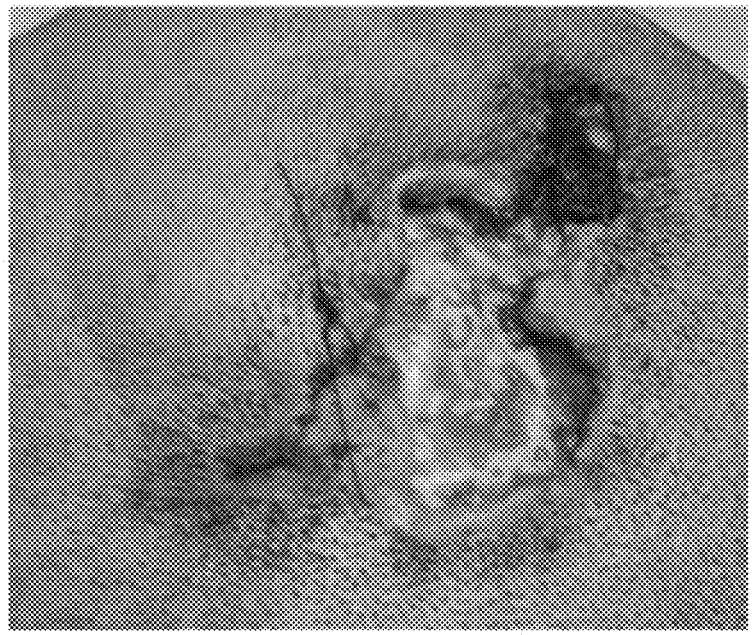
FIGS. 42A-C depict a patient of Example 26.
Figure 42B:
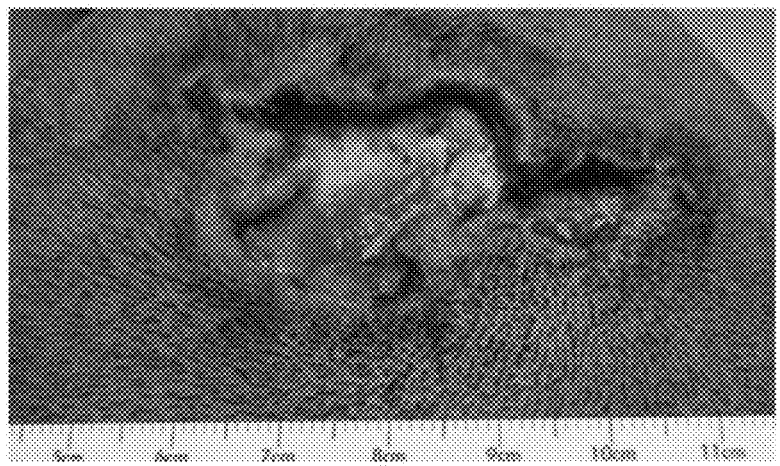
Figure 42C:
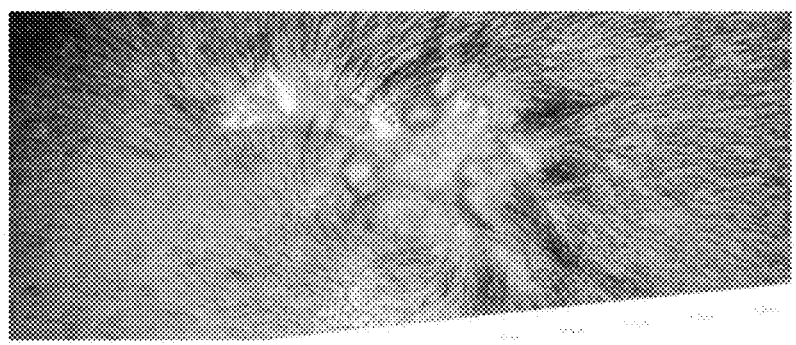

In 6 weeks of treatment with the healing cream the wound has progressed to closure and full healing (FIGS. 42A-C). The wound centers doctors were so impressed with the patients response to the cream that his case was presented as a poster at a wound healing conference. The invention is further described by the following numbered paragraphs:

1. An anti-infective homeopathic complex comprising a homeopathic tincture or dilutions thereof of Hepar sulphuris calcareum or other similar profiled *Calcarea* or Sulphur salt or acid, Lachesis muta or other remedy with a similar profile, Mercurius Solubilis or similar mercury containing remedy, and Silica or other silica containing remedy.
2. A homeopathic complex according to paragraph 1 wherein Hepar Sulphuris calcareum is replaced or supplemented with Calc Sulph or Calc Sil.
3. A homeopathic complex according to paragraph 1 or paragraph 2 wherein Lachesis muta is replaced or supplemented with a snake or spider remedy with a similar septic shock profile, preferably Crotalidae (*Crotalus* Horridalus), Pyrogen and/or Tarentula *Cubensis*.
4. A homeopathic complex according to any of paragraph 1 to 3 wherein Mercurius Solulbilis is replaced or supplemented with *Phytolacca* decandra.
5. A homeopathic complex according to any of the preceding paragraphs in a potency range from mother tincture to 100M, preferably from mother tincture to 50M.
6. A homeopathic complex according to any of paragraphs 1 to 4 in LM potencies.
7. A homeopathic complex according to any of the preceding paragraphs comprising a homeopathic tincture or dilutions thereof of the Ranunculacea family, preferably the Aconite or Aconitine, more preferably Aconite napellus [Acon];

the Compositae family, preferably *Arnica montana* [Arn]; *Bellis perennis* [Bell-p]; Calendula Offcinalis [Calen]; *Chamomilla Matricaria* [Cham]; *Millefolium achillea* [Mill]; *Carduus* Marianus; and/or *Echinacea*, preferably *Echinacea angustifolia* [Echi]; *Echinacea purpurea* [Echi-p];

the Solanacea family, preferably *Belladonna* [Bell];

Arsenicum, preferably Arsenicum iodatum [Ars-i] and/or Arsenicum Album;

Bryonia alba [Bry];

*Hamamelis virginiana* [Ham];

*Hypericum* Perforatum [Hyper];

Ledum *palustre* [Led];

*Phytolacca* decandra [Phyt];

the Anacardiacea family preferably *Rhus Toxicodendron* [*Rhus*-T.];

the Rutaceae family preferably *Ruta* Graveolans [*Ruta*];

Stellaria media [Stel]; and/or

Symphytum *officinale* [Symph].

8. A homeopathic complex according to any of the preceding paragraphs comprising a homeopathic tincture or dilutions thereof of Aconite napellus [Acon]

*Arnica montana* [Arn];

Arsenicum iodatum [Ars-i];

*Belladonna* [Bell];

*Bellis perennis* [Bell-p];

Bryonia alba [Bry];

Calenula Offcinalis [Calen];
*Echinacea angustifolia* [Echi];
*Echinacea purpurea* [Echi-p];
*Hamamelis virginiana* [Ham];
*Hypericum* Perforatum [Hyper];
Ledum *palustre* [Led];
*Millefolium achillea* [Mill];
*Phytolacca* decandra [Phyt];
*Rhus Toxicodendron* [*Rhus*-T.];
*Ruta* Graveolans [*Ruta*]; and
Symphytum *officinale* [Symph].

9. A homeopathic complex according to paragraph 7 or paragraph 8 further comprising optional Core B ingredients *Thuja Occidentalis* [Thuj], *Chamomilla Matricaria* [Cham], *Stellaria media* [Stel] and/or Sulphur [Sulph].

10. A homeopathic complex according to any of paragraphs 7 to 9 further comprising optional Core B ingredient Graphites naturalis.

11. A homeopathic complex according to any of paragraphs 7 to 10 further comprising Apis mellifica [Apis], *Urtica urens* [Urt-u], and Unbelliferae preferably *Conium maculatum* and/or Gunpowder.

12. A homeopathic complex according to any of the preceding paragraphs further comprising a homeopathic tincture or dilutions thereof of
The Arsenicums, preferably Arsenicum album [Ars];
The Barytas and Cabonicums, preferably Baryta carbonica [Bar-c] and/or *Kali*
Carbonicum;
Carbo vegetabilis [Carb-v];
The Calcareas, preferably *Calcarea* carbonica [Calc]; *Calcarea* fluorica [Calc-f] and/or *Calcarea* phosphorica [Calc-p];
*Gelsemium sempervirens* [Gels];
Iodium purum [Iod];
The Kalis, preferably *Kali* iodatum [*Kali-i*] and/or *Kali* Carbonicum
Lacs, preferably Lac *caninum* [Lac-c]; Lac vaccinum and/or Lac Vaccinum (cow);
Lycopodium *clavatum* [Lyc];
The Natrums and Muriatricums, preferably Natrum Mur
Nux vomica [Nux-v];
Phosphorus, preferably Phosphorus [Phos] and/or Ferrum Phos;
the Ranunculacea family, preferably *Pulsatilla nigricans* [Puls] and/or Staphysagria [Staph];
*Sabal serrulata* [*Sabal*];
Sepia succus [September]; and/or
Zincums preferably Zincum metallicum [Zinc].
Baptisia *tinctoria;*
Pyrogen;
*Astragalus membranaceus;*
*Bufo* rana; and/or
Ipecacuanha.

13. A homeopathic complex according to paragraph 12 further comprising Cantharis, Causticum, Crategus, Ferrum Phos and/or *Laurocerasus*.

14. A homeopathic complex according to any of the preceding paragraphs further comprising a homeopathic tincture or dilutions thereof of
Adrenalin [Adren];
*Aesculus hippocastanum* [Aesc];
Alfalfa;
Aurums;
The Antimoniums, preferably Antimonium Tart
*Berberis Vulgaris;*
Cactus *Grandiflora;*
*Caladium* seguinum [Calad];
Cantharis vesicatoria [Canth];
*Carduus* Marianus;
Cocculus *indicus* [Cocc];
*Chelidonium;*
China *officinalis;*
*Chionanthus virginica;*
Drosera *rotundifolia;*
Equisetum hyemale;
Euphrasia:
Galium Aprine;
Grindelia;
Histaminium (Histamine) [Hist];
Hydrastis *canadensis* [Hydr];
*Lappa* Articum;
Lavender [Lav-v.];
*Lobelia inflata;*
Mezereum [Mez];
Nitric acid [Nit-ac];
*Paeonia Officinalis* [Paeon];
Prednisolone [Predni.];
*Ranunculus bulbosus* [Ran-b];
*Rumex crispus* [Rumx];
Solidago virgaurea;
Strophantus *hispidus;*
Taraxacum *officinale;*
*Triticum Repens;*
The Stannums preferably Stannum Met;
Thiosinaminum [Thiosin];
Uva *Ursi;*
Veratrum Album;
Cuprum met; and/or
Sol [Sol].

15. An anti-infective homeopathic complex comprising a homeopathic tincture and dilutions thereof of the following ingredients: Hepar Sulph; Lachesis; Merc; Sil; Aconite napellus; *Arnica montana*; Arsenicum iodatum; *Belladonna; Bellis perennis*; Bryonia alba; Calenula Offcinalis; *Chamomilla Matricaria; Echinacea angustifolia; Echinacea purpurea*; Graphites naturalis; *Hamamelis virginiana; Hypericum* Perforatum; Ledum *palustre; Millefolium achillea; Phytolacca* decandra; *Rhus Toxicodendron; Ruta* Graveolans; *Stellaria media*; Sulphur; Symphytum *officinale*; and *Thuja Occidentalis*.

16. An anti-infective homeopathic complex comprising a homeopathic tincture and dilutions thereof of the following ingredients: Aconitum Napellus; *Arnica Montana*; Arsenicum Iod; *Belladonna; Bellis* Perenis; Bryonia Alba; Calenula Offcinalis; *Chamomilla Matricaria; Conium maculatum*; Echinacia augustofolia; Echinacia *Purpurea*; Graphites Gunpowder; Hamamellis Virginia; Hepar Sulphuris; *Hypericum* Perforatum; Lachesis; Ledum; *Millefolium*; Mercurius Solubilis; *Phytolacca* decandra; *Ruta* Graveolans; *Rhus Toxicodendron*; Silica [Sil]; *Stellaria Media*; Sulphur; Symphytum; *Thuja Occidentalis*; and *Urtica Urens*.

17. An anti-infective homeopathic complex according to paragraph 15 or paragraph 16 wherein the homeopathic ingredients are provided in a potency range from Mother tincture to 18×.

18. An anti-infective homeopathic complex according to any of paragraphs 15 to 17 in a form suitable for topical administration.

19. An anti-infective homeopathic complex comprising a homeopathic tincture and dilutions thereof of the following ingredients: Aconite; Apis; *Arnica Montana*; Arsencium Iod; *Belladonna; Bellis Perennis*; Bryonia; Calendula; Cantharis; Carbo Veg; Causticum; *Conium*; Crategus; *Echinacea* Anugustifolia; *Echinacea* Purpura; Ferrum Phos; *Gelsemium*; Hammamellis; Hepar Sulph; *Hypericum*; Lachesis; *Laurocerasus*; Ledum; Merc Sol; *Millefolium*; Nux Vomica; Phosphorus; *Phytolacca; Rhus* Tox; *Ruta* Grav; Silica; Sulphur; Staphysagria; Symphytum; *Urtica; Chamomilla* matrica; and *Stellaria*.

20. An anti-infective homeopathic complex according to paragraph 19 wherein the homeopathic ingredients are provided in a potency range from 30C and greater, preferably 200C and greater and LM potencies.

21. An anti-infective homeopathic complex according paragraph 19 or paragraph 20 in a form suitable for internal administration.

22 A homeopathic complex according to any of the preceding paragraphs further comprising nosodes.

23. A homeopathic complex as paragraphed in any of the preceding paragraphs in a form adapted for topical delivery wherein the ingredients are present at a potency range from Mother Tincture to 30c, preferably from Mother Tincture to 12c, more preferably from Mother Tincture to 9c, even more preferably from mother tincture to 30×.

24 A homeopathic as paragraphed paragraph 23 in the form of a liquid, cream, lotion, gel or in a form adapted for administration in a dressing or bandage.

25. A homeopathic complex as paragraphed in any of the preceding paragraphs in a form adapted for internal delivery wherein the core ingredients are present at a potency range from 1C to 100M, preferably 12C to 1M, more preferably from 30C to 1M, more preferably from 200C to 1 M, even more preferably 1M to 10M and including LM potencies.

26. A homeopathic as paragraphed paragraph 25 in the form of an oral tablet, pill, pillule, gel cap, spray and/or drop.

27 A homeopathic complex as paragraphed in any of the preceding paragraphs further comprising conventional pharmaceutical excipients and/or carriers.

28 A combination therapy comprising the homeopathic complex as paragraphed in any of the preceding paragraphs and a conventional pharmaceutical.

29. A combination therapy according to paragraph 28 wherein the conventional pharmaceutical is an orally administered antibiotic or topically administered antibiotic.

30. A homeopathic complex as paragraphed in any of the preceding paragraphs for use in therapy.

31 A homeopathic complex as paragraphed in any of the preceding paragraphs for use in the treatment or prophylaxis of infection as an anti-infective agent, preferably in the treatment, control or prophylaxis of MRSA or other multi-resistant microbial strains.

32. A homeopathic complex as paragraphed in any of the preceding paragraphs for use in the regeneration of diseased or damaged tissue.

33 A homeopathic complex as paragraphed in paragraph 16 for use in the treatment of mastitis.

34. A homeopathic complex as paragraphed in paragraph 19 for use as a first aid remedy.

35. A homeopathic complex as paragraphed in any of the preceding paragraphs for use in the treatment of humans and animals, including canines, equines, porcine and/or felines.

36. A method for the manufacture of a medicament comprising a homeopathic complex as paragraphed in any of paragraphs 1 to 27 for use in the treatment or prophylaxis of infection and/or the regeneration of diseased or damaged tissue.

37. A method for the treatment or prophylaxis of infection and/or the regeneration of diseased or damaged tissue in a subject comprising the steps of administering an effective amount of a homeopathic complex as paragraphed in any of paragraphs 1 to 27 to a patient in need of such treatment.

38. A cosmetic preparation comprising a homeopathic complex as paragraphed in any of paragraphs 1 to 27 and a suitable cosmetic carrier.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for treating an ulcerative wound, which comprises administering an effective amount of an oral or topical composition comprising Hepar sulphuris calcareum, Lachesis muta, Mercurius Solubilis, and silica.

2. The method according to claim 1, wherein the composition further comprises Aconitum napellus, *Arnica montana, Arsenicum iodatum, Belladonna, Bellis perennis, Bryonia alba, Calendula officinalis, Matricaria chamomilla, Echinacea angustifolia, Echinacea* purpurea, *Hamamelis virginiana, Hypericum* perforatum, Ledum *palustre, Achillea millefolium, Phytolacca decandra, Rhus Toxicodendron, Ruta graveolens, Stellaria media*, sulphur, Symphytum *officinale*, or *Thuja occidentalis*.

3. The method according to claim 2, wherein the composition further comprises at least one additional component selected from the group consisting of Apis mellifica, alfalfa, Ipecacuanha, Nux vomica, phosphorus, Sol, Causticum, Calcera fluorica, and Graphites.

4. The method according to claim 2, wherein the composition is a liquid composition.

5. The method according to claim 4, wherein the composition is a topical composition.

6. The method according to claim 5, wherein the topical composition is in the form of an ointment, cream, lotion, oil, liniment, spray, or gel.

7. The method according to claim 6, wherein the topical composition is administered in the form of a dressing or bandage comprising said topical composition.

8. The method according to claim 1, wherein the composition further comprises a base.

9. The method according to claim 8, wherein the base comprises about 15 to 35% lanolin, about 15 to 35% mineral oil, and about 40 to 60% petroleum.

10. The method according to claim 2, wherein the composition further comprises *Conium maculatum* or gunpowder.

11. The method according to claim 4, wherein the liquid composition is an oral composition.

12. The method according to claim 11, wherein the oral composition is in the form of a tablet, pill, pillule, gel cap, spray, or drop.

13. The method according to claim 1, wherein the composition is for systemic administration.

14. The method according to claim 1, wherein the composition is for parenteral administration.

15. The method according to claim 1, wherein the composition is a suppository.

* * * * *